United States Patent
Babcook et al.

(10) Patent No.: US 11,390,673 B2
(45) Date of Patent: Jul. 19, 2022

(54) ANTI-PODOCALYXIN ANTIBODIES AND METHODS OF USING THE SAME

(71) Applicants: CENTRE FOR DRUG RESEARCH AND DEVELOPMENT, Vancouver (CA); THE UNIVERSITY OF BRITISH COLUMBIA, Vancouver (CA)

(72) Inventors: John Stephen Babcook, Vancouver (CA); Kelly Marshall McNagny, Vancouver (CA); Calvin D. Roskelley, Vancouver (CA); Bradley John Hedberg, Vancouver (CA); Kimberly Ashely Snyder, Vancouver (CA); Michael R. Hughes, Vancouver (CA)

(*) Notice: Subject to any disclaimer, the term of this patent is extended or adjusted under 35 U.S.C. 154(b) by 52 days.

(21) Appl. No.: 16/538,744

(22) Filed: Aug. 12, 2019

(65) Prior Publication Data
US 2019/0367606 A1    Dec. 5, 2019

Related U.S. Application Data

(63) Continuation of application No. 15/031,244, filed as application No. PCT/CA2014/051020 on Oct. 21, 2014, now abandoned.

(60) Provisional application No. 61/893,817, filed on Oct. 21, 2013.

(51) Int. Cl.
| A61K 39/00 | (2006.01) |
| C07K 16/28 | (2006.01) |
| C07K 16/30 | (2006.01) |

(52) U.S. Cl.
CPC .............. *C07K 16/28* (2013.01); *C07K 16/30* (2013.01); *A61K 2039/505* (2013.01); *C07K 2317/20* (2013.01); *C07K 2317/24* (2013.01); *C07K 2317/33* (2013.01); *C07K 2317/52* (2013.01); *C07K 2317/56* (2013.01); *C07K 2317/565* (2013.01); *C07K 2317/567* (2013.01); *C07K 2317/73* (2013.01); *C07K 2317/92* (2013.01)

(58) Field of Classification Search
CPC .. C07K 16/28; C07K 16/30; C07K 2317/565; C07K 2317/24; C07K 2317/73; A61P 35/00
See application file for complete search history.

(56) References Cited

U.S. PATENT DOCUMENTS

| 7,807,794 B2 * | 10/2010 | Lazarides | G01N 33/6872 |
| | | | 530/387.3 |
| 7,833,733 B2 | 11/2010 | McNagny et al. | |
| 8,828,387 B2 | 9/2014 | Kajikawa et al. | |

| 2009/0123461 A1 | 5/2009 | Fitzhugh et al. | |
| 2010/0061978 A1 | 3/2010 | Huntsman et al. | |
| 2013/0287783 A1 * | 10/2013 | Frank | C07K 16/28 |
| | | | 424/139.1 |

FOREIGN PATENT DOCUMENTS

| EP | 2452950 A1 | 5/2012 | |
| WO | WO 2007/102787 A1 | 9/2007 | |
| WO | WO 2012/011876 A1 | 1/2012 | |
| WO | WO-2014031476 A1 * | 2/2014 | ............. C07K 16/28 |
| WO | WO 2015/058301 A1 | 4/2015 | |

OTHER PUBLICATIONS

Paul, Fundamental Immunology, 3rd Edition, 1993, pp. 292-295 (Year: 1993).*
Rudikoffetal (Proc. Natl. Acad. Sci. USA 1982 vol. 79: p. 1979) (Year: 1979).*
Pascalis et al. (The Journal of Immunology (2002) 169, 3076-3084) (Year: 2002).*
Gasset et al. (2003) BBRC 307, 198-205, (Year: 2003).*
George et al. (Circulation. 1998; 97: 900-906), (Year: 1998).*
Brown et al (J. Immunol. May 1996; 156(9):3285-3291 (Year: 1996).*
Vajdos et al (J. Mol. Biol. Jul. 5, 2002;320(2); 415-428) (Year: 2002).*
Almagro & Fransson, Frontiers in Bioscience 2008; 13:1619-33 (Year: 2008).*
Tan, Stem Cell vol. 27 p. 1792 (2009). (Year: 2009).*
Rodriguez et al, Journal compilation vol. 68 p. 407 (2006) (Year: 2006).*
U.S. Appl. No. 15/031,244 (U.S. Publication No. 2016-0264663), entitled, "Anti-Podocalyxin Antibodies and Methods of Using the Same", filed Apr. 21, 2016, of Babcook, et al. (Abandoned).
U.S. Appl. No. 15/765,233 (U.S. Pat. No. 11,090,383), entitled, "Anti-Podocalyxin Antibodies and Methods of Using the Same", filed Mar. 30, 2018 , of McNagny, et al.
U.S. Appl. No. 17/402,460, entitled, " Anti-Podocalyxin Antibodies and Methods of Using the Same", filed Aug. 13, 2021, of McNagny, et al.
Binder et al., "Podocalyxin-Like Protein Is Expressed in Glioblastoma Multiforme Stem-Like Cells and Is Associated with Poor Outcome", Plos One, vol. 8:(10), p. e75945, pp. 1-15 (2013).
Blixt et al., "Printed covalent glycan array for liand profiling of divers glycan binding proteins", PNAS, vol. 101, No. 49, pp. 17033-13038 (2004).
Boman et al., "Membranous expression of podocalyxinplike protein is an independent facttor ofpoor prognosis in urothelial bladder cancer", Br J Cancer, vol. 108(11), pp. 2321-2328 (2013).

(Continued)

*Primary Examiner* — Sheela J. Huff
(74) *Attorney, Agent, or Firm* — Todd Lorenz

(57) ABSTRACT

The present invention is directed to compositions of matter useful for the treatment of cancer in mammals and to methods of using those compositions of matter for the same. Antibodies specific for podocalyxin designated Ab1 and 3G2 are disclosed, as is the use of said antibodies for the inhibition of growth of a tumor that expresses podocalyxin, and the use of said anti bodies for targeting tumour endothelial cells that express podocalyxin.

17 Claims, 21 Drawing Sheets

Specification includes a Sequence Listing.

(56) References Cited

OTHER PUBLICATIONS

Bovin et al., "Repertoire of human natural anti-glycan immunoglobulins. Do we have auto-antibodies?", Biochimica et Biophisica Acta 1820, pp. 1373-1382 (2012).
Brand et al., "Prospect for Anit-HER2 Receptor Therapy in Breast Cancer" Anticancer Res., vol. 26, pp. 463-470 (2006).
Choo A.B. et al., "Selection against undifferentiated human embryonic stem cells by a cytotoxic antibody recognizing podocalyxin-like protein-1" Stem Cells, vol. 26(6), pp. 1454-1463 (2008).
Cipollone et al., "The Anti-adhesive mucin podocalyxin may help initiate the transperiotoneal metastasis of high grade werous ovarian carcinoma", Clin Exp Metasatasis, vol. 29(3), pp. 239-252 (2012).
Dallas et al., "Sialofucosylated podocalyxin is a function E- and L-selctin ligand expressed by metastatic pancreatic cancer cells", AM J Phsiol Cell Phsiol, vol. 303: C616-C624 (2012).
Doyonnas et al.,"Anuria, Omphalocele, and Preintal Lethality in Mice Lacking the CD34-related Protein Podocalyxin", J Exp Med, vol. 194 (1), pp. 13-27 (2001).
Heukamp et al., "Podocalyxin-like protein 1 expression in primary hepatic tumours and tumour-like lesions", Histopathology, vol. 49(3), pp. 242-247 (2006).
Hsu et al., "Podocalyxin EBP50 Ezrin Molecular Complex Enhances the Metastatic Potential of Renal Cell Carcinoma Though Recruiting Rael Guanine Nucleotide Exchange Factor ARHGEF7", Am J Pathology, vol. 176(6), pp. 3050-3061 (2010).
Jacob et al., "The clycosphingolipid Pl is an ovarian cancer-associated carbohydrate antigen involved in migration", Britsh J of Cancer, vol. 111, pp. 1634-1645 (2014).
Kaprio et al., "Podocalyxin is a marker of poor prognosis in colerectal cancer", BMC Cancer, vol. 14:493, pp. 1-7 (2014).
Konstantopoulos et al., "Cancer Cells in Transit: The Vascular Interactions of Tumor Cells", Annu Rev Biomed Eng, vol. 11, pp. 177-202 (2009).
Larsson et al. "Overexpression of podocalyxin-like protein is an independent factor of poor prognosis in colorectal cancer", British Journal of Cancer, vol. 105(5), pp. 666-672 (2011).
Natunen et al., "The binding specificity of the marker antibodies Tra-1-60 and Tra-1-81 reveals a novel pluripotency-associated type 1 lactosamine epitope", Glycobiology, vol. 21, No. 9, pp. 1125-1130 (2011).
Nielsen et al., "Novel functions of the CD34 family", Journal of Cell Science, vol. 121, No. 22, pp. 3683-3692 (2008).
Nielsen et al., "The Role of Pdocalyxin in Health and Disease", J Am Soc Nephrol, vol. 20, pp. 1669-1676 (2009).
Oh et al., "Live dynamic imaging of caveolae pumping targeted antibody rapidly and specifically across endothelium in the lung : Abstract: Nature Biotechnology", Nature Biotechnology: Abstract (2007).
Ono et al., " Glycosylation defining cancer cell motility and invasiveness" Glycoconjugate Journal, vol. 20, pp. 71-78 (2004).
Snyder et al., "Podocalyxin enhances breast tumor growth and metastasis and is a target for monoclonal antibody therapy", Breast Cancer Research, Current Medicine Group Ltd, GB, vol. 17, No. 1, pp. 1-14 (2015).
Somasiri et al.,"Overexpressioin of the Anti-Adhesin Podocalyxin Is an Independent Predictor of Breast Cancer Progression", Cancer Research, vol. 64 (15): 5068-5073 (2004).
Strome et al., "A Mechanistic Perspective of Monoclonal Antibodies in Cancer Therapy Beyond Target-Related Effects" The Oncologist, vol. 12, pp. 1084-1095 (2007).
Thomas et al., "Identification , characterization and utilization of tumor cell selectin ligands in the design of colon cancer diagnostics", Biorheology, vol. 46 (3), pp. 207-225 (2009).
Thomas et al., "Podocalyxin-like protein is an E-/L-selectin ligand on colon carcinoma cells: comparative biochemical properties of selectin ligands in host and tumor cells", Am J Physiol Cell Physiol, vol. 296 (3), pp. C505-C513 (2009).
Tuccillo et al., "Aberrant glycosylation as biomarker for cancer: focus on CD43", Biomed Reaserach International, United States, pp. 2314-6141 (2014).

* cited by examiner (SEQ ID NO. 1)
MRCALALSALLLLLSTPPLLPSSPSPSPSPSQNATQTTTDSSNKTAPTPASSV
TIMATDTAQQSTVPTSKANEILASVKATTLGVSSDSPGTTTLAQQVSGPVNTT
VARGGGSGNPTTTIESPKSTKSADTTTVATSTATAKPNTTSSQNGAEDTTNSG
GKSSHSVTTDLTSTKAEHLTTPHPTSPLSPRQPTSTHPVATPTSSGHDHLMKI
SSSSSTVAIPGYTFTSPGMTTTLLETVFHHVSQAGLELLTSGDLPTLASQSAG
ITASSVISQRTQQTSSQMPASSTAPSSQETVQPTSPATALRTPTLPETMSSSP
TAASTTHRYPKTPSPTVAHESNWAKCEDLETQTQSEKQLVLNLTGNTLCAGGA
SDEKLISLICRAVKATFNPAQDKCGIRLASVPGSQTVVVKEITIHTKLPAKDV
YERLKDKWDELKEAGVSDMKLGDQGPPEEAEDRFSMPLIITIVCMASFLLLVA
ALYGCCHQRLSQRKDQQRLTEELQTVENGYHDNPTLEVMETSSEMQEKKVVSL
NGELGDSWIVPLDNLTKDDLDEEEDTHL (SEQ ID NO. 42)
MRCALALSALLLLLSTPPLLPSSPSPSPSPSQNATQTTTDSSNKTAPTPASSV
TIMATDTAQQSTVPTSKANEILASVKATTLGVSSDSPGTTTLAQQVSGPVNTT
VARGGGSGNPTTTIESPKSTKSADTTTVATSTATAKPNTTSSQNGAEDTTNSG
GKSSHSVTTDLTSTKAEHLTTPHPTSPLSPRQPTSTHPVATPTSSGHDHLMKI
SSSSSTVAIPGYTFTSPGMTTTLPSSVISQRTQQTSSQMPASSTAPSSQETVQ
PTSPATALRTPTLPETMSSSPTAASTTHRYPKTPSPTVAHESNWAKCEDLETQ
TQSEKQLVLNLTGNTLCAGGASDEKLISLICRAVKATFNPAQDKCGIRLASVP
GSQTVVVKEITIHTKLPAKDVYERLKDKWDELKEAGVSDMKLGDQGPPEEAED
RFSMPLIITIVCMASFLLLVAALYGCCHQRLSQRKDQQRLTEELQTVENGYHD
NPTLEVMETSSEMQEKKVVSLNGELGDSWIVPLDNLTKDDLDEEEDTHL

FIG. 1

Heavy chain variable region nucleic acid sequence (SEQ ID NO. 2)
ATGGAGACTGGGCTGCGCTGGCTTCTCCTGGTCGCTGTGCTCAAAGGTGTCCA
GTGTCAGTCGCTGGCGGAGTCCGGGGGTCGCCTGGTCACGCCTGGCACACCCC
TGACACTCACCTGCACAGCCTCTGGAATCGACCTCAGTAGCTATGCAATGGGC
TGGGTCCGCCAGGCTCCAGGGAAGGGGCTGGAATACATCGGATTCATTTATGC
TAGTGGCAGTATATTCTACGCGAGCTGGGCGAAAGGCCGATTCACCATCTCCA
AAACCTCGTCGACCACGGTGGATCTGAAAATGACCAGCCTGACAACCGAGGAC
ACGGCCACCTATTTCTGTGCCAGAGCGGGATATTATTTTGGTGGTAATTATGA
TCTTAACTTGTGGGGCCAAGGCACCCTGGTCACCGTCTCTTCA Heavy chain variable region amino acid sequence (SEQ ID NO. 3)    (SEQ ID NO. 6)
METGLRWLLLVAVLKGVQCQSLAESGGRLVTPGTPLTLTCTASGIDLSSYAMG
WVRQAPGKGLEYIGFIYASGSIFYASWAKGRFTISKTSSTTVDLKMTSLTTED
TATYFCARAGYYFGGNYDLNLWGQGTLVTVSS ——— (SEQ ID NO. 7)
——— (SEQ ID NO. 8)

Light chain variable region nucleic acid sequence (SEQ ID NO. 4)
ATGGACACGAGGGCCCCCACTCAGCTGCTGGGGCTCCTGCTGCTCTGGCTCCC
AGGTGCCAGATGTGCTGACATTGTGCTGACCCAGACTCCAGCCTCGGTGGAGG
TAGCTGTGGGAGGCACAGTCACCATCAAGTGCCAGGCCAGTCAGAGCATTAGT
AATTACTTAGCCTGGTATCAGCGGAAACCAGGGCAGCCTCCCAGGCTCCTGAT
CTACAGGGCATCCACTCTGGCATCTGGGGTCTCATCGCGGTTCAAAGGCAGTG
GATCTGGGACACAGTTCACTCTCACCATCAGCGGCGTGGAGTGTGCCGATGCT
GCCACTTACTACTGTCAACAGGGTTATGTCAGTAATAATCTTGATAATATTTT
CGGCGGAGGGACCGAGGTGGTGGTCAAA Light chain variable region amino acid sequence (SEQ ID NO. 5)    (SEQ ID NO. 9)
MDTRAPTQLLGLLLLWLPGARCADIVLTQTPASVEVAVGGTVTIKCQASQSIS
NYLAWYQRKPGQPPRLLIYRASTLASGVSSRFKGSGSGTQFTLTISGVECADA
ATYYCQQGYVSNNLDNIFGGGTEVVVK ——— (SEQ ID NO. 10)
——— (SEQ ID NO. 11)

FIG. 2

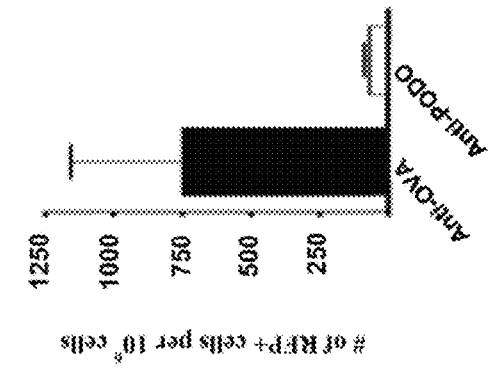
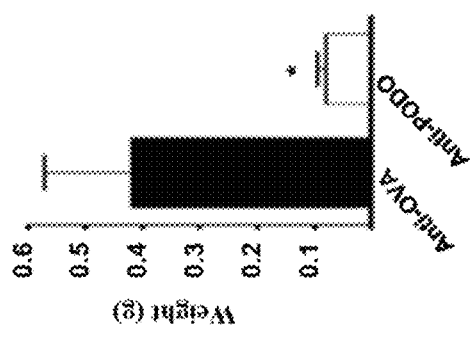
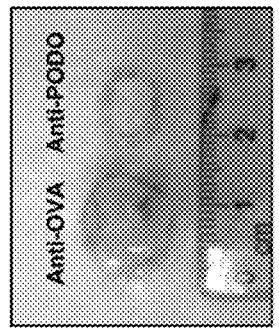
FIG. 6A  FIG. 6B  FIG. 6C
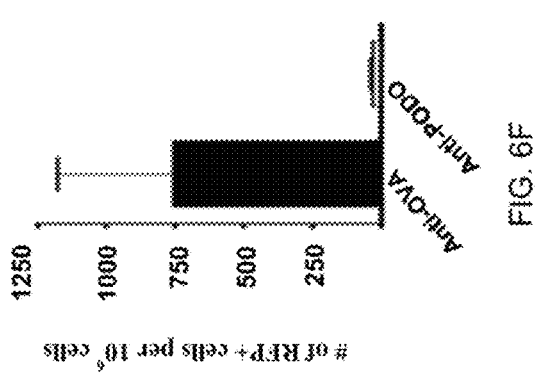
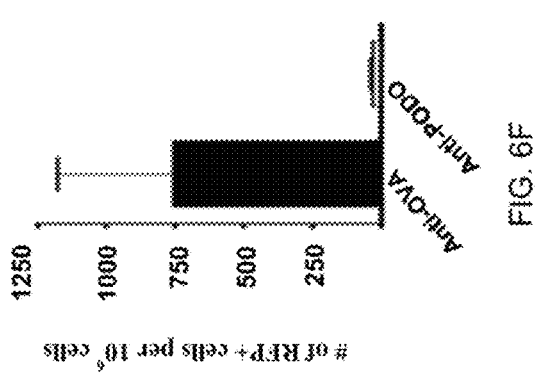
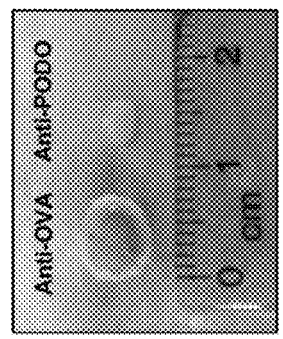
FIG. 6D  FIG. 6E  FIG. 6F

A. Podo_83_original_light_nucleotide_sequence (SEQ ID NO: 75)
GAATTCGCCACCATGGACACGAGGGCCCCCACTCAGCTCTTGGGTCTCCTGCTGCTCTGGCTCCCAGGTGCCAGATGTG
CTGACATTGTGCTGACCCAGACTCCACTCCAGCCTGTGGTGAGGCTAGTGTGGGAGGCACAGTCACCATCAAGTGCCAGGCCA
GTCAGAGCATTAGTAATTACTTAGCCTGGTATCAGCAGAAACCAGGGCAGCCTCCAGGTCTGATCTACAGGGCATC
CACTCTGGCATCTGGGGTCATCGCGGTTCAAACGCAGTGCAGTTGGGACACAGTTGGGATCCACTCTCACCATCAGCGCGTG
GAGTGTGCCGATGCTGCCACTTACTACTGTGTCAACAGGGTTATGTCAGTACTATAATCTGATAATATTTCGGAGGGA
CCGAGGTGGTGGTCAAACGTACG B. Podo_83_original_light_amino_acid_sequence (SEQ ID NO: 5)
MDTRAPTQLLGLLLLWLPGARCADIVLIQTPASVEVAVGGTVTIKCQASQSISNYLAWYQRKPGQPPRLLIYRASTLASGVS
SRFKGSGSGTQFTLTISGVECADAATYYCQQGYVSNNLDNIFGGGTEVVK C. Podo_83_humanized_light_ver_1_nucleotide_sequence (SEQ ID NO: 32)
TTTAAACGGATCTCTAGCGAATTCGCCACCATGGACATGCGCGTGCCAGCGCAGTCTGCTGGCCTGCTCTGCTGGC
TCCCAGACACCGGTGCCACATCAAATGACCCAGTCCCATCTGAGTCGCATCTGTGTCGGCGATAGGGTCACCAT
CACATGTCAGGCTCCCAGTCCCAGTATAATCTCGCTTGGTACCAGCAGCAGAAGCAGGGCACAGATTCACTCTGA
ATCTACCGGCTTCCACTCTCCTCAGCCTGAGGACGTGCTACTATTGCCAACAGGGCTACGTGTCTAATAACCTGGACAATAT
CTATCTCCTCGGAGGCGGGACCGAGGTGGTCAAACGTACGGTTGCTGGCACCATCGTCTT D. Podo_83_humanized_light_ver_1_amino_acid_sequence (SEQ ID NO: 33)
MDMRVPAQLLGLLLLWLPDTRCDIQMTQSPSSLSASVGDRVTITCQASQSISNYLAWYQQKPGKVPKLLIYRASTLASGVPS
RFSGSGSGTDFTLTISSLQPEDVATYYCQQGYVSNNLDNIFGGGTEVVK E. Podo_83_original_nucleotide_sequence (SEQ ID NO: 76)
GAATTCCACCATGGAGACTGGAGACTGGGCTGCGCTGGCTTCCTGGTCTGGTCGCTTGTCAAAGGTGTCAGTGTCCAGGTGTCGCTGCG
GAGTCCGGAGTGGTGGCTGCACCTGGTCACACCTCACTGCACCTGGAATGGACCTGAGCTAGCTG
ATGCAATGGGCTGGGCTTCCAGGGAAGGGGCTGGAATACATGGATTCATTAGCTAGTGGCAGTATATT
CTACGCGAGCTGGGCACGGCCGAAAGGCCGATTCACCATCTCCAAAACCTGTGACCACCGGTGGATCTGAAAATGACCAGCCT
GACAACGACGGACACGGCCACTTCTGGTCCAGAGCGGGGATATTATTGGTGTTAATTATGATCTTAACTGTGTGG
GGCCAAGGCACCCTGGTCACCGTCTCCTCAGCTAGC FIG. 10 (continued)

F. Podo_83_original_amino_acid_sequence (SEQ ID NO: 3)
METGLRWLLVAVLKGVQCQSLAESGGRLVTPGTPLTLTCTASGIDLSSYAMGWVRQAPGKGLEYIGFIYASGSIFYASWAK
GRFTISKTSSTTVDLKMTSLTTEDTATYFCARAGYYFGGNYDLNLWGQGTLVTVSS G. Podo_83_humanized_ver_1_nucleotide_sequence (SEQ ID NO: 34)
AAGTTAAACGGATCTCTAGCGAATTCGCCACCATGGAGTTTGGTTGTCCTGGTGTTCCTGGTGGCAATCCTCAAAG
GGGTGCAATGCCAGTCCAGTCCTGTGGAGAGCGGGGGCGGCGACTGGTCCTTGAGGCTCTGAGCTGTG
CTGCCTCTGGCATTGATCTGTCCTCTTATGCCATGGGTTGGGTCCGCCAAGGTCTCGAGTGGGTGAG
CTTTATTTAGGCTCTGGCTCATCTGGGCATCTGGCGAAGGGGCGTTCACCATCAGTAGGACAACTCTAAG
AATACCTTGTATCTGCAGATGAACTCTCTGCGAGATACCGCTGTGTATTACTGCGCGCAGGCTACTATT
TCGGCGGAAATTACGATCTCAATCTCTGGGCCCAGGGCCAGGCACCGTGTCCTGCTAGCACCAAGGCCATC
GGTCTTC H. Podo_83_humanized_ver_1_amino_acid_sequence (SEQ ID NO: 35)
MEFGLSWVFLVAILKGVQCEVQLVESGGGLVQPGGSLRLSCAASGIDLSSYAMGWVRQAPGKGLEWVSFIYAS
WAKGRFTISRDNSKNTLYLQMNSLRAEDTAVYYCARAGYYFGGNYDLNLWGQGTLVTVSS I. Podo_83_humanized_ver_2_nucleotide_sequence (SEQ ID NO: 36)
AAGTTAAACGGATCTCTAGCGAATTCGCCACCATGGAGTTTGGTTGTCCTGGTGTTCCTGGTGGCAATCCTCAAAG
GGGTGCAATGCCAGTCCAGTCCTGTGGAGAGCGGGGGCGGCGACTGGTCCTTGCAGGTCCTGAGCTGTG
CTGCCTCTGGCATTGATCTGTCCTCTTATGCCATGGGTTGGGTCCGCCAAGGGCTCGAGTGGGTGAG
CTTTATTTAGGCTCTGGCTCATCTGGGCATCTGGCGAAGGGGCGTTCACCATCAGTAGGACAACTCTAATA
CCTTGTATCTGCAGATGAACTCTCTGCGAGATACCGCTGTGTATTACTGCGCGCAGGCTACTATTTCGG
CGGAAATTACGATCTCAATCTCTGGGCCCAGGGCCAGGCACCGTGTCCTGCTAGCACCAAGGCCCATCGGTC
TTC J. Podo_83_humanized_ver_2_amino_acid_sequence (SEQ ID NO: 37)
MEFGLSWVFLVAILKGVQCEVQLVESGGGLVQPGGSLRLSCAASGIDLSSYAMGWVRQAPGKGLEWVSFIYASGSIFYASW
AKGRFTISRDNSNTLYLQMNSLRAEDTAVYYCARAGYYFGGNYDLNLWGQGTLVTVSS

FIG. 11

A.  Podo83rabbit_VH_NT (SEQ ID NO: 2)
*ATGGAGACTGGGCTGCGCTGGCTTCTCCTGGTCGCTGTGCTCAAAGGTGTCCAGTGT*CAGTCGCTGGCGGAGTCC
GGGGGTCGCCTGGTCACGCCTGGCACACCCCTGACACTCACCTGCACAGCCTCTGGAATCGACCTCAGTAGCTATG
CAATGGGCTGGGTCCGCCAGGCTCCAGGGAAGGGGCTGGAATACATCGGATTCATTTATGCTAGTGGCAGTATAT
TCTACGCGAGCTGGGCGAAAGGCCGATTCACCATCTCCAAAACCTCGTCGACCACGGTGGATCTGAAAATGACCA
GCCTGACAACCGAGGACACGGCCACCTATTTCTGTGCCAGAGCGGGATATTATTTTGGTGGTAATTATGATCTTAA
CTTGTGGGGCCAAGGCACCCTGGTCACCGTCTCTTCA B.  Podo83rabbit_VH_AA (SEQ ID NO: 3)
*METGLRWLLLVAVLKGVQC*QSLAESGGRLVTPGTPLTLTCTASGIDLSSYAMGWV
RQAPGKGLEYIGFIYASGSIFYASWAKGRFTISKTSSTTVDLKMTSLTTEDTATYFC
ARAGYYFGGNYDLNLWGQGTLVTVSS C.  Podo83rabbit_Vk_NT (SEQ ID NO: 4)
*ATGGACACGAGGGCCCCCACTCAGCTGCTGGGGCTCCTGCTGCTCTGGCTCCCAGGTGCCAGATGTGCT*GACATTG
TGCTGACCCAGACTCCAGCCTCGGTGGAGGTAGCTGTGGGAGGCACAGTCACCATCAAGTGCCAGGCCAGTCAG
AGCATTAGTAATTACTTAGCCTGGTATCAGCGGAAACCAGGGCAGCCTCCCAGGCTCCTGATCTACAGGGCATCCA
CTCTGGCATCTGGGGTCTCATCGCGGTTCAAAGGCAGTGGATCTGGGACACAGTTCACTCTCACCATCAGCGGCGT
GGAGTGTGCCGATGCTGCCACTTACTACTGTCAACAGGGTTATGTCAGTAATAATCTTGATAATATTTTCGGCGGA
GGGACCGAGGTGGTGGTCAAA D.  Podo83rabbit_VK_AA (SEQ ID NO: 5)
*MDTRAPTQLLGLLLLWLPGARCA*DIVLTQTPASVEVAVGGTVTIKCQASQSISNYL
AWYQRKPGQPPRLLIYRASTLASGVSSRFKGSGSGTQFTLTISGVECADAATYYCQ
QGYVSNNLDNIFGGGTEVVVK E.  Podo83hum_VH1_NT (SEQ ID NO: 77)
*ATGGAGTTTGGTTTGTCCTGGGTGTTCCTGGTGGCAATCCTCAAAGGGGTGCAATGC*GAGGTCCAGCTGGTGGAG
AGCGGGGGCGGACTGGTGCAGCCTGGAGGGTCCTTGAGGCTGAGCTGTGCTGCCTCTGGCATTGATCTGTCCTCT
TATGCCATGGGTTGGGTCCGCCAGGCCCCCGGCAAGGGTCTCGAGTGGGTGAGCTTTATTTACGCCTCTGGCTCC
ATCTTCTACGCATCTTGGGCGAAGGGGCGCTTCACCATCAGTAGGGACAACTCTAAGAATACCTTGTATCTGCAGA
TGAACTCCCTGCGGGCCGAAGATACCGCTGTGTATTACTGCGCCCCGGGCAGGCTACTATTTCGGCGGAAATTACG
ATCTCAATCTCTGGGGCCAGGGCACACTGGTGACCGTGTCCTCT F.  Podo83hum_VH1_AA (SEQ ID NO: 35)
*MEFGLSWVFLVAILKGVQC*EVQLVESGGGLVQPGGSLRLSCAASGIDLSSYAMGW
VRQAPGKGLEWVSFIYASGSIFYASWAKGRFTISRDNSKNTLYLQMNSLRAEDTAV
YYCARAGYYFGGNYDLNLWGQGTLVTVSS G.  Podo83hum_VH2_NT (SEQ ID NO: 78)
*ATGGAGTTTGGTTTGTCCTGGGTGTTCCTGGTGGCAATCCTCAAAGGGGTGCAATGC*GAGGTCCAGCTGGTGGAG
AGCGGGGGCGGACTGGTGCAGCCTGGAGGGTCCTTGAGGCTGAGCTGTGCTGCCTCTGGCATTGATCTGTCCTCT
TATGCCATGGGTTGGGTCCGCCAGGCCCCCGGCAAGGGTCTCGAGTGGGTGAGCTTTATTTACGCCTCTGGCTCC
ATCTTCTACGCATCTTGGGCGAAGGGGCGCTTCACCATCAGTAGGGACAACTCTAATACCTTGTATCTGCAGATGA FIG. 11 (continued)

ACTCCCTGCGGGCCGAAGATACCGCTGTGTATTACTGCGCCCGGGCAGGCTACTATTTCGGCGGAAATTACGATCT
CAATCTCTGGGGCCAGGGCACACTGGTGACCGTGTCCTCT

H.  Podo83hum_VH2_AA (SEQ ID NO: 37)
<u>MEFGLSWVFLVAILKGVQ</u>CEVQLVESGGGLVQPGGSLRLSCAASGIDLSSYAMGW
VRQAPGKGLEWVSFIYASGSIFYASWAKGRFTISRDNSNTLYLQMNSLRAEDTAVY
YCARAGYYFGGNYDLNLWGQGTLVTSS I.  Podo83hum_Vk_NT (SEQ ID NO: 79)
<u>ATGGACATGCGCGTGCCAGCGCAGCTGCTGGGCCTGCTCCTCCTGTGGCTCCCAGACACCCGTTGC</u>GACATTCAAA
TGACCCAGTCCCCATCCAGTCTGAGTGCGTCTGTCGGCGATAGGGTCACCATCACATGTCAGGCTTCCCAGTCCAT
TTCCAATTATCTCGCTTGGTACCAGCAGAAGCCTGGAAAGGTGCCCAAACTGTTGATCTACCGCGCTTCCACTCTCG
CTAGTGGCGTGCCCTCCCGGTTTAGCGGCAGCGGAAGCGGCACAGATTTCACTCTGACTATCTCCTCCCTGCAGCC
TGAGGACGTGGCTACCTACTATTGCCAACAGGGCTACGTGTCTAATAACCTGGACAATATCTTTGGAGGCGGGAC
CGAGGTCGTGGTCAAG J.  Podo83hum_VK_AA (SEQ ID NO: 33)
<u>MDMRVPAQLLGLLLLWLPDTRC</u>DIQMTQSPSSLSASVGDRVTITCQASQSISNYLA
WYQQKPGKVPKLLIYRASTLASGVPSRFSGSGSGTDFTLTISSLQPEDVATYYCQQ
GYVSNNLDNIFGGGTEVVVK

FIG. 12

A.    mPodo_3G2_vH_AA  (SEQ ID NO: 39)
*MGWSWIFLLSGTAGVHS*EVQLQQSGPELVKPGASVKMSCKASGYTFTSYVMHWV
KQKPGQGLEWIGYIHPYNDGTNYNEKFKGKATLTSDKSSNTAYMELSSLTSEDSAV
YYCARSWDWYFDVWGAGTTVTVSS B.    mPodo_3G2_vH_NT  (SEQ ID NO: 38)
*ATGGGATGGAGCTGGATCTTTCTCCTGTCAGGAACTGCAGGTGTCCACTCT*GAGGTCCAGCTGCAGCAGTCTGGAC
CTGAACTGGTAAAGCCTGGGGCTTCAGTGAAGATGTCCTGCAAGGCTTCTGGATACACATTCACTAGCTATGTTAT
GCACTGGGTGAAGCAGAAGCCTGGGCAGGGCCTTGAGTGGATTGGATATATTCATCCTTACAATGATGGTACTAA
TTACAATGAGAAGTTCAAAGGCAAGGCCACACTGACTTCAGACAAATCGTCCAACACAGCCTACATGGAACTCAG
CAGCCTGACCTCTGAGGACTCTGCGGTCTATTACTGTGCAAGATCATGGGACTGGTACTTCGATGTCTGGGGCGCA
GGGACCACGGTCACCGTCTCCTCA C.    mPodo_3G2_vk_AA  (SEQ ID NO: 41)
*MDFQVQIFSFLLISASVIISRG*QIVLTQSPAIMSASPGEKVTMTCSANSNVRYIHWH
QQKSGTSPKRWIYDTSKLSSGVPARFSGSGSGTSYSLTISNMEAEDAATYYCQQWI
SNPLTFGAGTKLELK D.    mPodo_3G2_vk_NT  (SEQ ID NO: 40)
*ATGGATTTTCAGGTGCAGATTTTCAGCTTCCTGCTAATCAGTGCCTCAGTCATAATATCCAGAGGA*CAAATTGTTCT
CACCCAGTCTCCAGCAATCATGTCTGCATCTCCAGGGGAGAAGGTCACCATGACCTGCAGTGCCAACTCAAATGTA
AGATACATTCACTGGCACCAGCAGAAGTCAGGCACCTCCCCCAAAAGATGGATTTATGACACATCCAAACTGTCTT
CTGGAGTCCCTGCTCGCTTCAGTGGCAGTGGGTCTGGGACCTCTTACTCTCTCACAATCAGCAACATGGAGGCTGA
AGATGCTGCCACTTATTACTGCCAGCAGTGGATTAGTAACCCACTCACGTTCGGTGCTGGGACCAAGCTGGAGCTG
AAA

SEQUENCE LISTING

<160> NUMBER OF SEQ ID NOS: 79

<210> SEQ ID NO 1
<211> LENGTH: 558
<212> TYPE: PRT
<213> ORGANISM: Homo sapiens

<400> SEQUENCE: 1

```
Met Arg Cys Ala Leu Ala Leu Ser Ala Leu Leu Leu Leu Leu Ser Thr
1               5                   10                  15

Pro Pro Leu Leu Pro Ser Ser Pro Ser Pro Ser Pro Ser Pro Ser Gln
            20                  25                  30

Asn Ala Thr Gln Thr Thr Thr Asp Ser Ser Asn Lys Thr Ala Pro Thr
                35                  40                  45

Pro Ala Ser Ser Val Thr Ile Met Ala Thr Asp Thr Ala Gln Gln Ser
    50                  55                  60

Thr Val Pro Thr Ser Lys Ala Asn Glu Ile Leu Ala Ser Val Lys Ala
65                  70                  75                  80

Thr Thr Leu Gly Val Ser Ser Asp Ser Pro Gly Thr Thr Leu Ala
                85                  90                  95

Gln Gln Val Ser Gly Pro Val Asn Thr Thr Val Ala Arg Gly Gly Gly
            100                 105                 110

Ser Gly Asn Pro Thr Thr Thr Ile Glu Ser Pro Lys Ser Thr Lys Ser
            115                 120                 125

Ala Asp Thr Thr Thr Val Ala Thr Ser Thr Ala Thr Ala Lys Pro Asn
            130                 135                 140

Thr Thr Ser Ser Gln Asn Gly Ala Glu Asp Thr Thr Asn Ser Gly Gly
145                 150                 155                 160

Lys Ser Ser His Ser Val Thr Thr Asp Leu Thr Ser Thr Lys Ala Glu
                165                 170                 175

His Leu Thr Thr Pro His Pro Thr Ser Pro Leu Ser Pro Arg Gln Pro
            180                 185                 190

Thr Ser Thr His Pro Val Ala Thr Pro Thr Ser Ser Gly His Asp His
            195                 200                 205

Leu Met Lys Ile Ser Ser Ser Ser Thr Val Ala Ile Pro Gly Tyr
210                 215                 220

Thr Phe Thr Ser Pro Gly Met Thr Thr Thr Leu Glu Thr Val Phe
225                 230                 235                 240

His His Val Ser Gln Ala Gly Leu Glu Leu Leu Thr Ser Gly Asp Leu
                245                 250                 255

Pro Thr Leu Ala Ser Gln Ser Ala Gly Ile Thr Ala Ser Ser Val Ile
            260                 265                 270

Ser Gln Arg Thr Gln Gln Thr Ser Ser Gln Met Pro Ala Ser Ser Thr
            275                 280                 285

Ala Pro Ser Ser Gln Glu Thr Val Gln Pro Thr Ser Pro Ala Thr Ala
            290                 295                 300

Leu Arg Thr Pro Thr Leu Pro Glu Thr Met Ser Ser Ser Pro Thr Ala
305                 310                 315                 320

Ala Ser Thr Thr His Arg Tyr Pro Lys Thr Pro Ser Pro Thr Val Ala
                325                 330                 335

His Glu Ser Asn Trp Ala Lys Cys Glu Asp Leu Glu Thr Gln Thr Gln
            340                 345                 350

Ser Glu Lys Gln Leu Val Leu Asn Leu Thr Gly Asn Thr Leu Cys Ala
            355                 360                 365
```

Gly Gly Ala Ser Asp Glu Lys Leu Ile Ser Leu Ile Cys Arg Ala Val
            370                 375                 380

Lys Ala Thr Phe Asn Pro Ala Gln Asp Lys Cys Gly Ile Arg Leu Ala
385                 390                 395                 400

Ser Val Pro Gly Ser Gln Thr Val Val Lys Glu Ile Thr Ile His
                405                 410                 415

Thr Lys Leu Pro Ala Lys Asp Val Tyr Glu Arg Leu Lys Asp Lys Trp
            420                 425                 430

Asp Glu Leu Lys Glu Ala Gly Val Ser Asp Met Lys Leu Gly Asp Gln
                435                 440                 445

Gly Pro Pro Glu Glu Ala Glu Asp Arg Phe Ser Met Pro Leu Ile Ile
450                 455                 460

Thr Ile Val Cys Met Ala Ser Phe Leu Leu Val Ala Ala Leu Tyr
465                 470                 475                 480

Gly Cys Cys His Gln Arg Leu Ser Gln Arg Lys Asp Gln Arg Leu
                485                 490                 495

Thr Glu Glu Leu Gln Thr Val Glu Asn Gly Tyr His Asp Asn Pro Thr
                500                 505                 510

Leu Glu Val Met Glu Thr Ser Ser Glu Met Gln Glu Lys Lys Val Val
            515                 520                 525

Ser Leu Asn Gly Glu Leu Gly Asp Ser Trp Ile Val Pro Leu Asp Asn
530                 535                 540

Leu Thr Lys Asp Asp Leu Asp Glu Glu Asp Thr His Leu
545                 550                 555

<210> SEQ ID NO 2
<211> LENGTH: 414
<212> TYPE: DNA
<213> ORGANISM: Artificial Sequence
<220> FEATURE:
<223> OTHER INFORMATION: Description of Artificial Sequence: Synthetic
      nucleic acid sequence for the heavy chain variable region
      anti-podocalyxin antibody

<400> SEQUENCE: 2
atggagactg ggctgcgctg gcttctcctg gtcgctgtgc tcaaaggtgt ccagtgtcag      60
tcgctggcgg agtccggggg tcgcctggtc acgcctggca cacccctgac actcacctgc    120
acagcctctg gaatcgacct cagtagctat gcaatgggct gggtccgcca ggctccaggg    180
aaggggctgg aatacatcgg attcatttat gctagtggca gtatattcta cgcgagctgg    240
gcgaaaggcc gattcaccat ctccaaaacc tcgtcgacca cggtggatct gaaaatgacc    300
agcctgacaa ccgaggacac ggccacctat ttctgtgcca gagcgggata ttattttggt    360
ggtaattatg atcttaactt gtggggccaa ggcaccctgg tcaccgtctc ttca          414

<210> SEQ ID NO 3
<211> LENGTH: 138
<212> TYPE: PRT
<213> ORGANISM: Artificial Sequence
<220> FEATURE:
<223> OTHER INFORMATION: Description of Artificial Sequence: Synthetic
      amino acid sequence for the heavy chain variable region
      anti-podocalyxin antibody

<400> SEQUENCE: 3

Met Glu Thr Gly Leu Arg Trp Leu Leu Leu Val Ala Val Leu Lys Gly
1               5                   10                  15

Val Gln Cys Gln Ser Leu Ala Glu Ser Gly Gly Arg Leu Val Thr Pro
            20                  25                  30

Gly Thr Pro Leu Thr Leu Thr Cys Thr Ala Ser Gly Ile Asp Leu Ser
            35                  40                  45

Ser Tyr Ala Met Gly Trp Val Arg Gln Ala Pro Gly Lys Gly Leu Glu
        50                  55                  60

Tyr Ile Gly Phe Ile Tyr Ala Ser Gly Ser Ile Phe Tyr Ala Ser Trp
65                  70                  75                  80

Ala Lys Gly Arg Phe Thr Ile Ser Lys Thr Ser Ser Thr Thr Val Asp
                85                  90                  95

Leu Lys Met Thr Ser Leu Thr Thr Glu Asp Thr Ala Thr Tyr Phe Cys
            100                 105                 110

Ala Arg Ala Gly Tyr Tyr Phe Gly Gly Asn Tyr Asp Leu Asn Leu Trp
        115                 120                 125

Gly Gln Gly Thr Leu Val Thr Val Ser Ser
    130                 135

<210> SEQ ID NO 4
<211> LENGTH: 399
<212> TYPE: DNA
<213> ORGANISM: Artificial Sequence
<220> FEATURE:
<223> OTHER INFORMATION: Description of Artificial Sequence: Synthetic
      nucleic acid sequence for the light chain variable region
      anti-podocalyxin antibody

<400> SEQUENCE: 4
atggacacga gggcccccac tcagctgctg gggctcctgc tgctctggct cccaggtgcc    60
agatgtgctg acattgtgct gacccagact ccagcctcgg tggaggtagc tgtgggaggc   120
acagtcacca tcaagtgcca ggccagtcag agcattagta attacttagc ctggtatcag   180
cggaaaccag gcagcctcc caggctcctg atctacaggg catccactct ggcatctggg   240
gtctcatcgc ggttcaaagg cagtggatct gggacacagt tcactctcac catcagcggc   300
gtggagtgtg ccgatgctgc cacttactac tgtcaacagg ttatgtcag taataatctt   360 gataatattt tcggcggagg gaccgaggtg gtggtcaaa                          399

<210> SEQ ID NO 5
<211> LENGTH: 133
<212> TYPE: PRT
<213> ORGANISM: Artificial Sequence
<220> FEATURE:
<223> OTHER INFORMATION: Description of Artificial Sequence: Synthetic
      amino acid sequence for the light chain variable region
      anti-podocalyxin antibody

<400> SEQUENCE: 5

Met Asp Thr Arg Ala Pro Thr Gln Leu Leu Gly Leu Leu Leu Leu Trp
1               5                   10                  15

Leu Pro Gly Ala Arg Cys Ala Asp Ile Val Leu Thr Gln Thr Pro Ala
            20                  25                  30

Ser Val Glu Val Ala Val Gly Gly Thr Val Thr Ile Lys Cys Gln Ala
        35                  40                  45

Ser Gln Ser Ile Ser Asn Tyr Leu Ala Trp Tyr Gln Arg Lys Pro Gly
    50                  55                  60

Gln Pro Pro Arg Leu Leu Ile Tyr Arg Ala Ser Thr Leu Ala Ser Gly
65                  70                  75                  80

Val Ser Ser Arg Phe Lys Gly Ser Gly Ser Gly Thr Gln Phe Thr Leu
                85                  90                  95

Thr Ile Ser Gly Val Glu Cys Ala Asp Ala Ala Thr Tyr Tyr Cys Gln

```
                100             105             110
Gln Gly Tyr Val Ser Asn Asn Leu Asp Asn Ile Phe Gly Gly Gly Thr
        115                 120             125

Glu Val Val Val Lys
    130

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 83 (Ab-1) VH CDR1

<400> SEQUENCE: 6

Ser Tyr Ala Met Gly
1               5

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 83 (Ab-1) VH CDR2

<400> SEQUENCE: 7

Phe Ile Tyr Ala Ser Gly Ser Ile Phe Tyr Ala Ser Trp Ala Lys Gly
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 83 (Ab-1) VH CDR3

<400> SEQUENCE: 8

Ala Gly Tyr Tyr Phe Gly Gly Asn Tyr Asp Leu Asn Leu
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 83 (Ab-1) Vk CDR1

<400> SEQUENCE: 9

Gln Ala Ser Gln Ser Ile Ser Asn Tyr Leu Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 83 (Ab-1) Vk CDR2

<400> SEQUENCE: 10

Arg Ala Ser Thr Leu Ala Ser
1               5
```

```
<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 83 (Ab-1) Vk CDR3

<400> SEQUENCE: 11

Gln Gln Gly Tyr Val Ser Asn Asn Leu Asp Asn Ile
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 83 (Ab-1) VH CDR1

<400> SEQUENCE: 12

Gly Ile Asp Leu Ser Ser Tyr Ala Met Gly
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 83 (Ab-1) VH CDR1

<400> SEQUENCE: 13

Gly Ile Asp Leu Ser Ser Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 83 (Ab-1) VH CDR2

<400> SEQUENCE: 14

Phe Ile Tyr Ala Ser Gly Ser Ile
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 83 (Ab-1) VH CDR2

<400> SEQUENCE: 15

Ile Tyr Ala Ser Gly Ser Ile
1               5

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 83 (Ab-1) VH CDR3

<400> SEQUENCE: 16
```

```
Ala Arg Ala Gly Tyr Tyr Phe Gly Gly Asn Tyr Asp Leu Asn Leu
1               5                   10                  15

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 83 (Ab-1) Vk CDR1

<400> SEQUENCE: 17

Gln Ser Ile Ser Asn Tyr
1               5

<210> SEQ ID NO 18
<211> LENGTH: 3
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 83 (Ab-1) Vk CDR2

<400> SEQUENCE: 18

Arg Ala Ser
1

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 3G2 VH CDR1

<400> SEQUENCE: 19

Ser Tyr Val Met His
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 3G2 VH CDR1

<400> SEQUENCE: 20

Gly Tyr Thr Phe Thr Ser Tyr Val Met His
1               5                   10

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 3G2 VH CDR1

<400> SEQUENCE: 21

Gly Tyr Thr Phe Thr Ser Tyr Val
1               5

<210> SEQ ID NO 22
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      Anti-Podocalyxin Antibody 3G2 VH CDR2

<400> SEQUENCE: 22

Tyr Ile His Pro Tyr Asn Asp Gly Thr Asn Tyr Asn Glu Lys Phe Lys
1               5                   10                  15

Gly

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 3G2 VH CDR2

<400> SEQUENCE: 23

Tyr Ile His Pro Tyr Asn Asp Gly Thr
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 3G2 VH CDR2

<400> SEQUENCE: 24

Ile His Pro Tyr Asn Asp Gly Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 3G2 VH CDR3

<400> SEQUENCE: 25

Ser Trp Asp Trp Tyr Phe Asp Val
1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 3G2 VH CDR3

<400> SEQUENCE: 26

Ala Arg Ser Trp Asp Trp Tyr Phe Asp Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 3G2 Vk CDR1

<400> SEQUENCE: 27

Ser Ala Asn Ser Asn Val Arg Tyr Ile His
```

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 3G2 Vk CDR1

<400> SEQUENCE: 28

Ser Asn Val Arg Tyr
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 3G2 Vk CDR2

<400> SEQUENCE: 29

Asp Thr Ser Lys Leu Ser Ser
1               5

<210> SEQ ID NO 30
<211> LENGTH: 3
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 3G2 Vk CDR2

<400> SEQUENCE: 30

Asp Thr Ser
1

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      Anti-Podocalyxin Antibody 3G2 Vk CDR3

<400> SEQUENCE: 31

Gln Gln Trp Ile Ser Asn Pro Leu Thr
1               5

<210> SEQ ID NO 32
<211> LENGTH: 452
<212> TYPE: DNA
<213> ORGANISM: Artificial Sequence
<220> FEATURE:
<223> OTHER INFORMATION: Description of Artificial Sequence: Synthetic
      humanized light chain variable nucleotide sequence
      Podo_83_humanized_light_ver_1_nucleotide_sequence

<400> SEQUENCE: 32
tttaaacgga tctctagcga attcgccacc atggacatgc gcgtgccagc gcagctgctg     60
ggcctgctcc tcctgtgggc tcccagacac ccgttgcgac attcaaatga ccagtcccca    120
tccagtctga gtgcgtctgt cggcgatagg gtcaccatca catgtcaggc ttcccagtcc    180
atttccaatt atctcgcttg gtaccagcag aagcctggaa aggtgccaa  actgttgatc    240 taccgcgctt ccactctcgc tagtggcgtg ccctcccggt ttagcggcag cggaagcggc    300

```
acagatttca ctctgactat ctcctccctg cagcctgagg acgtggctac ctactattgc    360
caacagggct acgtgtctaa taacctggac aatatctttg gaggcgggac cgaggtcgtg    420
gtcaagcgta cggtggctgc accatctgtc tt                                  452
```

```
<210> SEQ ID NO 33
<211> LENGTH: 132
<212> TYPE: PRT
<213> ORGANISM: Artificial Sequence
<220> FEATURE:
<223> OTHER INFORMATION: Description of Artificial Sequence: Synthetic
      humanized light chain variable amino acid sequence
      Podo_83_humanized_light_ver_1_amino_acid_sequence

<400> SEQUENCE: 33
```

Met Asp Met Arg Val Pro Ala Gln Leu Leu Gly Leu Leu Leu Leu Trp
1               5                   10                  15

Leu Pro Asp Thr Arg Cys Asp Ile Gln Met Thr Gln Ser Pro Ser Ser
            20                  25                  30

Leu Ser Ala Ser Val Gly Asp Arg Val Thr Ile Thr Cys Gln Ala Ser
        35                  40                  45

Gln Ser Ile Ser Asn Tyr Leu Ala Trp Tyr Gln Lys Pro Gly Lys
    50                  55                  60

Val Pro Lys Leu Leu Ile Tyr Arg Ala Ser Thr Leu Ala Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Val Ala Thr Tyr Tyr Cys Gln Gln
            100                 105                 110

Gly Tyr Val Ser Asn Asn Leu Asp Asn Ile Phe Gly Gly Gly Thr Glu
        115                 120                 125

Val Val Val Lys
    130

```
<210> SEQ ID NO 34
<211> LENGTH: 480
<212> TYPE: DNA
<213> ORGANISM: Artificial Sequence
<220> FEATURE:
<223> OTHER INFORMATION: Description of Artificial Sequence: Synthetic
      humanized heavy chain variable nucleotide sequence
      Podo_83_humanized_ver_1_nucleotide_sequence

<400> SEQUENCE: 34
aagtttaaac ggatctctag cgaattcgcc accatggagt ttgggtttgtc ctgggtgttc    60 ctggtggcaa tcctcaaagg ggtgcaatgc gaggtccagc tggtggagag cggggggcgga   120 ctggtgcagc ctggagggtc cttgaggctg agctgtgctg cctctggcat tgatctgtcc   180
tcttatgcca tgggttgggt ccgccaggcc cccggcaagg gtctcgagtg ggtgagcttt   240
atttacgcct ctggctccat cttctacgca tcttgggcga agggccgctt caccatcagt   300
agggacaact ctaagaatac cttgtatctg cagatgaact ccctgcgggc cgaagatacc   360
gctgtgtatt actgcgcccg ggcaggctac tatttcggcg aaattacga tctcaatctc   420 tggggccagg gcacactggt gaccgtgtcc tctgctagca ccaagggccc atcggtcttc   480
```

```
<210> SEQ ID NO 35
<211> LENGTH: 140
<212> TYPE: PRT
<213> ORGANISM: Artificial Sequence
```

<220> FEATURE:
<223> OTHER INFORMATION: Description of Artificial Sequence: Synthetic
humanized heavy chain variable amino acid sequence
Podo_83_humanized_ver_1_amino_acid_sequence

<400> SEQUENCE: 35

```
Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Ile Asp Leu
        35                  40                  45

Ser Ser Tyr Ala Met Gly Trp Val Arg Gln Ala Pro Gly Lys Gly Leu
    50                  55                  60

Glu Trp Val Ser Phe Ile Tyr Ala Ser Gly Ser Ile Phe Tyr Ala Ser
65                  70                  75                  80

Trp Ala Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Ala Gly Tyr Tyr Phe Gly Gly Asn Tyr Asp Leu Asn
        115                 120                 125

Leu Trp Gly Gln Gly Thr Leu Val Thr Val Ser Ser
    130                 135                 140
```

<210> SEQ ID NO 36
<211> LENGTH: 477
<212> TYPE: DNA
<213> ORGANISM: Artificial Sequence
<220> FEATURE:
<223> OTHER INFORMATION: Description of Artificial Sequence: Synthetic
humanized heavy chain variable nucleotide sequence
Podo_83_humanized_ver_2_nucleotide_sequence

<400> SEQUENCE: 36

```
aagtttaaac ggatctctag cgaattcgcc accatggagt ttggtttgtc ctgggtgttc      60
ctggtggcaa tcctcaaagg ggtgcaatgc gaggtccagc tggtggagag cggggggcgga    120
ctggtgcagc ctggagggtc cttgaggctg agctgtgctg cctctggcat tgatctgtcc    180
tcttatgcca tgggttgggt ccgccaggcc cccggcaagg gtctcgagtg ggtgagcttt    240
atttacgcct ctggctccat cttctacgca tcttgggcga agggggcgctt caccatcagt    300
agggacaact ctaatacctt gtatctgcag atgaactccc tgcgggccga agataccgct    360
gtgtattact gcgcccgggc aggctactat ttcggcggaa attacgatct caatctctgg    420
ggccagggca cactggtgac cgtgtcctct gctagcacca agggcccatc ggtcttc      477
```

<210> SEQ ID NO 37
<211> LENGTH: 139
<212> TYPE: PRT
<213> ORGANISM: Artificial Sequence
<220> FEATURE:
<223> OTHER INFORMATION: Description of Artificial Sequence: Synthetic
humanized heavy chain variable amino acid sequence
Podo_83_humanized_ver_2_amino_acid_sequence

<400> SEQUENCE: 37

```
Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30
```

Pro Gly Gly Ser Leu Arg Leu Ser Cys Ala Ala Ser Gly Ile Asp Leu
        35                  40                  45

Ser Ser Tyr Ala Met Gly Trp Val Arg Gln Ala Pro Gly Lys Gly Leu
    50                  55                  60

Glu Trp Val Ser Phe Ile Tyr Ala Ser Gly Ser Ile Phe Tyr Ala Ser
65                  70                  75                  80

Trp Ala Lys Gly Arg Phe Thr Ile Ser Arg Asp Asn Ser Asn Thr Leu
                85                  90                  95

Tyr Leu Gln Met Asn Ser Leu Arg Ala Glu Asp Thr Ala Val Tyr Tyr
            100                 105                 110

Cys Ala Arg Ala Gly Tyr Tyr Phe Gly Gly Asn Tyr Asp Leu Asn Leu
                115                 120                 125

Trp Gly Gln Gly Thr Leu Val Thr Val Ser Ser
        130                 135

<210> SEQ ID NO 38
<211> LENGTH: 402
<212> TYPE: DNA
<213> ORGANISM: Artificial Sequence
<220> FEATURE:
<223> OTHER INFORMATION: Description of Artificial Sequence: Synthetic
      VH nucleotide sequence mPodo_3G2_vH_NT

<400> SEQUENCE: 38
atgggatgga gctggatctt tctcctgtca ggaactgcag gtgtccactc tgaggtccag      60
ctgcagcagt ctggacctga actggtaaag cctggggctt cagtgaagat gtcctgcaag    120
gcttctggat acacattcac tagctatgtt atgcactggg tgaagcagaa gcctgggcag    180
ggccttgagt ggattggata tattcatcct tacaatgatg gtactaatta caatgagaag    240
ttcaaaggca aggccacact gacttcagac aaatcgtcca acacagccta catggaactc    300
agcagcctga cctctgagga ctctgcggtc tattactgtg caagatcatg ggactggtac    360
ttcgatgtct ggggcgcagg gaccacggtc accgtctcct ca                       402

<210> SEQ ID NO 39
<211> LENGTH: 134
<212> TYPE: PRT
<213> ORGANISM: Artificial Sequence
<220> FEATURE:
<223> OTHER INFORMATION: Description of Artificial Sequence: Synthetic
      VH amino acid sequence mPodo_3G2_vH_AA

<400> SEQUENCE: 39

Met Gly Trp Ser Trp Ile Phe Leu Leu Ser Gly Thr Ala Gly Val His
1               5                   10                  15

Ser Glu Val Gln Leu Gln Gln Ser Gly Pro Glu Leu Val Lys Pro Gly
            20                  25                  30

Ala Ser Val Lys Met Ser Cys Lys Ala Ser Gly Tyr Thr Phe Thr Ser
        35                  40                  45

Tyr Val Met His Trp Val Lys Gln Lys Pro Gly Gln Gly Leu Glu Trp
    50                  55                  60

Ile Gly Tyr Ile His Pro Tyr Asn Asp Gly Thr Asn Tyr Asn Glu Lys
65                  70                  75                  80

Phe Lys Gly Lys Ala Thr Leu Thr Ser Asp Lys Ser Ser Asn Thr Ala
                85                  90                  95

Tyr Met Glu Leu Ser Ser Leu Thr Ser Glu Asp Ser Ala Val Tyr Tyr
            100                 105                 110

```
Cys Ala Arg Ser Trp Asp Trp Tyr Phe Asp Val Trp Gly Ala Gly Thr
            115                 120                 125

Thr Val Thr Val Ser Ser
        130
```

<210> SEQ ID NO 40
<211> LENGTH: 384
<212> TYPE: DNA
<213> ORGANISM: Artificial Sequence
<220> FEATURE:
<223> OTHER INFORMATION: Description of Artificial Sequence: Synthetic
      Vk nucleotide sequence mPodo_3G2_vk_NT

<400> SEQUENCE: 40

```
atggattttc aggtgcagat tttcagcttc ctgctaatca gtgcctcagt cataatatcc     60
agaggacaaa ttgttctcac ccagtctcca gcaatcatgt ctgcatctcc aggggagaag    120
gtcaccatga cctgcagtgc caactcaaat gtaagataca ttcactggca ccagcagaag    180
tcaggcacct cccccaaaag atggatttat gacacatcca aactgtcttc tggagtccct    240
gctcgcttca gtggcagtgg gtctgggacc tcttactctc tcacaatcag caacatggag    300
gctgaagatg ctgccactta ttactgccag cagtggatta gtaacccact cacgttcggt    360
gctgggacca agctggagct gaaa                                            384
```

<210> SEQ ID NO 41
<211> LENGTH: 128
<212> TYPE: PRT
<213> ORGANISM: Artificial Sequence
<220> FEATURE:
<223> OTHER INFORMATION: Description of Artificial Sequence: Synthetic
      Vk amino acid sequence mPodo_3G2_vk_AA

<400> SEQUENCE: 41

```
Met Asp Phe Gln Val Gln Ile Phe Ser Phe Leu Leu Ile Ser Ala Ser
1               5                   10                  15

Val Ile Ile Ser Arg Gly Gln Ile Val Leu Thr Gln Ser Pro Ala Ile
            20                  25                  30

Met Ser Ala Ser Pro Gly Glu Lys Val Thr Met Thr Cys Ser Ala Asn
        35                  40                  45

Ser Asn Val Arg Tyr Ile His Trp His Gln Gln Lys Ser Gly Thr Ser
    50                  55                  60

Pro Lys Arg Trp Ile Tyr Asp Thr Ser Lys Leu Ser Ser Gly Val Pro
65                  70                  75                  80

Ala Arg Phe Ser Gly Ser Gly Ser Gly Thr Ser Tyr Ser Leu Thr Ile
                85                  90                  95

Ser Asn Met Glu Ala Glu Asp Ala Ala Thr Tyr Tyr Cys Gln Gln Trp
            100                 105                 110

Ile Ser Asn Pro Leu Thr Phe Gly Ala Gly Thr Lys Leu Glu Leu Lys
        115                 120                 125
```

<210> SEQ ID NO 42
<211> LENGTH: 526
<212> TYPE: PRT
<213> ORGANISM: Homo sapiens

<400> SEQUENCE: 42

```
Met Arg Cys Ala Leu Ala Leu Ser Ala Leu Leu Leu Leu Leu Ser Thr
1               5                   10                  15

Pro Pro Leu Leu Pro Ser Ser Pro Ser Pro Ser Pro Ser Pro Ser Gln
            20                  25                  30
```

```
Asn Ala Thr Gln Thr Thr Thr Asp Ser Ser Asn Lys Thr Ala Pro Thr
         35                  40                  45
Pro Ala Ser Ser Val Thr Ile Met Ala Thr Asp Thr Ala Gln Gln Ser
 50                  55                  60
Thr Val Pro Thr Ser Lys Ala Asn Glu Ile Leu Ala Ser Val Lys Ala
 65                  70                  75                  80
Thr Thr Leu Gly Val Ser Ser Asp Ser Pro Gly Thr Thr Thr Leu Ala
                 85                  90                  95
Gln Gln Val Ser Gly Pro Val Asn Thr Thr Val Ala Arg Gly Gly Gly
                100                 105                 110
Ser Gly Asn Pro Thr Thr Thr Ile Glu Ser Pro Lys Ser Thr Lys Ser
                115                 120                 125
Ala Asp Thr Thr Thr Val Ala Thr Ser Thr Ala Thr Ala Lys Pro Asn
                130                 135                 140
Thr Thr Ser Ser Gln Asn Gly Ala Glu Asp Thr Thr Asn Ser Gly Gly
145                 150                 155                 160
Lys Ser Ser His Ser Val Thr Thr Asp Leu Thr Ser Thr Lys Ala Glu
                165                 170                 175
His Leu Thr Thr Pro His Pro Thr Ser Pro Leu Ser Pro Arg Gln Pro
                180                 185                 190
Thr Ser Thr His Pro Val Ala Thr Pro Thr Ser Ser Gly His Asp His
                195                 200                 205
Leu Met Lys Ile Ser Ser Ser Ser Thr Val Ala Ile Pro Gly Tyr
210                 215                 220
Thr Phe Thr Ser Pro Gly Met Thr Thr Thr Leu Pro Ser Ser Val Ile
225                 230                 235                 240
Ser Gln Arg Thr Gln Gln Thr Ser Ser Gln Met Pro Ala Ser Ser Thr
                245                 250                 255
Ala Pro Ser Ser Gln Glu Thr Val Gln Pro Thr Ser Pro Ala Thr Ala
                260                 265                 270
Leu Arg Thr Pro Thr Leu Pro Glu Thr Met Ser Ser Ser Pro Thr Ala
                275                 280                 285
Ala Ser Thr Thr His Arg Tyr Pro Lys Thr Pro Ser Pro Thr Val Ala
                290                 295                 300
His Glu Ser Asn Trp Ala Lys Cys Glu Asp Leu Glu Thr Gln Thr Gln
305                 310                 315                 320
Ser Glu Lys Gln Leu Val Leu Asn Leu Thr Gly Asn Thr Leu Cys Ala
                325                 330                 335
Gly Gly Ala Ser Asp Glu Lys Leu Ile Ser Leu Ile Cys Arg Ala Val
                340                 345                 350
Lys Ala Thr Phe Asn Pro Ala Gln Asp Lys Cys Gly Ile Arg Leu Ala
                355                 360                 365
Ser Val Pro Gly Ser Gln Thr Val Val Lys Glu Ile Thr Ile His
                370                 375                 380
Thr Lys Leu Pro Ala Lys Asp Val Tyr Glu Arg Leu Lys Asp Lys Trp
385                 390                 395                 400
Asp Glu Leu Lys Glu Ala Gly Val Ser Asp Met Lys Leu Gly Asp Gln
                405                 410                 415
Gly Pro Pro Glu Glu Ala Glu Asp Arg Phe Ser Met Pro Leu Ile Ile
                420                 425                 430
Thr Ile Val Cys Met Ala Ser Phe Leu Leu Leu Val Ala Ala Leu Tyr
                435                 440                 445
```

Gly Cys Cys His Gln Arg Leu Ser Gln Arg Lys Asp Gln Gln Arg Leu
    450                 455                 460

Thr Glu Glu Leu Gln Thr Val Glu Asn Gly Tyr His Asp Asn Pro Thr
465                 470                 475                 480

Leu Glu Val Met Glu Thr Ser Ser Glu Met Gln Glu Lys Lys Val Val
                485                 490                 495

Ser Leu Asn Gly Glu Leu Gly Asp Ser Trp Ile Val Pro Leu Asp Asn
            500                 505                 510

Leu Thr Lys Asp Asp Leu Asp Glu Glu Asp Thr His Leu
        515                 520                 525

<210> SEQ ID NO 43
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Val Leu Thr Gln Thr Pro Ala Ser Val Glu Val Ala Val Gly
1               5                   10                  15

Gly Thr Val Thr Ile Lys Cys Gln Ala Ser Gln Ser Ile Ser Asn Tyr
            20                  25                  30

Leu Ala Trp Tyr Gln Arg Lys Pro Gly Gln Pro Pro Arg Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Val Ser Asn Asn
                85                  90                  95

Leu Asp Asn Ile Phe Gly Gly Gly Thr Glu Val Val Val Lys
            100                 105                 110

<210> SEQ ID NO 44
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gacattgtgc tgacccagac tccagcctcg gtggaggtag ctgtgggagg cacagtcacc    60
atcaagtgcc aggccagtca gagcattagt aattacttag cctggtatca gcggaaacca   120
gggcagcctc ccaggctcct gatctacagg gcatccactc tggcatctgg ggtctcatcg   180
cggttcaaag gcagtggatc tgggacacag ttcactctca ccatcagcgg cgtggagtgt   240
gccgatgctg ccacttacta ctgtcaacag ggttatgtca gtaataatct tgataatatt   300
ttcggcggag ggaccgaggt ggtggtcaaa c                                   331

<210> SEQ ID NO 45
<211> LENGTH: 270
<212> TYPE: DNA
<213> ORGANISM: Homo sapiens

<400> SEQUENCE: 45
gacatccaga tgacccagtc tccatcctcc ctgtctgcat ctgtaggaga cagagtcacc    60

```
atcacttgcc gggcgagtca gggcattagc aattatttag cctggtatca gcagaaacca    120
gggaaagttc ctaagctcct gatctatgct gcatccactt tgcaatcagg ggtcccatct    180
cggttcagtg gcagtggatc tgggacagat ttcactctca ccatcagcag cctgcagcct    240
gaagatgttg caacttatta ctgtcaaaag                                     270
```

<210> SEQ ID NO 46
<211> LENGTH: 90
<212> TYPE: PRT
<213> ORGANISM: Homo sapiens

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys
                85                  90
```

<210> SEQ ID NO 47
<211> LENGTH: 270
<212> TYPE: DNA
<213> ORGANISM: Homo sapiens

<400> SEQUENCE: 47

```
gacatccagt tgacccagtc tccatccttc ctgtctgcat ctgtaggaga cagagtcacc     60
atcacttgcc gggccagtca gggcattagc agttatttag cctggtatca gcaaaaacca    120
gggaaagccc ctaagctcct gatctatgct gcatccactt tgcaaagtgg ggtcccatca    180
aggttcagcg gcagtggatc tgggacagaa ttcactctca caatcagcag cctgcagcct    240
gaagattttg caacttatta ctgtcaacag                                     270
```

<210> SEQ ID NO 48
<211> LENGTH: 260
<212> TYPE: DNA
<213> ORGANISM: Homo sapiens

<400> SEQUENCE: 48

```
tgacccagtc tccatcctcc ctgtctgcat ctgtaggaga cagagtcacc atcacttgcc     60
gggcaagtca gggcattagc agtgctttag cctggtatca gcagaaacca gggaaagctc    120
ctaagctcct gatctatgat gcctccagtt tggaaagtgg ggtcccatca aggttcagcg    180
gcagtggatc tgggacagat ttcactctca ccatcagcag cctgcagcct gaagattttg    240
caacttatta ctgtcaacag                                                260
```

<210> SEQ ID NO 49
<211> LENGTH: 276
<212> TYPE: DNA
<213> ORGANISM: Homo sapiens

<400> SEQUENCE: 49

```
gacatccaga tgacccagtc tccatcctcc ctgtctgcat ctgtaggaga cagagtcacc    60
atcacttgcc gggcgagtca gggcattagc aattctttag cctggtatca gcagaaacca   120
gggaaagccc ctaagctcct gctctatgct gcatccagat tggaaagtgg ggtcccatcc   180
aggttcagtg gcagtggatc tgggacggat tacactctca ccatcagcag cctgcagcct   240
gaagattttg caactattat ctgtcaacag tattat                             276
```

```
<210> SEQ ID NO 50
<211> LENGTH: 32
<212> TYPE: DNA
<213> ORGANISM: Homo sapiens

<400> SEQUENCE: 50
tttcggcgga gggaccaagg tggagatcaa ac                                  32

<210> SEQ ID NO 51
<211> LENGTH: 31
<212> TYPE: DNA
<213> ORGANISM: Homo sapiens

<400> SEQUENCE: 51
ttcggcggag ggaccaaggt ggagatcaaa c                                   31

<210> SEQ ID NO 52
<211> LENGTH: 14
<212> TYPE: DNA
<213> ORGANISM: Homo sapiens

<400> SEQUENCE: 52
agggaccaag gtgg                                                      14

<210> SEQ ID NO 53
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: T or M
<220> FEATURE:
<221> NAME/KEY: MOD_RES
<222> LOCATION: (5)..(5)
<223> OTHER INFORMATION: A or V
<220> FEATURE:
<221> NAME/KEY: MOD_RES
<222> LOCATION: (7)..(7)
<223> OTHER INFORMATION: T or A
<220> FEATURE:
<221> NAME/KEY: MOD_RES
<222> LOCATION: (19)..(19)
<223> OTHER INFORMATION: G or D
<220> FEATURE:
<221> NAME/KEY: MOD_RES
<222> LOCATION: (20)..(20)
<223> OTHER INFORMATION: A or T
<220> FEATURE:
<221> NAME/KEY: MOD_RES
<222> LOCATION: (26)..(26)
<223> OTHER INFORMATION: V or Q
<220> FEATURE:
<221> NAME/KEY: MOD_RES
<222> LOCATION: (27)..(27)
<223> OTHER INFORMATION: L or M
<220> FEATURE:
<221> NAME/KEY: MOD_RES
<222> LOCATION: (30)..(30)
```

```
<223> OTHER INFORMATION: T or S
<220> FEATURE:
<221> NAME/KEY: MOD_RES
<222> LOCATION: (32)..(32)
<223> OTHER INFORMATION: A or S
<220> FEATURE:
<221> NAME/KEY: MOD_RES
<222> LOCATION: (34)..(34)
<223> OTHER INFORMATION: V or L
<220> FEATURE:
<221> NAME/KEY: MOD_RES
<222> LOCATION: (35)..(35)
<223> OTHER INFORMATION: E or S
<220> FEATURE:
<221> NAME/KEY: MOD_RES
<222> LOCATION: (36)..(36)
<223> OTHER INFORMATION: V or A
<220> FEATURE:
<221> NAME/KEY: MOD_RES
<222> LOCATION: (37)..(37)
<223> OTHER INFORMATION: A or S
<220> FEATURE:
<221> NAME/KEY: MOD_RES
<222> LOCATION: (40)..(40)
<223> OTHER INFORMATION: G or D
<220> FEATURE:
<221> NAME/KEY: MOD_RES
<222> LOCATION: (41)..(41)
<223> OTHER INFORMATION: T or R
<220> FEATURE:
<221> NAME/KEY: MOD_RES
<222> LOCATION: (45)..(45)
<223> OTHER INFORMATION: K or T
<220> FEATURE:
<221> NAME/KEY: MOD_RES
<222> LOCATION: (47)..(47)
<223> OTHER INFORMATION: Q or R
<220> FEATURE:
<221> NAME/KEY: MOD_RES
<222> LOCATION: (51)..(51)
<223> OTHER INFORMATION: S or G
<220> FEATURE:
<221> NAME/KEY: MOD_RES
<222> LOCATION: (61)..(61)
<223> OTHER INFORMATION: R or Q
<220> FEATURE:
<221> NAME/KEY: MOD_RES
<222> LOCATION: (65)..(65)
<223> OTHER INFORMATION: Q or K
<220> FEATURE:
<221> NAME/KEY: MOD_RES
<222> LOCATION: (66)..(66)
<223> OTHER INFORMATION: P or V
<220> FEATURE:
<221> NAME/KEY: MOD_RES
<222> LOCATION: (68)..(68)
<223> OTHER INFORMATION: R or K
<220> FEATURE:
<221> NAME/KEY: MOD_RES
<222> LOCATION: (73)..(73)
<223> OTHER INFORMATION: R or A
<220> FEATURE:
<221> NAME/KEY: MOD_RES
<222> LOCATION: (78)..(78)
<223> OTHER INFORMATION: A or Q
<220> FEATURE:
<221> NAME/KEY: MOD_RES
<222> LOCATION: (82)..(82)
<223> OTHER INFORMATION: S or P
<220> FEATURE:
<221> NAME/KEY: MOD_RES
<222> LOCATION: (86)..(86)
<223> OTHER INFORMATION: K or S
<220> FEATURE:
<221> NAME/KEY: MOD_RES
<222> LOCATION: (93)..(93)
<223> OTHER INFORMATION: Q or D
<220> FEATURE:
<221> NAME/KEY: MOD_RES
```

```
<222> LOCATION: (100)..(100)
<223> OTHER INFORMATION: G or S
<220> FEATURE:
<221> NAME/KEY: MOD_RES
<222> LOCATION: (101)..(101)
<223> OTHER INFORMATION: V or L
<220> FEATURE:
<221> NAME/KEY: MOD_RES
<222> LOCATION: (103)..(103)
<223> OTHER INFORMATION: C or P
<220> FEATURE:
<221> NAME/KEY: MOD_RES
<222> LOCATION: (104)..(104)
<223> OTHER INFORMATION: A or E
<220> FEATURE:
<221> NAME/KEY: MOD_RES
<222> LOCATION: (106)..(106)
<223> OTHER INFORMATION: A or V
<220> FEATURE:
<221> NAME/KEY: MOD_RES
<222> LOCATION: (113)..(113)
<223> OTHER INFORMATION: Q or K
<220> FEATURE:
<221> NAME/KEY: MOD_RES
<222> LOCATION: (116)..(116)
<223> OTHER INFORMATION: V or N
<220> FEATURE:
<221> NAME/KEY: MOD_RES
<222> LOCATION: (118)..(118)
<223> OTHER INFORMATION: N or A
<220> FEATURE:
<221> NAME/KEY: MOD_RES
<222> LOCATION: (119)..(119)
<223> OTHER INFORMATION: N or P

<400> SEQUENCE: 53

Met Asp Xaa Arg Xaa Pro Xaa Gln Leu Leu Gly Leu Leu Leu Leu Trp
1               5                   10                  15

Leu Pro Xaa Xaa Arg Cys Ala Asp Ile Xaa Xaa Thr Gln Xaa Pro Xaa
            20                  25                  30

Ser Xaa Xaa Xaa Xaa Val Gly Xaa Xaa Val Thr Ile Xaa Cys Xaa Ala
        35                  40                  45

Ser Gln Xaa Ile Ser Asn Tyr Leu Ala Trp Tyr Gln Xaa Lys Pro Gly
    50                  55                  60

Xaa Xaa Pro Xaa Leu Leu Ile Tyr Xaa Ala Ser Thr Leu Xaa Ser Gly
65                  70                  75                  80

Val Xaa Ser Arg Phe Xaa Gly Ser Gly Ser Gly Thr Xaa Phe Thr Leu
                85                  90                  95

Thr Ile Ser Xaa Xaa Glx Xaa Xaa Asp Xaa Ala Thr Tyr Tyr Cys Gln
                100                 105                 110

Xaa Gly Tyr Xaa Ser Xaa Xaa Leu Asp Asn Ile Phe Gly Gly Gly Thr
            115                 120                 125

Glu Val Val Val Lys Arg Thr
    130                 135

<210> SEQ ID NO 54
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Asp Thr Arg Ala Pro Thr Gln Leu Leu Gly Leu Leu Leu Leu Trp
1               5                   10                  15

Leu Pro Gly Ala Arg Cys Ala Asp Ile Val Leu Thr Gln Thr Pro Ala
```

```
                20                  25                  30
Ser Val Glu Val Ala Val Gly Gly Thr Val Thr Ile Lys Cys Gln Ala
            35                  40                  45

Ser Gln Ser Ile Ser Asn Tyr Leu Ala Trp Tyr Gln Arg Lys Pro Gly
        50                  55                  60

Gln Pro Pro Arg Leu Leu Ile Tyr Arg Ala Ser Thr Leu Ala Ser Gly
 65                 70                  75                  80

Val Ser Ser Arg Phe Lys Gly Ser Gly Ser Gly Thr Gln Phe Thr Leu
                85                  90                  95

Thr Ile Ser Gly Val Glu Cys Ala Asp Ala Ala Thr Tyr Tyr Cys Gln
            100                 105                 110

Gln Gly Tyr Val Ser Asn Asn Leu Asp Asn Ile Phe Gly Gly Gly Thr
        115                 120                 125

Glu Val Val Val Lys Arg Thr
        130                 135

<210> SEQ ID NO 55
<211> LENGTH: 117
<212> TYPE: PRT
<213> ORGANISM: Homo sapiens

<400> SEQUENCE: 55

Met Asp Met Arg Val Pro Ala Gln Leu Leu Gly Leu Leu Leu Leu Trp
 1               5                  10                  15

Leu Pro Asp Thr Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Gly Ile Ser Asn Tyr Leu Ala Trp Tyr Gln Gln Lys Pro Gly Lys
        50                  55                  60

Val Pro Lys Leu Leu Ile Tyr Ala Ala Ser Thr Leu Gln Ser Gly Val
 65                 70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Val Ala Thr Tyr Tyr Cys Gln Lys
            100                 105                 110

Tyr Asn Ser Ala Pro
        115

<210> SEQ ID NO 56
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Leu Ala Glu Ser Gly Gly Arg Leu Val Thr Pro Gly Thr Pro Leu Thr
 1               5                  10                  15

Leu Thr Cys Thr Ala Ser Gly Ile Asp Leu Ser Ser Tyr Ala Met Gly
                20                  25                  30

Trp Val Arg Gln Ala Pro Gly Lys Gly Leu Glu Tyr Ile Gly Phe Ile
            35                  40                  45

Tyr Ala Ser Gly Ser Ile Phe Tyr Ala Ser Trp Ala Lys Gly Arg Phe
        50                  55                  60

Thr Ile Ser Lys Thr Ser Ser Thr Thr Val Asp Leu Lys Met Thr Ser
```

```
                65                  70                  75                  80
Leu Thr Thr Glu Asp Thr Ala Thr Tyr Phe Cys Ala Arg Ala Gly Tyr
                    85                  90                  95

Tyr Phe Gly Gly Asn Tyr Asp Leu Asn Leu Trp Gly Gln Gly Thr Leu
            100                 105                 110

Val Thr Val Ser Ser
        115

<210> SEQ ID NO 57
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gctggcggag tccgggggtc gcctggtcac gcctggcaca cccctgacac tcacctgcac     60
agcctctgga atcgacctca gtagctatgc aatgggctgg gtccgccagg ctccagggaa    120
ggggctggaa tacatcggat tcatttatgc tagtggcagt atattctacg cgagctgggc    180
gaaaggccga ttcaccatct ccaaaacctc gtcgaccacg gtggatctga aaatgaccag    240
cctgacaacc gaggacacgg ccacctattt ctgtgccaga gcggatatt attttggtgg    300 taattatgat cttaacttgt ggggccaagg caccctggtc accgtctctt c             351

<210> SEQ ID NO 58
<211> LENGTH: 287
<212> TYPE: DNA
<213> ORGANISM: Homo sapiens

<400> SEQUENCE: 58
gctggtggag tctgggggag gcctggtcaa gcctgggggg tccctgagac tctcctgtgc     60
agcctctgga ttcaccttca gtagctatag catgaactgg gtccgccagg ctccagggaa    120
ggggctggag tgggtctcat ccattagtag tagtagtagt tacatatact acgcagactc    180
agtgaagggc cgattcacca ctctccagaga caacgccaag aactcactgt atctgcaaat    240
gaacagcctg agagccgagg acacggccgt gtattactgt gcgagag                  287

<210> SEQ ID NO 59
<211> LENGTH: 95
<212> TYPE: PRT
<213> ORGANISM: Homo sapiens

<400> SEQUENCE: 59

Leu Val Glu Ser Gly Gly Gly Leu Val Lys Pro Gly Gly Ser Leu Arg
1               5                   10                  15

Leu Ser Cys Ala Ala Ser Gly Phe Thr Phe Ser Ser Tyr Ser Met Asn
            20                  25                  30

Trp Val Arg Gln Ala Pro Gly Lys Gly Leu Glu Trp Val Ser Ser Ile
        35                  40                  45

Ser Ser Ser Ser Ser Tyr Ile Tyr Tyr Ala Asp Ser Val Lys Gly Arg
    50                  55                  60

Phe Thr Ile Ser Arg Asp Asn Ala Lys Asn Ser Leu Tyr Leu Gln Met
65                  70                  75                  80

Asn Ser Leu Arg Ala Glu Asp Thr Ala Val Tyr Tyr Cys Ala Arg
                85                  90                  95
```

<210> SEQ ID NO 60
<211> LENGTH: 287
<212> TYPE: DNA
<213> ORGANISM: Homo sapiens

<400> SEQUENCE: 60
gctggtggag tctgggggag gcctggtcaa gcctgggggg tccctgagac tctcctgtgc      60
agcctctgga ttcaccttca gtagctatag catgaactgg gtccgccagg ctccagggaa     120
ggggctggag tgggtctcat ccattagtag tagtagtagt tacatatact acgcagactc     180
agtgaagggc cgattcacca tctccagaga caacgccaag aactcactgt atctgcaaat     240
gaacagcctg agagccgagg acacggctgt gtattactgt gcgagag                   287

<210> SEQ ID NO 61
<211> LENGTH: 286
<212> TYPE: DNA
<213> ORGANISM: Homo sapiens

<400> SEQUENCE: 61
ctggtggagt ctgggggagg cctggtcaag cctgggggt ccctgagact ctcctgtgca       60
gcctctggat tcaccttcag tagctatagc atgaactggg tccgccaggc tccagggaag    120
gggctggagt gggtctcatc cattagtagt agtagtagtt acatatacta cgcagactca    180
gtgaagggcc gattcaccat ctccagagac aacgccaaga actcactgta tctgcaaatg    240
aacagcctga gagccgagga cacggctgtg tattactgtg cgagag                    286

<210> SEQ ID NO 62
<211> LENGTH: 287
<212> TYPE: DNA
<213> ORGANISM: Homo sapiens

<400> SEQUENCE: 62
gctggtggag tctgggggag gcctggtcaa gcctgggggg tccctgagac tctcctgtgc      60
agcctctgga ttcaccttca gtagctatag catgaactgg gtccgccagg ctccagggaa     120
ggggctggag tgggtctcat ccattagtag tagtagtagt tacatatact acgcagactc     180
agtgaagggc cgattcacca tctccagaga caacgccaag aactcactgt atctgcaaat     240
gaacagcctg agagccgagg acacagctgt gtattactgt gcgagag                   287

<210> SEQ ID NO 63
<211> LENGTH: 286
<212> TYPE: DNA
<213> ORGANISM: Homo sapiens

<400> SEQUENCE: 63
gctggtggag tctgggggag gcgtggtcca gcctggggag tccctgagac tctcctgtgc      60
agcctctgga ttcaccttca gtagctatgc tatgcactgg gtccgccagg ctccaggcaa     120
ggggctggag tgggtggcag ttatatcata tgatggaaga aataaatact acgcagactc     180
cgtgaagggc cgattcacca tctccagaga caattccaag aacacgctgt atctgcaaat     240
gaacagcctg agagctgagg acacggctgt gtattactgt gcgaga                    286

<210> SEQ ID NO 64
<211> LENGTH: 284
<212> TYPE: DNA
<213> ORGANISM: Homo sapiens

<400> SEQUENCE: 64

```
gctggtggag tctgggggag gcttggtcca gcctgggggg tccctgagac tctcctgtgc    60
agcctctgga ttcaccgtca gtagcaacta catgagctgg gtccgccagg ctccagggaa   120
ggggctggag tgggtctcag ttatttatag cggtggtagc acatactacg cagactccgt   180
gaagggcaga ttcaccatct ccagagacaa ttccaagaac acgctgtatc ttcaaatgaa   240
cagcctgaga gccgaggaca cggctgtgta ttactgtgcg agag                    284

<210> SEQ ID NO 65
<211> LENGTH: 287
<212> TYPE: DNA
<213> ORGANISM: Homo sapiens

<400> SEQUENCE: 65
gctggtggag tctgggggag gcgtggtcca gcctgggagg tccctgagac tctcctgtgc    60
agcctctgga ttcaccttca gtagctatgc tatgcactgg gtccgccagg ctccaggcaa   120
ggggctagag tgggtggcag ttatatcata tgatggaagt aataaatact acgcagactc   180
cgtgaagggc cgattcacca tctccagaga caattccaag aacacgctgt atctgcaaat   240
gaacagcctg agagccgagg acacggctgt gtattactgt gcgagag                 287

<210> SEQ ID NO 66
<211> LENGTH: 287
<212> TYPE: DNA
<213> ORGANISM: Homo sapiens

<400> SEQUENCE: 66
gctggtggag tctgggggag gcttggtaca gcctggaggg tccctgagac tctcctgtgc    60
agcctctgga ttcaccttca gtagttatga aatgaactgg gtccgccagg ctccagggaa   120
ggggctggag tgggtttcat acattagtag tagtggtagt accatatact acgcagactc   180
tgtgaagggc cgattcacca tctccagaga caacgccaag aactcactgt atctgcaaat   240
gaacagcctg agagccgagg acacggctgt ttattactgt gcgagag                 287

<210> SEQ ID NO 67
<211> LENGTH: 287
<212> TYPE: DNA
<213> ORGANISM: Homo sapiens

<400> SEQUENCE: 67
gctggtggag tctgggggag gcgtggtcca gcctgggagg tccctgagac tctcctgtgc    60
agcctctgga ttcaccttca gtagctatgc tatgcactgg gtccgccagg ctccaggcaa   120
ggggctggag tgggtggcag ttatatcata tgatggaagt aataaatact acgcagactc   180
cgtgaagggc cgattcacca tctccagaga caattccaag aacacgctgt atctgcaaat   240
gaacagcctg agagctgagg acacggctgt gtattactgt gcgagag                 287

<210> SEQ ID NO 68
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: T or F
<220> FEATURE:
<221> NAME/KEY: MOD_RES
<222> LOCATION: (6)..(6)
```

```
-continued

<223> OTHER INFORMATION: R or S
<220> FEATURE:
<221> NAME/KEY: MOD_RES
<222> LOCATION: (8)..(8)
<223> OTHER INFORMATION: L or V
<220> FEATURE:
<221> NAME/KEY: MOD_RES
<222> LOCATION: (9)..(9)
<223> OTHER INFORMATION: L or F
<220> FEATURE:
<221> NAME/KEY: MOD_RES
<222> LOCATION: (13)..(13)
<223> OTHER INFORMATION: V or I
<220> FEATURE:
<221> NAME/KEY: MOD_RES
<222> LOCATION: (22)..(22)
<223> OTHER INFORMATION: S or Q
<220> FEATURE:
<221> NAME/KEY: MOD_RES
<222> LOCATION: (24)..(24)
<223> OTHER INFORMATION: A or V
<220> FEATURE:
<221> NAME/KEY: MOD_RES
<222> LOCATION: (29)..(29)
<223> OTHER INFORMATION: R or G
<220> FEATURE:
<221> NAME/KEY: MOD_RES
<222> LOCATION: (32)..(32)
<223> OTHER INFORMATION: T or Q
<220> FEATURE:
<221> NAME/KEY: MOD_RES
<222> LOCATION: (35)..(35)
<223> OTHER INFORMATION: T or G
<220> FEATURE:
<221> NAME/KEY: MOD_RES
<222> LOCATION: (36)..(36)
<223> OTHER INFORMATION: P or S
<220> FEATURE:
<221> NAME/KEY: MOD_RES
<222> LOCATION: (38)..(38)
<223> OTHER INFORMATION: T or R
<220> FEATURE:
<221> NAME/KEY: MOD_RES
<222> LOCATION: (40)..(40)
<223> OTHER INFORMATION: T or S
<220> FEATURE:
<221> NAME/KEY: MOD_RES
<222> LOCATION: (42)..(42)
<223> OTHER INFORMATION: T or A
<220> FEATURE:
<221> NAME/KEY: MOD_RES
<222> LOCATION: (46)..(46)
<223> OTHER INFORMATION: I or F
<220> FEATURE:
<221> NAME/KEY: MOD_RES
<222> LOCATION: (47)..(47)
<223> OTHER INFORMATION: D or T
<220> FEATURE:
<221> NAME/KEY: MOD_RES
<222> LOCATION: (48)..(48)
<223> OTHER INFORMATION: L or V
<220> FEATURE:
<221> NAME/KEY: MOD_RES
<222> LOCATION: (51)..(51)
<223> OTHER INFORMATION: Y or N
<220> FEATURE:
<221> NAME/KEY: MOD_RES
<222> LOCATION: (52)..(52)
<223> OTHER INFORMATION: A or Y
<220> FEATURE:
<221> NAME/KEY: MOD_RES
<222> LOCATION: (54)..(54)
<223> OTHER INFORMATION: G or S
<220> FEATURE:
<221> NAME/KEY: MOD_RES
<222> LOCATION: (66)..(66)
<223> OTHER INFORMATION: Y or W
<220> FEATURE:
<221> NAME/KEY: MOD_RES
```

```
<222> LOCATION: (67)..(67)
<223> OTHER INFORMATION: I or V
<220> FEATURE:
<221> NAME/KEY: MOD_RES
<222> LOCATION: (68)..(68)
<223> OTHER INFORMATION: G or S
<220> FEATURE:
<221> NAME/KEY: MOD_RES
<222> LOCATION: (69)..(69)
<223> OTHER INFORMATION: F or V
<220> FEATURE:
<221> NAME/KEY: MOD_RES
<222> LOCATION: (72)..(72)
<223> OTHER INFORMATION: A or S
<220> FEATURE:
<221> NAME/KEY: MOD_RES
<222> LOCATION: (73)..(73)
<223> OTHER INFORMATION: S or G
<220> FEATURE:
<221> NAME/KEY: MOD_RES
<222> LOCATION: (76)..(76)
<223> OTHER INFORMATION: I or T
<220> FEATURE:
<221> NAME/KEY: MOD_RES
<222> LOCATION: (77)..(77)
<223> OTHER INFORMATION: F or Y
<220> FEATURE:
<221> NAME/KEY: MOD_RES
<222> LOCATION: (80)..(80)
<223> OTHER INFORMATION: S or D
<220> FEATURE:
<221> NAME/KEY: MOD_RES
<222> LOCATION: (81)..(81)
<223> OTHER INFORMATION: W or S
<220> FEATURE:
<221> NAME/KEY: MOD_RES
<222> LOCATION: (82)..(82)
<223> OTHER INFORMATION: A or V
<220> FEATURE:
<221> NAME/KEY: MOD_RES
<222> LOCATION: (90)..(90)
<223> OTHER INFORMATION: K or R
<220> FEATURE:
<221> NAME/KEY: MOD_RES
<222> LOCATION: (91)..(91)
<223> OTHER INFORMATION: T or D
<220> FEATURE:
<221> NAME/KEY: MOD_RES
<222> LOCATION: (92)..(92)
<223> OTHER INFORMATION: S or N
<220> FEATURE:
<221> NAME/KEY: MOD_RES
<222> LOCATION: (95)..(95)
<223> OTHER INFORMATION: T or N
<220> FEATURE:
<221> NAME/KEY: MOD_RES
<222> LOCATION: (97)..(97)
<223> OTHER INFORMATION: V or L
<220> FEATURE:
<221> NAME/KEY: MOD_RES
<222> LOCATION: (98)..(98)
<223> OTHER INFORMATION: D or Y
<220> FEATURE:
<221> NAME/KEY: MOD_RES
<222> LOCATION: (100)..(100)
<223> OTHER INFORMATION: K or Q
<220> FEATURE:
<221> NAME/KEY: MOD_RES
<222> LOCATION: (102)..(102)
<223> OTHER INFORMATION: T or N
<220> FEATURE:
<221> NAME/KEY: MOD_RES
<222> LOCATION: (105)..(105)
<223> OTHER INFORMATION: T or R
<220> FEATURE:
<221> NAME/KEY: MOD_RES
<222> LOCATION: (106)..(106)
<223> OTHER INFORMATION: T or A
<220> FEATURE:
```

<220> FEATURE:
<221> NAME/KEY: MOD_RES
<222> LOCATION: (111)..(111)
<223> OTHER INFORMATION: T or V
<220> FEATURE:
<221> NAME/KEY: MOD_RES
<222> LOCATION: (113)..(113)
<223> OTHER INFORMATION: F or Y

<400> SEQUENCE: 68

```
Met Glu Xaa Gly Leu Xaa Trp Xaa Xaa Leu Val Ala Xaa Leu Lys Gly
1               5                   10                  15

Val Gln Cys Glx Val Xaa Leu Xaa Glu Ser Gly Gly Xaa Leu Val Xaa
                20                  25                  30

Pro Gly Xaa Xaa Leu Xaa Leu Xaa Cys Xaa Ala Ser Gly Xaa Xaa Xaa
            35                  40                  45

Ser Ser Xaa Xaa Met Xaa Trp Val Arg Gln Ala Pro Gly Lys Gly Leu
50                  55                  60

Glu Xaa Xaa Xaa Xaa Ile Tyr Xaa Xaa Gly Ser Xaa Xaa Tyr Ala Xaa
65                  70                  75                  80

Xaa Xaa Lys Gly Arg Phe Thr Ile Ser Xaa Xaa Xaa Ser Lys Xaa Thr
                85                  90                  95

Xaa Xaa Leu Xaa Met Xaa Ser Leu Xaa Xaa Glu Asp Thr Ala Xaa Tyr
                100                 105                 110

Xaa Cys Ala Arg Ala Gly Tyr Tyr Phe Gly Gly Asn Tyr Asp Leu Asn
            115                 120                 125

Leu Trp Gly Gln Gly Thr Leu Val Thr Val Ser Ser Ala Ser
            130                 135                 140
```

<210> SEQ ID NO 69
<211> LENGTH: 140
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Met Glu Thr Gly Leu Arg Trp Leu Leu Leu Val Ala Val Leu Lys Gly
1               5                   10                  15

Val Gln Cys Gln Ser Leu Ala Glu Ser Gly Gly Arg Leu Val Thr Pro
                20                  25                  30

Gly Thr Pro Leu Thr Leu Thr Cys Thr Ala Ser Gly Ile Asp Leu Ser
            35                  40                  45

Ser Tyr Ala Met Gly Trp Val Arg Gln Ala Pro Gly Lys Gly Leu Glu
50                  55                  60

Tyr Ile Gly Phe Ile Tyr Ala Ser Gly Ser Ile Phe Tyr Ala Ser Trp
65                  70                  75                  80

Ala Lys Gly Arg Phe Thr Ile Ser Lys Thr Ser Ser Thr Thr Val Asp
                85                  90                  95

Leu Lys Met Thr Ser Leu Thr Thr Glu Asp Thr Ala Thr Tyr Phe Cys
                100                 105                 110

Ala Arg Ala Gly Tyr Tyr Phe Gly Gly Asn Tyr Asp Leu Asn Leu Trp
            115                 120                 125

Gly Gln Gly Thr Leu Val Thr Val Ser Ser Ala Ser
            130                 135                 140
```

<210> SEQ ID NO 70
<211> LENGTH: 116
<212> TYPE: PRT

<213> ORGANISM: Homo sapiens

<400> SEQUENCE: 70

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Val
        35                  40                  45

Ser Ser Asn Tyr Met Ser Trp Val Arg Gln Ala Pro Gly Lys Gly Leu
    50                  55                  60

Glu Trp Val Ser Val Ile Tyr Ser Gly Gly Ser Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg
        115

<210> SEQ ID NO 71
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: T or M
<220> FEATURE:
<221> NAME/KEY: MOD_RES
<222> LOCATION: (5)..(5)
<223> OTHER INFORMATION: A or V
<220> FEATURE:
<221> NAME/KEY: MOD_RES
<222> LOCATION: (7)..(7)
<223> OTHER INFORMATION: T or A
<220> FEATURE:
<221> NAME/KEY: MOD_RES
<222> LOCATION: (19)..(19)
<223> OTHER INFORMATION: G or D
<220> FEATURE:
<221> NAME/KEY: MOD_RES
<222> LOCATION: (20)..(20)
<223> OTHER INFORMATION: A or T
<220> FEATURE:
<221> NAME/KEY: MOD_RES
<222> LOCATION: (26)..(26)
<223> OTHER INFORMATION: V or Q
<220> FEATURE:
<221> NAME/KEY: MOD_RES
<222> LOCATION: (27)..(27)
<223> OTHER INFORMATION: L or M
<220> FEATURE:
<221> NAME/KEY: MOD_RES
<222> LOCATION: (30)..(30)
<223> OTHER INFORMATION: T or S
<220> FEATURE:
<221> NAME/KEY: MOD_RES
<222> LOCATION: (32)..(32)
<223> OTHER INFORMATION: A or S
<220> FEATURE:
<221> NAME/KEY: MOD_RES
<222> LOCATION: (34)..(34)
<223> OTHER INFORMATION: V or L
<220> FEATURE:
<221> NAME/KEY: MOD_RES
<222> LOCATION: (35)..(35)

```
<223> OTHER INFORMATION: E or S
<220> FEATURE:
<221> NAME/KEY: MOD_RES
<222> LOCATION: (36)..(36)
<223> OTHER INFORMATION: V or A
<220> FEATURE:
<221> NAME/KEY: MOD_RES
<222> LOCATION: (37)..(37)
<223> OTHER INFORMATION: A or S
<220> FEATURE:
<221> NAME/KEY: MOD_RES
<222> LOCATION: (40)..(40)
<223> OTHER INFORMATION: G or D
<220> FEATURE:
<221> NAME/KEY: MOD_RES
<222> LOCATION: (41)..(41)
<223> OTHER INFORMATION: T or R
<220> FEATURE:
<221> NAME/KEY: MOD_RES
<222> LOCATION: (45)..(45)
<223> OTHER INFORMATION: K or T
<220> FEATURE:
<221> NAME/KEY: MOD_RES
<222> LOCATION: (61)..(61)
<223> OTHER INFORMATION: R or Q
<220> FEATURE:
<221> NAME/KEY: MOD_RES
<222> LOCATION: (65)..(65)
<223> OTHER INFORMATION: Q or K
<220> FEATURE:
<221> NAME/KEY: MOD_RES
<222> LOCATION: (66)..(66)
<223> OTHER INFORMATION: P or V
<220> FEATURE:
<221> NAME/KEY: MOD_RES
<222> LOCATION: (68)..(68)
<223> OTHER INFORMATION: R or K
<220> FEATURE:
<221> NAME/KEY: MOD_RES
<222> LOCATION: (82)..(82)
<223> OTHER INFORMATION: S or P
<220> FEATURE:
<221> NAME/KEY: MOD_RES
<222> LOCATION: (86)..(86)
<223> OTHER INFORMATION: K or S
<220> FEATURE:
<221> NAME/KEY: MOD_RES
<222> LOCATION: (93)..(93)
<223> OTHER INFORMATION: Q or D
<220> FEATURE:
<221> NAME/KEY: MOD_RES
<222> LOCATION: (100)..(100)
<223> OTHER INFORMATION: G or S
<220> FEATURE:
<221> NAME/KEY: MOD_RES
<222> LOCATION: (101)..(101)
<223> OTHER INFORMATION: V or L
<220> FEATURE:
<221> NAME/KEY: MOD_RES
<222> LOCATION: (103)..(103)
<223> OTHER INFORMATION: C or P
<220> FEATURE:
<221> NAME/KEY: MOD_RES
<222> LOCATION: (104)..(104)
<223> OTHER INFORMATION: A or E
<220> FEATURE:
<221> NAME/KEY: MOD_RES
<222> LOCATION: (106)..(106)
<223> OTHER INFORMATION: A or V

<400> SEQUENCE: 71

Met Asp Xaa Arg Xaa Pro Xaa Gln Leu Leu Gly Leu Leu Leu Leu Trp
1               5                   10                  15

Leu Pro Xaa Xaa Arg Cys Ala Asp Ile Xaa Xaa Thr Gln Xaa Pro Xaa
            20                  25                  30

Ser Xaa Xaa Xaa Xaa Val Gly Xaa Xaa Val Thr Ile Xaa Cys Gln Ala
```

```
                35                  40                  45
Ser Gln Ser Ile Ser Asn Tyr Leu Ala Trp Tyr Gln Xaa Lys Pro Gly
 50                  55                  60

Xaa Xaa Pro Xaa Leu Leu Ile Tyr Arg Ala Ser Thr Leu Ala Ser Gly
 65                  70                  75                  80

Val Xaa Ser Arg Phe Xaa Gly Ser Gly Ser Gly Thr Xaa Phe Thr Leu
                 85                  90                  95

Thr Ile Ser Xaa Xaa Glx Xaa Xaa Asp Xaa Ala Thr Tyr Tyr Cys Gln
                100                 105                 110

Gln Gly Tyr Val Ser Asn Asn Leu Asp Asn Ile Phe Gly Gly Gly Thr
            115                 120                 125

Glu Val Val Val Lys Arg Thr
130                 135

<210> SEQ ID NO 72
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Asp Met Arg Val Pro Ala Gln Leu Leu Gly Leu Leu Leu Leu Trp
 1               5                  10                  15

Leu Pro Asp Thr Arg Cys Asp Ile Gln Met Thr Gln Ser Pro Ser Ser
                20                  25                  30

Leu Ser Ala Ser Val Gly Asp Arg Val Thr Ile Thr Cys Gln Ala Ser
            35                  40                  45

Gln Ser Ile Ser Asn Tyr Leu Ala Trp Tyr Gln Gln Lys Pro Gly Lys
 50                  55                  60

Val Pro Lys Leu Leu Ile Tyr Arg Ala Ser Thr Leu Ala Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Val Ala Thr Tyr Tyr Cys Gln Gln
                100                 105                 110

Gly Tyr Val Ser Asn Asn Leu Asp Asn Ile Phe Gly Gly Gly Thr Glu
            115                 120                 125

Val Val Val Lys Arg Thr
    130

<210> SEQ ID NO 73
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: T or F
<220> FEATURE:
<221> NAME/KEY: MOD_RES
<222> LOCATION: (6)..(6)
<223> OTHER INFORMATION: R or S
<220> FEATURE:
<221> NAME/KEY: MOD_RES
<222> LOCATION: (8)..(8)
<223> OTHER INFORMATION: L or V
<220> FEATURE:
```

```
<221> NAME/KEY: MOD_RES
<222> LOCATION: (9)..(9)
<223> OTHER INFORMATION: L or F
<220> FEATURE:
<221> NAME/KEY: MOD_RES
<222> LOCATION: (13)..(13)
<223> OTHER INFORMATION: V or I
<220> FEATURE:
<221> NAME/KEY: MOD_RES
<222> LOCATION: (22)..(22)
<223> OTHER INFORMATION: S or Q
<220> FEATURE:
<221> NAME/KEY: MOD_RES
<222> LOCATION: (24)..(24)
<223> OTHER INFORMATION: A or V
<220> FEATURE:
<221> NAME/KEY: MOD_RES
<222> LOCATION: (29)..(29)
<223> OTHER INFORMATION: R or G
<220> FEATURE:
<221> NAME/KEY: MOD_RES
<222> LOCATION: (32)..(32)
<223> OTHER INFORMATION: T or Q
<220> FEATURE:
<221> NAME/KEY: MOD_RES
<222> LOCATION: (35)..(35)
<223> OTHER INFORMATION: T or G
<220> FEATURE:
<221> NAME/KEY: MOD_RES
<222> LOCATION: (36)..(36)
<223> OTHER INFORMATION: P or S
<220> FEATURE:
<221> NAME/KEY: MOD_RES
<222> LOCATION: (38)..(38)
<223> OTHER INFORMATION: T or R
<220> FEATURE:
<221> NAME/KEY: MOD_RES
<222> LOCATION: (40)..(40)
<223> OTHER INFORMATION: T or S
<220> FEATURE:
<221> NAME/KEY: MOD_RES
<222> LOCATION: (42)..(42)
<223> OTHER INFORMATION: T or A
<220> FEATURE:
<221> NAME/KEY: MOD_RES
<222> LOCATION: (66)..(66)
<223> OTHER INFORMATION: Y or W
<220> FEATURE:
<221> NAME/KEY: MOD_RES
<222> LOCATION: (67)..(67)
<223> OTHER INFORMATION: I or V
<220> FEATURE:
<221> NAME/KEY: MOD_RES
<222> LOCATION: (68)..(68)
<223> OTHER INFORMATION: G or S
<220> FEATURE:
<221> NAME/KEY: MOD_RES
<222> LOCATION: (90)..(90)
<223> OTHER INFORMATION: K or R
<220> FEATURE:
<221> NAME/KEY: MOD_RES
<222> LOCATION: (91)..(91)
<223> OTHER INFORMATION: T or D
<220> FEATURE:
<221> NAME/KEY: MOD_RES
<222> LOCATION: (92)..(92)
<223> OTHER INFORMATION: S or N
<220> FEATURE:
<221> NAME/KEY: MOD_RES
<222> LOCATION: (95)..(95)
<223> OTHER INFORMATION: T or N
<220> FEATURE:
<221> NAME/KEY: MOD_RES
<222> LOCATION: (97)..(97)
<223> OTHER INFORMATION: V or L
<220> FEATURE:
<221> NAME/KEY: MOD_RES
<222> LOCATION: (98)..(98)
<223> OTHER INFORMATION: D or Y
```

-continued

```
<220> FEATURE:
<221> NAME/KEY: MOD_RES
<222> LOCATION: (100)..(100)
<223> OTHER INFORMATION: K or Q
<220> FEATURE:
<221> NAME/KEY: MOD_RES
<222> LOCATION: (102)..(102)
<223> OTHER INFORMATION: T or N
<220> FEATURE:
<221> NAME/KEY: MOD_RES
<222> LOCATION: (105)..(105)
<223> OTHER INFORMATION: T or R
<220> FEATURE:
<221> NAME/KEY: MOD_RES
<222> LOCATION: (106)..(106)
<223> OTHER INFORMATION: T or A
<220> FEATURE:
<221> NAME/KEY: MOD_RES
<222> LOCATION: (111)..(111)
<223> OTHER INFORMATION: T or V
<220> FEATURE:
<221> NAME/KEY: MOD_RES
<222> LOCATION: (113)..(113)
<223> OTHER INFORMATION: F or Y

<400> SEQUENCE: 73

Met Glu Xaa Gly Leu Xaa Trp Xaa Xaa Leu Val Ala Xaa Leu Lys Gly
1               5                   10                  15

Val Gln Cys Glx Val Xaa Leu Xaa Glu Ser Gly Gly Xaa Leu Val Xaa
            20                  25                  30

Pro Gly Xaa Xaa Leu Xaa Leu Xaa Cys Xaa Ala Ser Gly Ile Asp Leu
        35                  40                  45

Ser Ser Tyr Ala Met Gly Trp Val Arg Gln Ala Pro Gly Lys Gly Leu
50                  55                  60

Glu Xaa Xaa Xaa Phe Ile Tyr Ala Ser Gly Ser Ile Phe Tyr Ala Ser
65                  70                  75                  80

Trp Ala Lys Gly Arg Phe Thr Ile Ser Xaa Xaa Xaa Ser Lys Xaa Thr
                85                  90                  95

Xaa Xaa Leu Xaa Met Xaa Ser Leu Xaa Xaa Glu Asp Thr Ala Xaa Tyr
            100                 105                 110

Xaa Cys Ala Arg Ala Gly Tyr Tyr Phe Gly Gly Asn Tyr Asp Leu Asn
        115                 120                 125

Leu Trp Gly Gln Gly Thr Leu Val Thr Val Ser Ser Ala Ser
130                 135                 140

<210> SEQ ID NO 74
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Ile Asp Leu
        35                  40                  45

Ser Ser Tyr Ala Met Gly Trp Val Arg Gln Ala Pro Gly Lys Gly Leu
50                  55                  60

Glu Trp Val Ser Phe Ile Tyr Ala Ser Gly Ser Ile Phe Tyr Ala Ser
65                  70                  75                  80
```

```
Trp Ala Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Ala Gly Tyr Tyr Phe Gly Gly Asn Tyr Asp Leu Asn
        115                 120                 125

Leu Trp Gly Gln Gly Thr Leu Val Thr Val Ser Ser Ala Ser
    130                 135                 140
```

<210> SEQ ID NO 75
<211> LENGTH: 417
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

```
gaattcgcca ccatggacac gagggccccc actcagctgc tggggctcct gctgctctgg      60
ctcccaggtg ccagatgtgc tgacattgtg ctgacccaga ctccagcctc ggtggaggta     120
gctgtgggag gcacagtcac catcaagtgc caggccagtc agagcattag taattactta     180
gcctggtatc agcggaaacc agggcagcct cccaggctcc tgatctacag gcatccact      240
ctggcatctg ggtctcatc gcggttcaaa ggcagtggat ctgggacaca gttcactctc     300
accatcagcg gcgtggagtg tgccgatgct gccacttact actgtcaaca gggttatgtc     360
agtaataatc ttgataatat tttcggcgga gggaccgagg tggtggtcaa acgtacg       417
```

<210> SEQ ID NO 76
<211> LENGTH: 430
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76

```
gaattccacc atggagactg gctgcgctg gcttctcctg gtcgctgtgc tcaaaggtgt       60
ccagtgtcag tcgctggcgg agtccggggg tcgcctggtc acgcctggca cacccctgac    120
actcacctgc acagcctctg gaatcgacct cagtagctat gcaatgggct gggtccgcca    180
ggctccaggg aaggggctgg aatacatcgg attcatttat gctagtggca gtatattcta    240
cgcgagctgg gcgaaaggcc gattcaccat ctccaaaacc tcgtcgacca cggtggatct    300
gaaaatgacc agcctgacaa ccgaggacac ggccacctat ttctgtgcca gagcgggata    360
ttatttggt ggtaattatg atcttaactt gtggggccaa ggcaccctgg tcaccgtctc    420
ttcagctagc                                                           430
```

<210> SEQ ID NO 77
<211> LENGTH: 420
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77

```
atggagtttg gtttgtcctg ggtgttcctg gtggcaatcc tcaaaggggt gcaatgcgag       60
gtccagctgg tggagagcgg gggcggactg gtgcagcctg agggtccctt gaggctgagc    120
```

-continued

```
tgtgctgcct ctggcattga tctgtcctct tatgccatgg gttgggtccg ccaggccccc      180
ggcaagggtc tcgagtgggt gagctttatt tacgcctctg ctccatctt ctacgcatct       240 tgggcgaagg ggcgcttcac catcagtagg gacaactcta agaataccctt gtatctgcag     300 atgaactccc tgcgggccga agataccgct gtgtattact gcgcccgggc aggctactat     360
ttcggcggaa attacgatct caatctctgg ggccagggca cactggtgac cgtgtcctct    420
```

<210> SEQ ID NO 78
<211> LENGTH: 417
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78

```
atggagtttg gtttgtcctg ggtgttcctg gtgcaatcc tcaaaggggt gcaatgcgag      60
gtccagctgg tggagagcgg gggcggactg gtgcagcctg gagggtcctt gaggctgagc    120
tgtgctgcct ctggcattga tctgtcctct tatgccatgg gttgggtccg ccaggccccc    180
ggcaagggtc tcgagtgggt gagctttatt tacgcctctg ctccatctt ctacgcatct    240 tgggcgaagg ggcgcttcac catcagtagg gacaactcta ataccttgta tctgcagatg    300
aactccctgc gggccgaaga taccgctgtg tattactgcg cccgggcagg ctactatttc    360
ggcggaaatt acgatctcaa tctctggggc cagggcacac tggtgaccgt gtcctct       417
```

<210> SEQ ID NO 79
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

```
atggacatgc gcgtgccagc gcagctgctg ggcctgctcc tcctgtggct cccagacacc     60
cgttgcgaca ttcaaatgac ccagtcccca tccagtctga gtgcgtctgt cggcgatagg    120
gtcaccatca catgtcaggc ttcccagtcc atttccaatt atctcgcttg gtaccagcag    180
aagcctggaa aggtgcccaa actgttgatc taccgcgctt ccactctcgc tagtggcgtg    240
ccctcccggt ttagcggcag cggaagcggc acagatttca ctctgactat ctcctccctg    300
cagcctgagg acgtggctac ctactattgc caacagggct acgtgtctaa taacctggac    360
aatatctttg gaggcgggac cgaggtcgtg gtcaag                              396
```

ANTI-PODOCALYXIN ANTIBODIES AND METHODS OF USING THE SAME

RELATED APPLICATIONS

This application claims the benefit under 35 U.S.C. § 119 to U.S. Provisional Application No. 61/893,817, filed Oct. 21, 2013, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jan. 6, 2022, is named 7000_PCT_US_2_SL.txt and is 67,249 bytes in size.

FIELD OF THE INVENTION

The present invention is directed to compositions of matter useful for the treatment of cancer in mammals and to methods of using those compositions of matter for the same.

BACKGROUND OF THE INVENTION

Podocalyxin, a sialoglycoprotein, is thought to be the major constituent of the glycocalyx of podocytes. It is a member of the CD34 family of transmembrane sialomucins (Nielsen J S, McNagny K M (2008). J of Cell Science 121 (Pt 22): 3682-3692). It coats the secondary foot processes of the podocytes. It is negatively charged and thus functions to keep adjacent foot processes separated, thereby keeping the urinary filtration barrier open. This function is further supported by knockout studies in mice which reveal an essential role in podocyte morphogenesis (Doyonnas R. et al (2001). J Exp Med 194 (1): 13-27; Nielsen J S, McNagny K M (2009). J Am Soc Nephrol 20 (10): 1669-76). Podocalyxin is also upregulated in a number of cancers and is frequently associated with poor prognosis (Nielsen J S, McNagny K M (2009). supra; Somasiri A et al. (2004). Cancer Res 64 (15): 5068-73; Huntsman et al. U.S. 20100061978A1). In fact, overexpression of the anti-adhesin podocalyxin can be an independent predictor of breast cancer progression (Somasiri et al. Cancer Res. 2004 Aug. 1; 64(15):5068-73).

Sialylated, O-glycosylated glycoforms of podocalyxin expressed by colon carcinoma cells possess L-selectin and E-selectin binding activity, and appear to be associated with the metastasis of colon carcinoma cells (Thomas S N et al. (March 2009). Am J Physiol Cell Physiol 296 (3): C505-13; Konstantopoulos K et al. (2009). Annu Rev Biomed Eng 11: 177-202; Thomas S N et al. (2009). Biorheology 46 (3): 207-25). In addition, it has been reported that podocalyxin is a prognostic indicator of tumor metastasis (McNagny et al. U.S. Pat. No. 7,833,733), and may modulate cancer cell growth (Hunstman et al. U.S. 2010/0061978). As such, there is a need for antagonists of podocalyxin for the treatment of cancer.

SUMMARY OF THE INVENTION

The invention provides anti-podocalyxin antibodies or functional fragments thereof, and their method of use in the treatment of cancer.

In one aspect, the invention provides an antibody that binds, preferably specifically, to podocalyxin. Optionally, the antibody is a monoclonal antibody, antibody fragment, including Fab, Fab', F(ab')2, and Fv fragment, diabody, single domain antibody, chimeric antibody, humanized antibody, human antibody, bispecific antibody, single-chain antibody or antibody that competitively inhibits the binding of an anti-podocalyxin polypeptide antibody to its respective antigenic epitope.

In one aspect, an antibody that binds to podocalyxin is provided, wherein the antibody comprises at least one, two, three, four, five or six HVRs selected from the group:
(i) HVR-L1 comprising QASQSISNYLA (SEQ ID NO: 9) or alternatively comprising QSISNY (SEQ ID NO:17);
(ii) HVR-L2 comprising RASTLAS (SEQ ID NO: 10) or alternatively comprising RAS (SEQ ID NO:18);
(iii) HVR-L3 comprising QQGYVSNNLDNI (SEQ ID NO: 11);
(iv) HVR-H1 comprising SYAMG (SEQ ID NO: 6) or alternatively comprising GIDLSSYAMG (SEQ ID NO:12) or alternatively comprising GIDLSSYA (SEQ ID NO:13);
(v) HVR-H2 comprising FIYASGSIFYASWAKG (SEQ ID NO: 7) or alternatively comprising FIYASGSI (SEQ ID NO:14) or alternatively comprising IYASGSI (SEQ ID NO:15); and
(vi) HVR-H3 comprising AGYYFGGNYDLNL (SEQ ID NO: 8) or alternatively comprising ARAGYYFGGNYDLNL (SEQ ID NO:16).

In one aspect, an antibody that binds to podocalyxin is provided, wherein the antibody comprises at least one, two, three, four, five or six HVRs selected from the group:
(i) HVR-L1 comprising SANSNVRYIH (SEQ ID NO: 27) or alternatively comprising SNVRY (SEQ ID NO:28);
(ii) HVR-L2 comprising DTSKLSS (SEQ ID NO: 29) or alternatively comprising DTS (SEQ ID NO:30);
(iii) HVR-L3 comprising QQWISNPLT (SEQ ID NO:31);
(iv) HVR-H1 comprising SYVMH (SEQ ID NO:19) or alternatively comprising GYTFTSYVMH (SEQ ID NO:20) or alternatively comprising GYTFTSYV (SEQ ID NO:21);
(v) HVR-H2 comprising YIHPYNDGTNYNEKFKG (SEQ ID NO:22) or alternatively comprising YIHPYNDGT (SEQ ID NO:23) or alternatively comprising IHPYNDGT (SEQ ID NO:24); and
(vi) HVR-H3 comprising SWDWYFDV (SEQ ID NO:25) or alternatively comprising ARSWDWYFDV (SEQ ID NO:26).

In one embodiment, HVR-L1 of an antibody of the invention comprises the sequence of SEQ ID NO: 9, 17, 27, or 28. In one embodiment, HVR-L2 of an antibody of the invention comprises the sequence of SEQ ID NO: 10, 18, 29, or 30. In one embodiment, HVR-L3 of an antibody of the invention comprises the sequence of SEQ ID NO: 11 or 31. In one embodiment, HVR-H1 of an antibody of the invention comprises the sequence of SEQ ID NO: 6, 12, 13, 19, 20, or 21. In one embodiment, HVR-H2 of an antibody of the invention comprises the sequence of SEQ ID NO: 7, 14, 15, 22, 23, or 24. In one embodiment, HVR-H3 of an antibody of the invention comprises the sequence of SEQ ID NO: 8, 16, 25, or 26.

In one embodiment, HVR-L1 of an antibody of the invention comprises the sequence of SEQ ID NO: 9 or 17. In one embodiment, HVR-L2 of an antibody of the invention comprises the sequence of SEQ ID NO: 10 or 18. In one embodiment, HVR-L3 of an antibody of the invention comprises the sequence of SEQ ID NO: 11. In one embodiment, HVR-H1 of an antibody of the invention comprises the sequence of SEQ ID NO: 6, 12 or 13. In one embodiment, HVR-H2 of an antibody of the invention comprises the sequence of SEQ ID NO: 7, 14 or 15. In one embodiment, HVR-H3 of an antibody of the invention comprises the sequence of SEQ ID NO: 8 or 16.

In one embodiment, HVR-L1 of an antibody of the invention comprises the sequence of SEQ ID NO: 27 or 28. In one embodiment, HVR-L2 of an antibody of the invention comprises the sequence of SEQ ID NO: 29 or 30. In one embodiment, HVR-L3 of an antibody of the invention comprises the sequence of SEQ ID NO: 31. In one embodiment, HVR-H1 of an antibody of the invention comprises the sequence of SEQ ID NO: 19, 20 or 21. In one embodiment, HVR-H2 of an antibody of the invention comprises the sequence of SEQ ID NO: 22, 23 or 24. In one embodiment, HVR-H3 of an antibody of the invention comprises the sequence of SEQ ID NO: 25 or 26.

In one embodiment, an antibody of the invention comprising these sequences (in combination as described herein) is a humanized or human antibody.

In one aspect, the invention provides an anti-podocalyxin antibody comprising a heavy chain variable region comprising the heavy chain variable region amino acid sequence depicted in FIG. 2. In one aspect, the invention provides an antibody comprising a heavy chain comprising an HVR-H1, HVR-H2 and/or HVR-H3 from the heavy chain variable region amino acid sequence depicted in FIG. 2. In one aspect, the invention provides an antibody comprising a light chain variable region comprising the light chain variable region amino acid sequence depicted in FIG. 2. In one aspect, the invention provides an antibody comprising a light chain comprising an HVR-L1, HVR-L2 and/or HVR-L3 from the light chain variable region amino acid sequence depicted in FIG. 2.

In one aspect, the invention includes an anti-podocalyxin antibody comprising (i) a heavy chain variable domain comprising SEQ ID NO: 3; and/or (ii) a light chain variable domain comprising SEQ ID NO: 5.

In one aspect, the invention includes an anti-podocalyxin antibody comprising (i) a heavy chain variable domain comprising SEQ ID NO:39; and/or (ii) a light chain variable domain comprising SEQ ID NO:41.

In one aspect, the invention includes an anti-podocalyxin antibody comprising (i) a heavy chain variable domain comprising SEQ ID NO:35; and/or (ii) a light chain variable domain comprising SEQ ID NO:33.

In one aspect, the invention includes an anti-podocalyxin antibody comprising (i) a heavy chain variable domain comprising SEQ ID NO:37; and/or (ii) a light chain variable domain comprising SEQ ID NO:33.

In one aspect, the invention provides an anti-podocalyxin antibody comprising a heavy chain variable region comprising the heavy chain variable region amino acid sequence depicted in FIG. 10F. In one aspect, the invention provides an antibody comprising a heavy chain comprising an HVR-H1, HVR-H2 and/or HVR-H3 from the heavy chain variable region amino acid sequence depicted in FIG. 10F. In one aspect, the invention provides an antibody comprising a light chain variable region comprising the light chain variable region amino acid sequence depicted in FIG. 10B. In one aspect, the invention provides an antibody comprising a light chain comprising an HVR-L1, HVR-L2 and/or HVR-L3 from the light chain variable region amino acid sequence depicted in FIG. 10B.

In one aspect, the invention provides an anti-podocalyxin antibody comprising a heavy chain variable region comprising the heavy chain variable region amino acid sequence depicted in FIG. 10H or J. In one aspect, the invention provides an antibody comprising a heavy chain comprising an HVR-H1, HVR-H2 and/or HVR-H3 from the heavy chain variable region amino acid sequence depicted in FIG. 10H or J. In one aspect, the invention provides an antibody comprising a light chain variable region comprising the light chain variable region amino acid sequence depicted in FIG. 10D. In one aspect, the invention provides an antibody comprising a light chain comprising an HVR-L1, HVR-L2 and/or HVR-L3 from the light chain variable region amino acid sequence depicted in FIG. 10D.

In one aspect, the invention provides an anti-podocalyxin antibody comprising a heavy chain variable region comprising the heavy chain variable region amino acid sequence depicted in FIG. 11B. In one aspect, the invention provides an antibody comprising a heavy chain comprising an HVR-H1, HVR-H2 and/or HVR-H3 from the heavy chain variable region amino acid sequence depicted in FIG. 11B. In one aspect, the invention provides an antibody comprising a light chain variable region comprising the light chain variable region amino acid sequence depicted in FIG. 11D. In one aspect, the invention provides an antibody comprising a light chain comprising an HVR-L1, HVR-L2 and/or HVR-L3 from the light chain variable region amino acid sequence depicted in FIG. 11D.

In one aspect, the invention provides an anti-podocalyxin antibody comprising a heavy chain variable region comprising the heavy chain variable region amino acid sequence depicted in FIG. 11F or H. In one aspect, the invention provides an antibody comprising a heavy chain comprising an HVR-H1, HVR-H2 and/or HVR-H3 from the heavy chain variable region amino acid sequence depicted in FIG. 11F or H. In one aspect, the invention provides an antibody comprising a light chain variable region comprising the light chain variable region amino acid sequence depicted in FIG. 11J. In one aspect, the invention provides an antibody comprising a light chain comprising an HVR-L1, HVR-L2 and/or HVR-L3 from the light chain variable region amino acid sequence depicted in FIG. 11J.

In one aspect, the invention provides an anti-podocalyxin antibody comprising a heavy chain variable region comprising the heavy chain variable region amino acid sequence depicted in FIG. 12A. In one aspect, the invention provides an antibody comprising a heavy chain comprising an HVR-H1, HVR-H2 and/or HVR-H3 from the heavy chain variable region amino acid sequence depicted in FIG. 12A. In one aspect, the invention provides an antibody comprising a light chain variable region comprising the light chain variable region amino acid sequence depicted in FIG. 12C. In one aspect, the invention provides an antibody comprising a light chain comprising an HVR-L1, HVR-L2 and/or HVR-L3 from the light chain variable region amino acid sequence depicted in FIG. 12C.

In one aspect, the invention provides an anti-podocalyxin antibody that binds preferentially to podocalyxin as compared to endoglycan and/or CD34.

In one embodiment, the anti-podocalyxin antibodies preferably (i) inhibit the growth or proliferation of a cell to which they bind; (ii) induce the death of a cell to which they bind; (iii) inhibit the delamination of a cell to which they bind; (iv) inhibit the metastasis of a cell to which they bind; or (v) inhibit the vascularization of a tumor comprising podocalyxin. For diagnostic purposes, the antibodies of the present invention may be detectably labeled, attached to a solid support, or the like.

In one aspect, the invention provides methods for making an antibody of the invention. For example, the invention provides a method of making a podocalyxin antibody (which, as defined herein, includes full length antibody and fragments thereof), said method comprising expressing in a suitable host cell a recombinant vector of the invention encoding said antibody, and recovering said antibody.

In one aspect, the invention is a pharmaceutical formulation comprising an antibody of the invention, and a pharmaceutically acceptable diluent, carrier or excipient.

In one aspect, the invention provides an article of manufacture comprising a container; and a composition contained within the container, wherein the composition comprises one or more podocalyxin antibodies of the invention.

In one aspect, the invention provides a kit comprising a first container comprising a composition comprising one or more podocalyxin antibodies of the invention; and a second container comprising a buffer.

In one aspect, the invention provides use of a podocalyxin antibody of the invention in the preparation of a medicament for the therapeutic and/or prophylactic treatment of a disease, such as a cancer, a tumor and/or a cell proliferative disorder.

In one aspect, the invention provides use of an article of manufacture of the invention in the preparation of a medicament for the therapeutic and/or prophylactic treatment of a disease, such as a cancer, a tumor and/or a cell proliferative disorder.

In one aspect, the invention provides use of a kit of the invention in the preparation of a medicament for the therapeutic and/or prophylactic treatment of a disease, such as a cancer, a tumor and/or a cell proliferative disorder.

In one aspect, the invention provides a method of inhibiting the growth of a cell that expresses podocalyxin, said method comprising contacting said cell with an antibody of the invention thereby causing an inhibition of growth of said cell. In one embodiment, the cell is contacted with the antibody in vitro. In another embodiment, the cell is contacted with the antibody in vivo.

In one aspect, the invention provides a method of therapeutically treating a mammal having a cancerous tumor comprising a cell that expresses podocalyxin, said method comprising administering to said mammal a therapeutically effective amount of an antibody of the invention, thereby effectively treating said mammal.

In one aspect, the invention provides a method for treating or preventing a cell proliferative disorder associated with increased expression of podocalyxin, said method comprising administering to a subject in need of such treatment an effective amount of an antibody of the invention, thereby effectively treating or preventing said cell proliferative disorder. In one embodiment, said proliferative disorder is cancer.

In one aspect, the invention provides a method for inhibiting the growth of a cell, wherein growth of said cell is at least in part dependent upon podocalyxin, said method comprising contacting said cell with an effective amount of an antibody of the invention, thereby inhibiting the growth of said cell.

In one aspect, the invention provides a method of treating cancer comprising administering to a patient the pharmaceutical formulation comprising an antibody described herein, acceptable diluent, carrier or excipient.

In one aspect, the invention provides a method of inhibiting the vascularization of a tumor, comprising administering to a patient the pharmaceutical formulation comprising an antibody described herein, acceptable diluent, carrier or excipient.

In one aspect, the invention provides a method of inhibiting the delamination of cells expressing podocalyxin, comprising administering to a patient the pharmaceutical formulation comprising an antibody described herein, acceptable diluent, carrier or excipient.

In one aspect, the invention provides a method of inhibiting tumor metastasis in a patient having cancer, comprising administering to a patient the pharmaceutical formulation comprising an antibody described herein, acceptable diluent, carrier or excipient.

In one aspect, the invention provides a method of decreasing tumor size, comprising administering to a patient the pharmaceutical formulation comprising an antibody described herein, acceptable diluent, carrier or excipient.

In one aspect, the invention provides a method of determining the presence of podocalyxin in a sample suspected of containing podocalyxin, said method comprising exposing said sample to an antibody of the invention, and determining binding of said antibody to podocalyxin in said sample wherein binding of said antibody to podocalyxin in said sample is indicative of the presence of said protein in said sample.

In one aspect, the invention provides a method of diagnosing a cancer associated with an increase in podocalyxin expression in a tumor. In one embodiment, the method comprises contacting cells in a biological test sample with any of the antibodies described herein; determining the level of antibody bound to cells in the test sample by detecting binding of the antibody to podocalyxin; and comparing the level of antibody bound to cells in a control sample, wherein a higher level of antibody bound in the test sample as compared to the control sample indicates the presence of a cancer associated with cells expressing podocalyxin. In one embodiment, the method involves normalization to the number of cells in the test and control samples.

In another aspect, the present invention provides a method of determining cancer patient prognosis. In one embodiment, the method includes the step of detecting a differential level of expression of podocalyxin in the patient sample, as compared to a control, wherein the differential expression is indicative of the patient's prognosis. In one embodiment, the method includes the step of detecting a higher level of expression of podocalyxin in the patient sample, as compared to a control, wherein the higher expression indicates that the patient has a poor prognosis. In one embodiment, the method includes the step of detecting a lower level of expression of podocalyxin in the patient sample, as compared to a control, wherein the lower expression indicates that the patient has a good prognosis.

In another aspect, the present invention provides a method of determining cancer patient risk of tumor metastasis. In one embodiment, the method includes the step of detecting a differential level of expression of podocalyxin in the patient sample, as compared to a control, wherein the differential expression is indicative of the patient's risk of tumor metastasis. In one embodiment, the method includes the step of detecting a higher level of expression of podocalyxin in the patent sample, as compared to a control, wherein the higher expression indicates that the patient has a higher risk of tumor metastasis. In one embodiment, the method includes the step of detecting a lower level of expression of podocalyxin in the patient sample, as compared to a control, wherein the lower expression indicates that the patient has a lower risk of tumor metastasis.

In another aspect, the present invention provides a method for monitoring the outcome of treatment after a subject is administered a therapeutic agent for the treatment of cancer. In one embodiment, the method includes the step of detecting a differential level of podocalyxin expression in a test sample, as compared to a control, obtained from the subject who has been treated for cancer, wherein the differential level of expression is indicative of the outcome of treatment of the subject. In one other embodiment, the method includes the step of detecting a lower level of podocalyxin expression in a test sample, as compared to a control, obtained from the subject who has been treated for cancer, wherein the lower level of expression is indicative of a positive outcome of treatment of the subject. In one other embodiment, the method includes the step of detecting a higher level of podocalyxin expression in a test sample, as compared to a control, obtained from the subject who has been treated for cancer, wherein the higher level of expression is indicative of a negative outcome of treatment of the subject.

In another aspect the invention provides a method of assessing whether a sample from a patient with cancer indicates responsiveness of the patient to treatment with an anti-cancer agent. In one embodiment, the method includes the step of detecting a differential level of expression of podocalyxin in the sample, as compared to a control, wherein the differential expression is indicative of the responsiveness of the patient to the treatment. In one embodiment, the method includes the step of detecting a lower level of expression of podocalyxin in the sample, as compared to a control, wherein the lower expression indicates that the patient is responsive to the treatment. In one embodiment, the method includes the step of detecting a higher level of expression of podocalyxin in the sample, as compared to a control, wherein the higher expression indicates that the patient is not responsive to the treatment. In another embodiment, the differential level of expression is indicative of metastatic propensity. In one embodiment, a higher expression indicates a higher propensity. In another embodiment, a lower expression indicates a lower propensity.

BRIEF DESCRIPTION OF THE DRAWINGS

FIG. 1 provides the amino acid sequences of human podocalyxin isoforms—SEQ ID NOS: 1 and 42 (NCBI Accession Nos. NP 001018121.1 and NP 005388.2).

FIG. 2 provides the nucleic acid sequence for the heavy chain variable region (SEQ ID NO:2); the amino acid sequence for the heavy chain variable region (SEQ ID NO:3); the nucleic acid sequence for the light chain variable region (SEQ ID NO:4); and the amino acid sequence for the light chain variable region (SEQ ID NO:5) of the anti-podocalyxin antibody anti-PODO (also referred to herein as Ab-1) (see Examples). Hypervariable regions are underlined for the heavy chain variable region (SEQ ID NOS: 6-8) and light chain variable region (SEQ ID NOS: 9-11) in accordance with Kabat numbering are depicted.

FIG. 6 A-F provides representative images of excised tumors, quantitation of tumor size and assessment of tumor cell movement from the site of injection. MDA.MB-231$^{RFP}$ cells were pre-incubated with 25 µg of anti-PODO (anti-PODO$^{PT}$) (Rb/Hu Podo83) or anti-OVA control (anti-OVA$^{PT}$) per $10^6$ cells for 30 minutes at room temperature in vitro. A total of $1\times10^6$ anti-PODO$^{PT}$ or anti-OVA$^{PT}$ MDA.MB-231$^{RFP}$ cells in a 2:1 mixture of Matrigel™ and HBSS were subcutaneously injected into the flanks of NSG mice. Starting on day 14 post-transplantation, 100 µg of anti-OVA (anti-OVA$^{sys}$) or anti-PODO (anti-PODO$^{sys}$) antibody (Rb/Hu Podo83) was intraperitoneally (i.p.) injected into NSG mice twice weekly. (A) Representative images of anti-OVA$^{PT}$ tumors treated with either anti-OVA$^{sys}$ control or anti-PODO$^{sys}$. (B) Weight (g) of anti-OVA$^{PT}$ tumors treated with either anti-OVA$^{sys}$ control or anti-PODO$^{sys}$ antibody (C) Number of RFP-positive tumor cells per $10^6$ lung cells of mice with anti-OVA$^{PT}$ tumors systemically treated with either anti-OVA control or anti-PODO antibody as detected by flow cytometry. (D) Representative images of anti-PODO$^{PT}$ tumors systemically treated with either anti-OVA control or anti-PODO antibody. (E) Weight (g) of anti-PODO$^{PT}$ tumors systemically treated with either anti-OVA control or anti-PODO antibody. (F) Number of RFP-positive tumor cells per $10^6$ lung cells of mice with anti-PODO$^{PT}$ tumors treated with either anti-OVA$^{sys}$ control or anti-PODO$^{sys}$ as detected by flow cytometry.

Figure 8C:
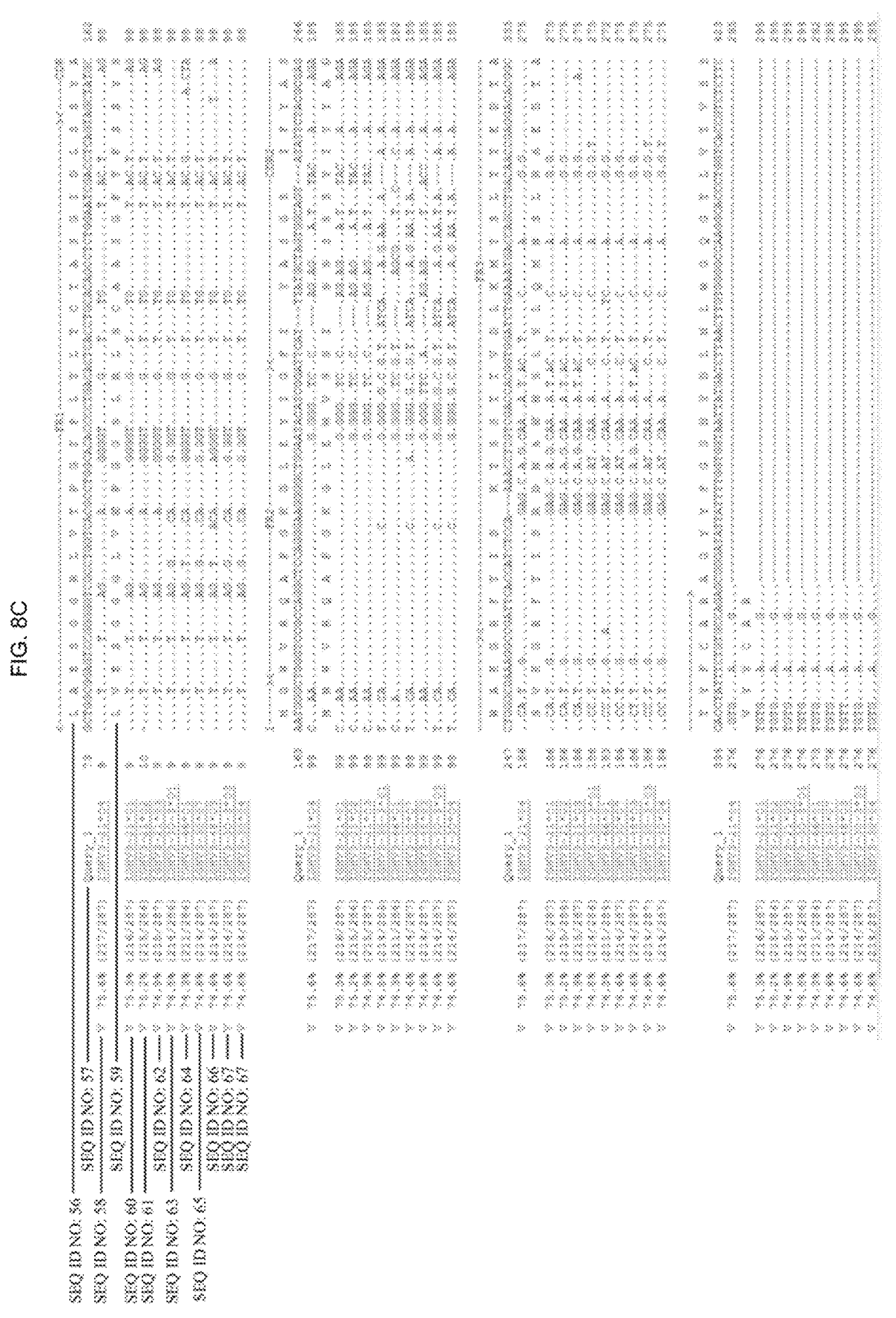

FIG. 8A-D show the sequence comparisons alignments of the human immunoglobulin light chain and heavy chain variable sequences to the rabbit Ab-1 sequences ("Query 1"). FIGS. 8A and 8C show the alignments of the human immunoglobulin light chain and heavy chain variable sequences, respectively, obtained from the IMGT database, and the respective rabbit Ab-1 sequences. FIG. 8A discloses SEQ ID NOS 43-48, and 48-52, respectively, in order of appearance and FIG. 8C discloses SEQ ID NOS 56-67, and 67, respectively, in order of appearance. FIG. 8B compares the amino acid sequences of the rabbit Ab-1 ("Podo 83") light chain variable region and the selected human IGKV1-27*01 sequence and shows their consensus sequence, and FIG. 8D compares the amino acid sequences of the rabbit Ab-1 ("Podo 83") heavy chain variable region and the selected human IGHV3-66*01 sequence and shows their consensus sequence. FIG. 8B discloses SEQ ID NOS 53-55, respectively, in order of appearance and FIG. 8D discloses SEQ ID NOS 68-70, respectively, in order of appearance.

FIG. 9B discloses SEQ ID NOS 73, 69, and 74, respectively, in order of appearance.

FIG. 10A-J show the original rabbit and humanized sequences used to clone the humanized light chain and heavy chain variable region constructs into the pTT5-hIgkC and pTT5-hIgHC plasmids that contain the respective constant region sequences. The Kozak sequences are underlined. The original rabbit light chain ("Podo_83_original") variable nucleotide and amino acid sequences are shown in (A) and (B), respectively. The humanized light chain variable ("Podo_83_humanized_light_ver_1") nucleotide and amino acid sequences are shown in (C) (SEQ ID NO:32) and (D) (SEQ ID NO:33), respectively. The original rabbit heavy chain ("Podo_83_original") variable nucleotide and amino acid sequences are shown in (E) and (F), respectively. Two versions of the humanized heavy chain variable region were created, 1:1 and 2:1. The nucleotide and amino acid sequences of the humanized heavy chain variable region of 1:1 ("Podo_83_humanized_ver_1") are shown in (G) (SEQ ID NO:34) and (H) (SEQ ID NO:35), respectively, while the nucleotide and amino acid sequences of the humanized heavy chain variable region of 2:1 ("Podo_83_ humanized_ver_2") are shown in (I) (SEQ ID NO:36) and (J) (SEQ ID NO:37), respectively. FIG. 10 discloses SEQ ID NOS 75, 5, 32, 33, 76, 3, 34, 35, 36, and 37, respectively, in order of appearance.

FIG. 11A-J show the sequences of the original rabbit and humanized sequences of the anti-podocalyxin antibodies produced. The original rabbit VH nucleotide and amino acid sequence are shown in (A) and (B), respectively, and the Vk nucleotide and amino acid sequences are shown in (C) and (D), respectively. The nucleotide and amino acid sequences of the humanized VH of 1:1 are shown in (E) and (F), respectively, and the humanized VH of 2:1 are shown in (G) and (H), respectively. The humanized Vk nucleotide and amino acid sequences are shown in (I) and (J), respectively. The underlined, italicized regions correspond to the leader sequence. FIG. 11 discloses SEQ ID NOS 2, 3, 4, 5, 77, 35, 78, 37, 79, and 33, respectively, in order of appearance.

FIG. 12A-D show the VH and Vk sequences of the mouse 3G2 antibody. (A) shows the VH amino acid sequence (SEQ ID NO:39), (B) shows the VH nucleotide sequence (SEQ ID NO:38), (C) shows the Vk amino acid sequence (SEQ ID NO:41), and (D) shows the Vk nucleotide sequence (SEQ ID NO:40). The underlined, italicized regions correspond to the leader sequence.

DETAILED DESCRIPTION OF THE INVENTION

Figure 3:
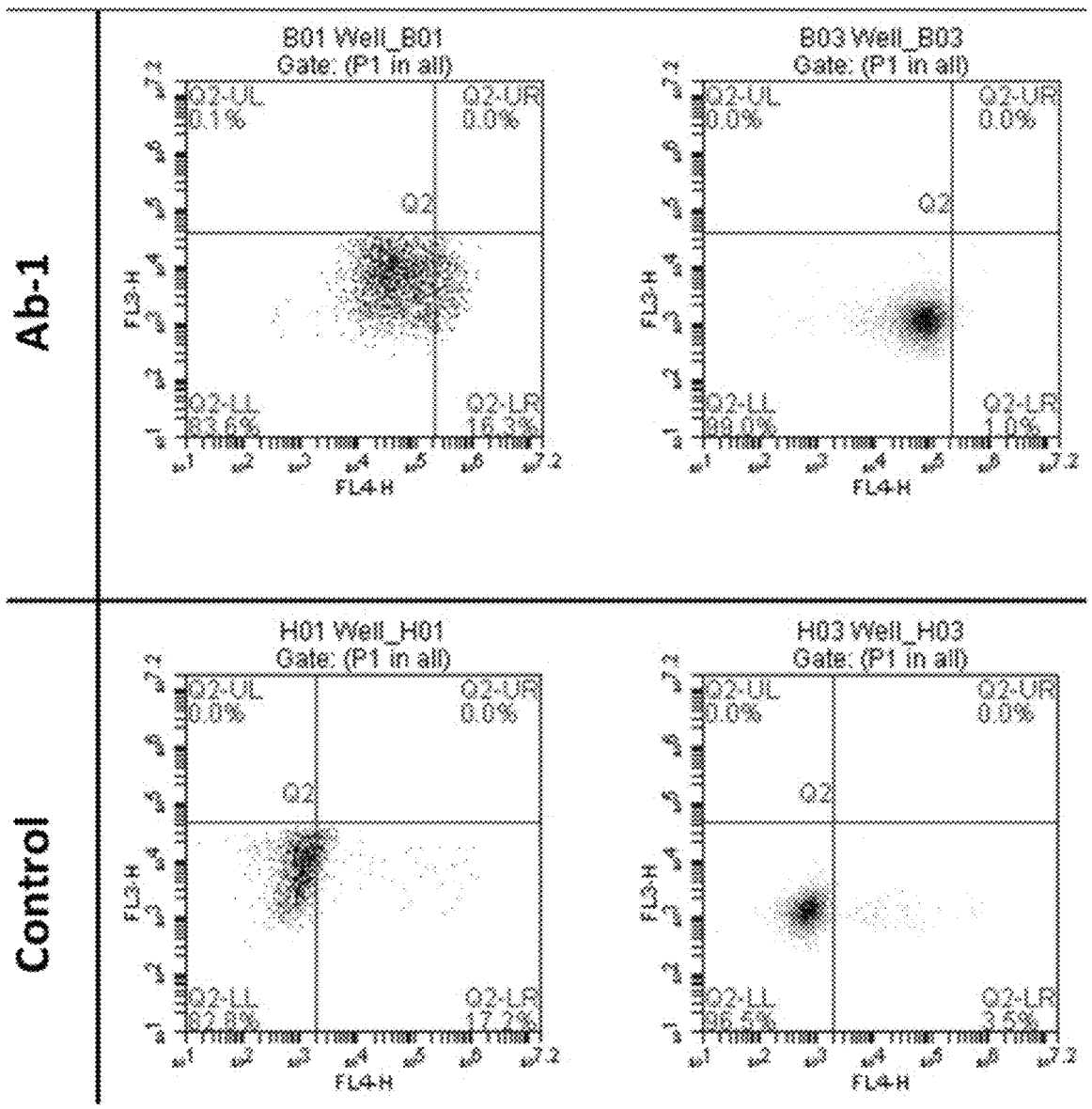
FIG. 3A demonstrates the specificity of the anti-PODO antibody (Rb/Hu Podo83) against various prodocalyxin-expressing cell lines. (A) FACS analysis of MDA-MB-231 and MDA-MB-231/hPodo transfectant staining.

The invention provides methods, compositions, kits and articles of manufacture useful for the treatment of cancer in mammals.

Details of these methods, compositions, kits and articles of manufacture are provided herein.

I. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

II. Definitions

For purposes of interpreting this specification, the following definitions will apply and whenever appropriate, terms used in the singular will also include the plural and vice versa. In the event that any definition set forth conflicts with any document incorporated herein by reference, the definition set forth below shall control.

The term "podocalyxin", as used herein, refers to any native podocalyxin from any vertebrate source, including mammals such as primates (e.g. humans, primates, and rodents (e.g., mice and rats)), unless otherwise indicated. The podocalyxin molecule is also referred to as podocalyxin-like protein 1, PC, PCLP1, gp135, MEP21, and thrombomucin. Human podocalyxin is encoded by the nucleotide sequence corresponding to Accession Nos. NM_001018111.2 and NM_005397.3. Isoforms of podocalyxin include a 558 amino acid polypeptide (Accession: NP_001018121.1) and a 526 amino acid polypeptide (Accession No. NP_005388.2).

The term "podocalyxin" encompasses "full-length," unprocessed podocalyxin as well as any form of podocalyxin that results from processing in the cell. The term also encompasses naturally occurring variants of podocalyxin, e.g., splice variants, allelic variants and isoforms. "Podocalyxin" and "podocalyxin polypeptide" include any post-translational modification (e.g., glycosylation, sialylation, etc.). The podocalyxin polypeptides described herein may be isolated from a variety of sources, such as from human tissue types or from another source, or prepared by recombinant or synthetic methods. The amino acid sequence of human podocalyxin includes sequences corresponding to SEQ ID NO: 1 or 42 (FIG. 1). A "native sequence podocalyxin polypeptide" comprises a polypeptide having the same amino acid sequence as the corresponding podocalyxin polypeptide derived from nature. Such native sequence podocalyxin polypeptides can be isolated from nature or can be produced by recombinant or synthetic means. The term "native sequence podocalyxin polypeptide" specifically encompasses naturally-occurring truncated or secreted forms of the specific podocalyxin polypeptide (e.g., an extracellular domain sequence), naturally-occurring variant forms (e.g., alternatively spliced forms) and naturally-occurring allelic variants of the polypeptide. In certain embodiments of the invention, the native sequence podocalyxin polypeptides disclosed herein are mature or full-length native sequence polypeptides comprising the full-length amino acid sequences shown in the accompanying figures. Although the podocalyxin polypeptides disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the podocalyxin polypeptides.

A "modification" of an amino acid residue/position, as used herein, refers to a change of a primary amino acid sequence as compared to a starting amino acid sequence, wherein the change results from a sequence alteration involving said amino acid residue/positions. For example, typical modifications include substitution of the residue (or at said position) with another amino acid (e.g., a conservative or non-conservative substitution), insertion of one or more (generally fewer than 5 or 3) amino acids adjacent to said residue/position, and deletion of said residue/position. An "amino acid substitution", or variation thereof, refers to the replacement of an existing amino acid residue in a predetermined (starting) amino acid sequence with a different amino acid residue. Generally and preferably, the modification results in alteration in at least one physicobiochemical activity of the variant polypeptide compared to a polypeptide comprising the starting (or "wild type") amino acid sequence. For example, in the case of an antibody, a physicobiochemical activity that is altered can be binding affinity, binding capability and/or binding effect upon a target molecule.

The term "antibody" is used in the broadest sense and specifically covers, for example, single anti-podocalyxin monoclonal antibodies (including agonist, antagonist, neutralizing antibodies, full length or intact monoclonal antibodies), anti-podocalyxin antibody compositions with poly-epitopic specificity, polyclonal antibodies, multivalent antibodies, multispecific antibodies (e.g., bispecific antibodies so long as they exhibit the desired biological activity), formed from at least two intact antibodies, single chain anti-podocalyxin antibodies, and fragments of anti-podocalyxin antibodies (see below), including Fab, Fab', F(ab')2 and Fv fragments, diabodies, single domain antibodies (sd-Abs), as long as they exhibit the desired biological or immunological activity. The term "immunoglobulin" (Ig) is used interchangeable with antibody herein. An antibody can be human, humanized and/or affinity matured.

The term "anti-podocalyxin antibody", "podocalyxin antibody", or "an antibody that binds to podocalyxin" or "antibody of the invention" refers to an antibody that is capable of binding podocalyxin with sufficient affinity such that the antibody is useful as a diagnostic and/or therapeutic agent in targeting podocalyxin. In certain embodiments, anti-podocalyxin antibody binds to an epitope of podocalyxin that is conserved among podocalyxin from different species. Anti-podocalyxin antibody of the invention preferably binds preferentially to podocalyxin as compared to endoglycan and/or CD34. Highly preferred are anti-podocalyxin antibodies exhibiting little or no cross reactivity with endoglycan or CD34.

In one embodiment, a "podocalyxin antibody" is used herein to specifically refer to an anti-podocalyxin monoclonal antibody that (i) comprises the heavy chain variable domain of SEQ ID NO: 3 (FIG. 2) and/or the light chain variable domain of SEQ ID NO: 5 (FIG. 2); or (ii) comprises one, two, three, four, five, or six of the CDRs shown as SEQ ID NOS: 6-11 (FIG. 2).

An "isolated antibody" is one which has been identified and separated and/or recovered from a component of its natural environment. Contaminant components of its natural environment are materials which would interfere with therapeutic uses for the antibody, and may include enzymes, hormones, and other proteinaceous or nonproteinaceous solutes.

The basic 4-chain antibody unit is a heterotetrameric glycoprotein composed of two identical light (L) chains and two identical heavy (H) chains. In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in CH sequence and function, e.g., humans express the following subclasses: IgG1, IgG2, IgG3, IgG4, IgA1, and IgA2. The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)).

An "intact" antibody is one which comprises an antigen-binding site as well as a CL and at least heavy chain constant domains, CH1, CH2 and CH3. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. In one embodiment, an antibody fragment comprises an antigen binding site of the intact antibody and thus retains the ability to bind antigen.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra. Also included within the scope of the invention are chimeric antigen receptors (CARs) comprising VH and VL antibody domains of the invention (see for example Pule, M; Finney H; Lawson A (2003). "Artificial T-cell receptors". Cytotherapy 5 (3): 211-26).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
| --- | --- | --- | --- | --- |
| L1 | L24-L34 | L24-L34 | L24-L34 | L30-L36 |
| L2 | L50-L56 | L50-L56 | L50-L56 | L46-L55 |
| L3 | L89-L97 | L89-L97 | L89-L97 | L89-L96 |
| H1 | H31-H35B | H26-H35B | H26-H32.34 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H52-H56 | H47-H58 |
| H3 | H95-H102 | H95-H102 | H95-H102 | H93-H101 |

Hypervariable regions may comprise "extended hypervariable regions" as follows: 24-36 or 24-34 (L1), 46-56 or 50-56 (L2) and 89-97 (L3) in the VL and 26-35B (H1), 50-65, 47-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues herein defined.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system.

An additional system for defining light chain and heavy chain CDRs is provided by IMGT®, the international ImMunoGeneTics information system® www.imgt.org.

A "blocking" antibody or an "antagonist" antibody is one which inhibits or reduces biological activity of the antigen it binds. Preferred blocking antibodies or antagonist antibodies substantially or completely inhibit the biological activity of the antigen.

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

An antibody "which binds" an antigen of interest, e.g. a podocalyxin polypeptide antigen target, is one that binds the antigen with sufficient affinity such that the antibody is useful as a therapeutic agent in targeting a cell or tissue expressing the antigen, and does not significantly cross-react with other proteins. With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. In one embodiment, the term "specific binding" refers to binding where a molecule binds to a particular polypeptide or epitope on a particular polypeptide without substantially binding to any other polypeptide or polypeptide epitope.

An antibody that "inhibits the growth of tumor cells expressing a podocalyxin polypeptide" or a "growth inhibitory" antibody is one which results in measurable growth inhibition of cancer cells expressing or overexpressing the appropriate podocalyxin polypeptide. The podocalyxin polypeptide may be a transmembrane polypeptide expressed on the surface of a cancer cell or may be a polypeptide that is produced and secreted by a cancer cell. Preferred growth inhibitory anti-podocalyxin antibodies inhibit growth of podocalyxin-expressing tumor cells by greater than 20%, preferably from about 20% to about 50%, and even more preferably, by greater than 50% (e.g., from about 50% to about 100%) as compared to the appropriate control, the control typically being tumor cells not treated with the antibody being tested.

Antibodies that "inhibit the growth of tumor cells expressing a podocalyxin polypeptide" may also (i) inhibit the growth or proliferation of a cell to which they bind; (ii) induce the death of a cell to which they bind; (iii) inhibit the delamination of a cell to which they bind; (iv) inhibit the metastasis of a cell to which they bind; or (v) inhibit the vascularization of a tumor comprising a podocalyxin expressing cell.

The term "antagonist" is used in the broadest sense, and includes any molecule that partially or fully blocks, inhibits, or neutralizes a biological activity of a native podocalyxin polypeptide. Suitable antagonist molecules specifically include antagonist antibodies or antibody fragments, fragments or amino acid sequence variants of native podocalyxin polypeptides, peptides, antisense oligonucleotides, small organic molecules, etc. Methods for identifying antagonists of a podocalyxin polypeptide, may comprise contacting a podocalyxin polypeptide, with a candidate antagonist molecule and measuring a detectable change in one or more biological activities normally associated with the podocalyxin polypeptide.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer (e.g., pancreatic ductal adenocarcinoma) including neuroendocrine pancreatic cancer, glioblastoma, cervical cancer, ovarian cancer (e.g., high grade serous ovarian carcinoma), liver cancer (e.g., hepatocellular carcinoma (HCC)), bladder cancer (e.g., urothelial bladder cancer), testicular (germ cell tumour) cancer, hepatoma, breast cancer, brain cancer (e.g., astrocytoma), colon cancer, rectal cancer, colorectal cancer, endometrial or uterine carcinoma, salivary gland carcinoma, kidney or renal cancer (e.g., renal cell carcinoma, nephroblastoma or Wilms' tumour), prostate cancer including neuroendocrine prostate cancer, vulval cancer, thyroid cancer, hepatic carcinoma, anal carcinoma, penile carcinoma, as well as head and neck cancer. Additional examples of cancer include, without limitation, retinoblastoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, and urinary tract carcinomas. See, for example, McNagny et al., Podocalyxin in the Diagnosis and Treatment of Cancer, Chapter 8, Advances in Cancer Management, Edited by Ravinder Mohan, ISBN 978-953-307-870-0, Jan. 27, 2012, which is incorporated herein by reference.

In a preferred embodiment, the cancer is breast cancer including, without limitation, invasive breast carcinoma, ductal breast carcinoma, and triple negative breast cancer.

The term "metastatic cancer" means the state of cancer where the cancer cells of a tissue of origin are transmitted from the original site to one or more sites elsewhere in the body, by the blood vessels or lymphatics, to form one or more secondary tumors in one or more organs besides the tissue of origin. A prominent example is metastatic breast cancer.

As used herein, a "podocalyxin-associated cancer" is a cancer that is associated with over-expression of a podocalyxin gene or gene product, which can be any cancer that is characterized by cells that express a higher level of one or more podocalyxin gene products, relative to suitable control cells. Suitable control cells can be cells from an individual who is not affected with a podocalyxin over-expressing cancer, or they may be non-cancerous cells from either the subject in need, or they may be non-cancerous cells from another individual who is affected with a podocalyxin over-expressing cancer.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues. Tumor includes the vasculature associated with a neoplasm.

The terms "predictive" and "prognostic" as used herein are also interchangeable, in the sense of meaning that the methods for prediction or prognostication are to allow the person practicing the method to select patients that are deemed (usually in advance of treatment, but not necessarily) more likely to respond to treatment with an anti-cancer agent, including an anti-podocalyxin antibody.

III. Compositions and Methods of the Invention

The invention provides anti-podocalyxin antibodies or functional fragments thereof, and their method of use in the treatment of cancer.

In one aspect, the invention provides an antibody which binds, preferably specifically, to podocalyxin. Optionally, the antibody is a monoclonal antibody, antibody fragment, including Fab, Fab', F(ab')2, and Fv fragment, diabody, single domain antibody, chimeric antibody, humanized antibody, single-chain antibody or antibody that competitively inhibits the binding of an anti-podocalyxin polypeptide antibody to its respective antigenic epitope.

In one aspect, a functional anti-podocalyxin antibody is provided, wherein the antibody has one or more of the following activities: (i) inhibits delamination; (ii) inhibits tumor metastasis in vivo; (iii) inhibits tumor growth in vivo; (iv) decreases tumor size in vivo; (v) inhibits tumor vascularization in vivo; (vi) exhibits cytotoxic activity on tumor cell expressing podocalyxin in vivo; or (vii) exhibits cytostatic activity on tumor cell expressing podocalyxin in vivo.

In one aspect, an antibody that binds to podocalyxin is provided, wherein the antibody comprises:
(a) at least one, two, three, four, five or six HVRs selected from the group consisting of:
(i) HVR-L1 comprising QASQSISNYLA (SEQ ID NO: 9) or alternatively comprising QSISNY (SEQ ID NO:17);

(ii) HVR-L2 comprising RASTLAS (SEQ ID NO: 10) or alternatively comprising RAS (SEQ ID NO:18);
(iii) HVR-L3 comprising QQGYVSNNLDNI (SEQ ID NO: 11);
(iv) HVR-H1 comprising SYAMG (SEQ ID NO: 6) or alternatively comprising GIDLSSYAMG (SEQ ID NO:12) or alternatively comprising GIDLSSYA (SEQ ID NO:13);
(v) HVR-H2 comprising FIYASGSIFYASWAKG (SEQ ID NO: 7) or alternatively comprising FIYASGSI (SEQ ID NO:14) or alternatively comprising IYASGSI (SEQ ID NO:15); and
(vi) HVR-H3 comprising AGYYFGGNYDLNL (SEQ ID NO: 8) or alternatively comprising ARAGYYFGGNYDLNL (SEQ ID NO:16).

In one aspect, an antibody that binds to podocalyxin is provided, wherein the antibody comprises at least one, two, three, four, five or six HVRs selected from the group consisting of:
(i) HVR-L1 comprising SANSNVRYIH (SEQ ID NO: 27) or alternatively comprising SNVRY (SEQ ID NO:28);
(ii) HVR-L2 comprising DTSKLSS (SEQ ID NO: 29) or alternatively comprising DTS (SEQ ID NO:30);
(iii) HVR-L3 comprising QQWISNPLT (SEQ ID NO:31);
(iv) HVR-H1 comprising SYVMH (SEQ ID NO:19) or alternatively comprising GYTFTSYVMH (SEQ ID NO:20) or alternatively comprising GYTFTSYV (SEQ ID NO:21);
(v) HVR-H2 comprising YIHPYNDGTNYNEKFKG (SEQ ID NO:22) or alternatively comprising YIHPYNDGT (SEQ ID NO:23) or alternatively comprising IHPYNDGT (SEQ ID NO:24); and
(vi) HVR-H3 comprising SWDWYFDV (SEQ ID NO:25) or alternatively comprising ARSWDWYFDV (SEQ ID NO:26).

In one embodiment, HVR-L1 of an antibody of the invention comprises the sequence of SEQ ID NO: 9, 17, 27, or 28. In one embodiment, HVR-L2 of an antibody of the invention comprises the sequence of SEQ ID NO: 10, 18, 29, or 30. In one embodiment, HVR-L3 of an antibody of the invention comprises the sequence of SEQ ID NO: 11 or 31. In one embodiment, HVR-H1 of an antibody of the invention comprises the sequence of SEQ ID NO: 6, 12, 13, 19, 20, or 21. In one embodiment, HVR-H2 of an antibody of the invention comprises the sequence of SEQ ID NO: 7, 14, 15, 22, 23, or 24. In one embodiment, HVR-H3 of an antibody of the invention comprises the sequence of SEQ ID NO: 8, 16, 25, or 26.

In one embodiment, HVR-L1 of an antibody of the invention comprises the sequence of SEQ ID NO: 9 or 17. In one embodiment, HVR-L2 of an antibody of the invention comprises the sequence of SEQ ID NO: 10 or 18. In one embodiment, HVR-L3 of an antibody of the invention comprises the sequence of SEQ ID NO: 11. In one embodiment, HVR-H1 of an antibody of the invention comprises the sequence of SEQ ID NO: 6, 12 or 13. In one embodiment, HVR-H2 of an antibody of the invention comprises the sequence of SEQ ID NO: 7, 14 or 15. In one embodiment, HVR-H3 of an antibody of the invention comprises the sequence of SEQ ID NO: 8 or 16.

In one embodiment, HVR-L1 of an antibody of the invention comprises the sequence of SEQ ID NO: 27 or 28. In one embodiment, HVR-L2 of an antibody of the invention comprises the sequence of SEQ ID NO: 29 or 30. In one embodiment, HVR-L3 of an antibody of the invention comprises the sequence of SEQ ID NO: 31. In one embodiment, HVR-H1 of an antibody of the invention comprises the sequence of SEQ ID NO: 19, 20 or 21. In one embodiment, HVR-H2 of an antibody of the invention comprises the sequence of SEQ ID NO: 22, 23 or 24. In one embodiment, HVR-H3 of an antibody of the invention comprises the sequence of SEQ ID NO: 25 or 26.

In one embodiment, an antibody of the invention comprising these sequences (in combination as described herein) is a humanized or human antibody.

In one aspect, the invention provides an anti-podocalyxin antibody comprising a heavy chain variable region comprising the heavy chain variable region amino acid sequence depicted in FIG. 2. In one aspect, the invention provides an antibody comprising a heavy chain comprising an HVR-H1, HVR-H2 and/or HVR-H3 from the heavy chain variable region amino acid sequence depicted in FIG. 2. In one aspect, the invention provides an antibody comprising a light chain variable region comprising the light chain variable region amino acid sequence depicted in FIG. 2. In one aspect, the invention provides an antibody comprising a light chain comprising an HVR-L1, HVR-L2 and/or HVR-L3 from the light chain variable region amino acid sequence depicted in FIG. 2.

In one aspect, the invention includes an anti-podocalyxin antibody comprising (i) a heavy chain variable domain comprising SEQ ID NO: 3; and/or (ii) a light chain variable domain comprising SEQ ID NO: 5.

In one aspect, the invention includes an anti-podocalyxin antibody comprising (i) a heavy chain variable domain comprising an amino acid sequence encoded by SEQ ID NO: 2; and/or (ii) a light chain variable domain comprising an amino acid sequence encoded by SEQ ID NO: 4.

In one aspect, the invention includes an anti-podocalyxin antibody comprising (i) a heavy chain variable domain comprising SEQ ID NO:39; and/or (ii) a light chain variable domain comprising SEQ ID NO:41.

In one aspect, the invention includes an anti-podocalyxin antibody comprising (i) a heavy chain variable domain comprising an amino acid sequence encoded by SEQ ID NO:38 2; and/or (ii) a light chain variable domain comprising an amino acid sequence encoded by SEQ ID NO: 40.

In one aspect, the invention includes an anti-podocalyxin antibody comprising (i) a heavy chain variable domain comprising SEQ ID NO:35; and/or (ii) a light chain variable domain comprising SEQ ID NO:33.

In one aspect, the invention includes an anti-podocalyxin antibody comprising (i) a heavy chain variable domain comprising an amino acid sequence encoded by SEQ ID NO: 34; and/or (ii) a light chain variable domain comprising an amino acid sequence encoded by SEQ ID NO: 32.

In one aspect, the invention includes an anti-podocalyxin antibody comprising (i) a heavy chain variable domain comprising SEQ ID NO:37; and/or (ii) a light chain variable domain comprising SEQ ID NO:33.

In one aspect, the invention includes an anti-podocalyxin antibody comprising (i) a heavy chain variable domain comprising an amino acid sequence encoded by SEQ ID NO: 36; and/or (ii) a light chain variable domain comprising an amino acid sequence encoded by SEQ ID NO: 32.

In one aspect, the invention provides an anti-podocalyxin antibody comprising a heavy chain variable region comprising the heavy chain variable region amino acid sequence depicted in FIG. 10F. In one aspect, the invention provides an antibody comprising a heavy chain comprising an HVR-H1, HVR-H2 and/or HVR-H3 from the heavy chain variable region amino acid sequence depicted in FIG. 10F. In one aspect, the invention provides an antibody comprising a light chain variable region comprising the light chain variable region amino acid sequence depicted in FIG. 10B. In one aspect, the invention provides an antibody comprising a light chain comprising an HVR-L1, HVR-L2 and/or HVR-L3 from the light chain variable region amino acid sequence depicted in FIG. 10B.

In one aspect, the invention provides an anti-podocalyxin antibody comprising a heavy chain variable region comprising the heavy chain variable region amino acid sequence depicted in FIG. 10H or J. In one aspect, the invention provides an antibody comprising a heavy chain comprising an HVR-H1, HVR-H2 and/or HVR-H3 from the heavy chain variable region amino acid sequence depicted in FIG. 10H or J. In one aspect, the invention provides an antibody comprising a light chain variable region comprising the light chain variable region amino acid sequence depicted in FIG. 10D. In one aspect, the invention provides an antibody comprising a light chain comprising an HVR-L1, HVR-L2 and/or HVR-L3 from the light chain variable region amino acid sequence depicted in FIG. 10D.

In one aspect, the invention provides an anti-podocalyxin antibody comprising a heavy chain variable region comprising the heavy chain variable region amino acid sequence depicted in FIG. 11B. In one aspect, the invention provides an antibody comprising a heavy chain comprising an HVR-H1, HVR-H2 and/or HVR-H3 from the heavy chain variable region amino acid sequence depicted in FIG. 11B. In one aspect, the invention provides an antibody comprising a light chain variable region comprising the light chain variable region amino acid sequence depicted in FIG. 11D. In one aspect, the invention provides an antibody comprising a light chain comprising an HVR-L1, HVR-L2 and/or HVR-L3 from the light chain variable region amino acid sequence depicted in FIG. 11D.

In one aspect, the invention provides an anti-podocalyxin antibody comprising a heavy chain variable region comprising the heavy chain variable region amino acid sequence depicted in FIG. 11F or H. In one aspect, the invention provides an antibody comprising a heavy chain comprising an HVR-H1, HVR-H2 and/or HVR-H3 from the heavy chain variable region amino acid sequence depicted in FIG. 11F or H. In one aspect, the invention provides an antibody comprising a light chain variable region comprising the light chain variable region amino acid sequence depicted in FIG. 11J. In one aspect, the invention provides an antibody comprising a light chain comprising an HVR-L1, HVR-L2 and/or HVR-L3 from the light chain variable region amino acid sequence depicted in FIG. 11J.

In one aspect, the invention provides an anti-podocalyxin antibody comprising a heavy chain variable region comprising the heavy chain variable region amino acid sequence depicted in FIG. 12A. In one aspect, the invention provides an antibody comprising a heavy chain comprising an HVR-H1, HVR-H2 and/or HVR-H3 from the heavy chain variable region amino acid sequence depicted in FIG. 12A. In one aspect, the invention provides an antibody comprising a light chain variable region comprising the light chain variable region amino acid sequence depicted in FIG. 12C. In one aspect, the invention provides an antibody comprising a light chain comprising an HVR-L1, HVR-L2 and/or HVR-L3 from the light chain variable region amino acid sequence depicted in FIG. 12C.

In some embodiments, these antibodies comprise a human subgroup III heavy chain framework consensus sequence. In one embodiments of these antibodies, these antibodies comprise a human κI light chain framework consensus sequence.

In one aspect, the invention provides an antibody comprising one, two, three, four, five or six of the HVR sequences depicted in FIG. 2. In one aspect, the invention provides an antibody comprising one, two, three, four, five or six of the HVR sequences depicted in FIG. 11. In one aspect, the invention provides an antibody comprising one, two, three, four, five or six of the HVR sequences depicted in FIG. 12.

A therapeutic agent for use in a host subject preferably elicits little to no immunogenic response against the agent in said subject. In one embodiment, the invention provides such an agent. For example, in one embodiment, the invention provides a humanized antibody that elicits and/or is expected to elicit a human anti-mouse antibody response (HAMA) at a substantially reduced level compared to an antibody comprising the sequence of SEQ ID NO: 3 and 5 in a host subject. In another example, the invention provides a humanized antibody that elicits and/or is expected to elicit minimal or no human anti-mouse antibody response (HAMA). In one example, an antibody of the invention elicits anti-mouse antibody response that is at or less than a clinically-acceptable level.

A humanized antibody of the invention may comprise one or more human and/or human consensus non-hypervariable region (e.g., framework) sequences in its heavy and/or light chain variable domain. In some embodiments, one or more additional modifications are present within the human and/or human consensus non-hypervariable region sequences. In one embodiment, the heavy chain variable domain of an antibody of the invention comprises a human consensus framework sequence, which in one embodiment is the subgroup III consensus framework sequence. In one embodiment, an antibody of the invention comprises a variant subgroup III consensus framework sequence modified at least one amino acid position.

As is known in the art, and as described in greater detail herein below, the amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions (as further defined below). The invention provides antibodies comprising modifications in these hybrid hypervariable positions. In one embodiment, these hypervariable positions include one or more positions 26-30, 33-35B, 47-49, 57-65, 93, 94 and 101-102 in a heavy chain variable domain. In one embodiment, these hybrid hypervariable positions include one or more of positions 24-29, 35-36, 46-49, 56 and 97 in a light chain variable domain. In one embodiment, an antibody of the invention comprises a human variant human subgroup consensus framework sequence modified at one or more hybrid hypervariable positions.

An antibody of the invention can comprise any suitable human or human consensus light chain framework sequences, provided the antibody exhibits the desired biological characteristics (e.g., a desired binding affinity). In one embodiment, an antibody of the invention comprises at least a portion (or all) of the framework sequence of human κ light chain. In one embodiment, an antibody of the invention comprises at least a portion (or all) of human κ subgroup I framework consensus sequence.

In other aspects of the present invention, the invention provides vectors comprising DNA encoding any of the herein described anti-podocalyxin antibodies. Host cells comprising any such vector are also provided. By way of example, the host cells may be CHO cells, *E. coli* cells, or yeast cells. A process for producing any of the herein described polypeptides is further provided and comprises culturing host cells under conditions suitable for expression of the desired polypeptide and recovering the desired polypeptide from the cell culture.

The antibody of the present invention may be employed in any known assay method, such as ELISA, competitive binding assays, direct and indirect sandwich assays, and immunoprecipitation assays (Zola, (1987) Monoclonal Antibodies: A Manual of Techniques, pp. 147-158, CRC Press, Inc.).

A detection label may be useful for localizing, visualizing, and quantitating a binding or recognition event. The labelled antibodies of the invention can detect cell-surface receptors. Another use for detectably labelled antibodies is a method of bead-based immunocapture comprising conjugating a bead with a fluorescent labelled antibody and detecting a fluorescence signal upon binding of a ligand. Similar binding detection methodologies utilize the surface plasmon resonance (SPR) effect to measure and detect antibody-antigen interactions.

Detection labels such as fluorescent dyes and chemiluminescent dyes (Briggs et al (1997) "Synthesis of Functionalised Fluorescent Dyes and Their Coupling to Amines and Amino Acids," J. Chem. Soc., Perkin-Trans. 1:1051-1058) provide a detectable signal and are generally applicable for labelling antibodies, preferably with the following properties: (i) the labelled antibody should produce a very high signal with low background so that small quantities of antibodies can be sensitively detected in both cell-free and cell-based assays; and (ii) the labelled antibody should be photostable so that the fluorescent signal may be observed, monitored and recorded without significant photo bleaching. For applications involving cell surface binding of labelled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death.

Direct quantification of cellular fluorescence intensity and enumeration of fluorescently labelled events, e.g. cell surface binding of peptide-dye conjugates may be conducted on an system (FMAT® 8100 HTS System, Applied Biosystems, Foster City, Calif.) that automates mix-and-read, non-radioactive assays with live cells or beads (Miraglia, "Homogeneous cell- and bead-based assays for high throughput screening using fluorometric microvolume assay technology", (1999) J. of Biomolecular Screening 4:193-204). Uses of labelled antibodies also include cell surface receptor binding assays, inmmunocapture assays, fluorescence linked immunosorbent assays (FLISA), caspase-cleavage (Zheng, "Caspase-3 controls both cytoplasmic and nuclear events associated with Fas-mediated apoptosis in vivo", (1998) Proc. Natl. Acad. Sci. USA 95:618-23; U.S. Pat. No. 6,372,907), apoptosis (Vermes, "A novel assay for apoptosis. Flow cytometric detection of phosphatidylserine expression on early apoptotic cells using fluorescein labelled Annexin V" (1995) J. Immunol. Methods 184:39-51) and cytotoxicity assays. Fluorometric microvolume assay technology can be used to identify the up or down regulation by a molecule that is targeted to the cell surface (Swartzman, "A homogeneous and multiplexed immunoassay for high-throughput screening using fluorometric microvolume assay technology", (1999) Anal. Biochem. 271:143-51).

Labelled antibodies of the invention are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Chen et al (2004) Bioconjugate Chem. 15:41-49; (v) bioluminescence; (vi) fluorescence; and (vii) ultrasound. Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention.

Peptide labelling methods are well known. See Haugland, 2003, Molecular Probes Handbook of Fluorescent Probes and Research Chemicals, Molecular Probes, Inc.; Brinkley, 1992, Bioconjugate Chem. 3:2; Garman, (1997) Non-Radioactive Labelling: A Practical Approach, Academic Press, London; Means (1990) Bioconjugate Chem. 1:2; Glazer et al (1975) Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tscheesche, Ed., Walter DeGryter, Berlin and New York; and Wong (1991) Chemistry of Protein Conjugation and Crosslinking, CRC Press, Boca Raton, Fla.); De Leon-Rodriguez et al (2004) Chem. Eur. J. 10:1149-1155; Lewis et al (2001) Bioconjugate Chem. 12:320-324; Li et al (2002) Bioconjugate Chem. 13:110-115; Mier et al (2005) Bioconjugate Chem. 16:240-237.

Peptides and proteins labelled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248:18-34).

The labelled antibodies of the invention may also be used as an affinity purification agent. In this process, the labelled antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer, pH 5.0, that will release the antigen from the polypeptide variant.

In one aspect, an anti-podocalyxin antibody of the invention binds to the same epitope on podocalyxin bound by another podocalyxin antibody. In another embodiment, a podocalyxin antibody of the invention binds to the same epitope on podocalyxin bound by a monoclonal antibody or fragment (e.g., a Fab fragment) of a monoclonal antibody comprising the variable domains of SEQ ID NO: 3 and SEQ ID NO: 5 (FIG. 2) or a chimeric antibody comprising the variable domain of the monoclonal antibody comprising the sequences of SEQ ID NO: 3 and SEQ ID NO: 5 (FIG. 2) and constant domains from human IgG1.

In one embodiment, a podocalyxin antibody of the invention binds to the same epitope on podocalyxin bound by a monoclonal antibody or fragment (e.g., a Fab fragment) of a monoclonal antibody comprising the variable domains of SEQ ID NO: 39 and SEQ ID NO: 41 (FIG. 12) or a chimeric antibody comprising the variable domain of the monoclonal antibody comprising the sequences of SEQ ID NO:39 and SEQ ID NO:41 (FIG. 12) and constant domains from human IgG1.

In one aspect, the invention provides compositions comprising one or more antibodies of the invention and a carrier. In one embodiment, the carrier is pharmaceutically acceptable.

In one aspect, the invention provides nucleic acids encoding a podocalyxin antibody of the invention.

In one aspect, the invention provides vectors comprising a nucleic acid of the invention. In one embodiment, the vectors comprise SEQ ID NO: 2 and/or SEQ ID NO:4 (FIG. 2). In one embodiment, the vectors comprise SEQ ID NO: 38 and/or SEQ ID NO:40 (FIG. 12).

In one embodiment, the invention provides a vector comprising a nucleic acid sequence depicted in FIG. 2. In one embodiment, the invention provides a vector comprising a nucleic acid sequence depicted in FIG. 10. In one embodiment, the invention provides a vector comprising a nucleic acid sequence depicted in FIG. 11. In one embodiment, the invention provides a vector comprising a nucleic acid sequence depicted in FIG. 12.

In one embodiment, the invention provides a vector comprising a nucleic acid sequence selected from the group SEQ ID NOs: 2, 4, 32, 34, 36, 38, and 40.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, *E. coli*. In one embodiment, a host cell is a eukaryotic cell, for example a mammalian cell such as Chinese Hamster Ovary (CHO) cell.

In one aspect, the invention provides methods for making an antibody of the invention. For example, the invention provides a method of making a podocalyxin antibody (which, as defined herein includes full length and fragments thereof), said method comprising expressing in a suitable host cell a recombinant vector of the invention encoding said antibody (or fragment thereof), and recovering said antibody.

In one aspect, the invention provides an article of manufacture comprising a container; and a composition contained within the container, wherein the composition comprises one or more podocalyxin antibodies of the invention. In one embodiment, the composition comprises a nucleic acid of the invention. In one embodiment, a composition comprising an antibody further comprises a carrier, which in some embodiments is pharmaceutically acceptable. In one embodiment, an article of manufacture of the invention further comprises instructions for administering the composition (e.g., the antibody) to a subject.

In one aspect, the invention provides a kit comprising a first container comprising a composition comprising one or more podocalyxin antibodies of the invention; and a second container comprising a buffer. In one embodiment, the buffer is pharmaceutically acceptable. In one embodiment, a composition comprising an antagonist antibody further comprises a carrier, which in some embodiments is pharmaceutically acceptable. In one embodiment, a kit further comprises instructions for administering the composition (e.g., the antibody) to a subject.

In one aspect, the invention provides use of a podocalyxin antibody of the invention in the preparation of a medicament for the therapeutic and/or prophylactic treatment of a disease, such as a cancer, a tumor and/or a cell proliferative disorder.

In one aspect, the invention provides use of a nucleic acid of the invention in the preparation of a medicament for the therapeutic and/or prophylactic treatment of a disease, such as a cancer, a tumor and/or a cell proliferative disorder.

In one aspect, the invention provides use of an expression vector of the invention in the preparation of a medicament for the therapeutic and/or prophylactic treatment of a disease, such as a cancer, a tumor and/or a cell proliferative disorder.

In one aspect, the invention provides use of a host cell of the invention in the preparation of a medicament for the therapeutic and/or prophylactic treatment of a disease, such as a cancer, a tumor and/or a cell proliferative disorder.

In one aspect, the invention provides use of an article of manufacture of the invention in the preparation of a medicament for the therapeutic and/or prophylactic treatment of a disease, such as a cancer, a tumor and/or a cell proliferative disorder.

In one aspect, the invention provides use of a kit of the invention in the preparation of a medicament for the therapeutic and/or prophylactic treatment of a disease, such as a cancer, a tumor and/or a cell proliferative disorder.

In one aspect, the invention provides a method of inhibiting the growth of a cell that expresses podocalyxin, said method comprising contacting said cell with an antibody of the invention thereby causing an inhibition of growth of said cell. In one embodiment, the cell is contacted with an anti-podocalyxin antibody in vitro. In one embodiment, the cell is contacted with an anti-podocalyxin antibody in vivo.

In one aspect, the invention provides a method of inhibiting proliferation of a cell that expresses podocalyxin, said method comprising contacting said cell with an antibody of the invention thereby causing an inhibition of proliferation of said cell. In one embodiment, the cell is contacted with an anti-podocalyxin antibody in vitro. In one embodiment, the cell is contacted with an anti-podocalyxin antibody in vivo.

In one aspect, the invention provides a method of therapeutically treating a mammal having a cancerous tumor comprising a cell that expresses podocalyxin, said method comprising administering to said mammal a therapeutically effective amount of an antibody of the invention, thereby effectively treating said mammal.

In one aspect, the invention provides use of a podocalyxin antibody of the invention in the preparation of a medicament for (i) inhibiting the vascularization of a tumor comprising cells expressing podocalyxin; (ii) inhibiting the delamination of cells expressing podocalyxin; (iii) inhibiting tumor metastasis in a patient having cancer; (iv) decreasing tumor size in a patient having cancer.

In one aspect, the invention provides a method for treating or preventing a cell proliferative disorder associated with increased expression of podocalyxin, said method comprising administering to a subject in need of such treatment an effective amount of an antibody of the invention, thereby effectively treating or preventing said cell proliferative disorder. In one embodiment, said cell proliferative disorder is cancer.

In one aspect, the invention provides a method of determining the presence of podocalyxin in a sample suspected of containing podocalyxin, said method comprising exposing said sample to an antibody of the invention, and determining binding of said antibody to podocalyxin in said sample wherein binding of said antibody to podocalyxin in said sample is indicative of the presence of said protein in said sample. In one embodiment, the sample is a biological sample. In a further embodiment, the biological sample comprises cancer cells. In one embodiment, the biological sample is from a mammal experiencing or suspected of experiencing a cancer disorder and/or a cancer cell proliferative disorder.

In one aspect, a method of diagnosing a cell proliferative disorder associated with (i) an increase in cells, such as cancer cells, expressing podocalyxin, or (ii) an increase in podocalyxin expression within a tumor, is provided. In one embodiment, the method comprises contacting test cells in a biological sample with an anti-podocalyxin antibody; determining the level of antibody bound to test cells in the sample by detecting binding of the antibody to podocalyxin, and comparing the level of antibody bound to cells in a control sample, wherein a higher level of antibody bound in the test sample as compared to the control sample indicates the presence of a cancer associated with cells expressing podocalyxin. In one embodiment, the method involves normalization to the number of cells in the test and control samples. As will be understood by the reasonably skilled artisan, appropriate annotated control samples may be used. In one embodiment, a control sample is a non-tumour biological sample.

In another aspect, the present invention provides a method of determining cancer patient prognosis. In one embodiment, the method includes the step of detecting a differential level of expression of podocalyxin in the patient sample, as compared to a control, wherein the differential expression is indicative of the patient's prognosis. In one embodiment, the method includes the step of detecting a higher level of expression of podocalyxin in the patent sample, as compared to a control, wherein the higher expression indicates that the patient has a poor prognosis. In one embodiment, the method includes the step of detecting a lower level of expression of podocalyxin in the patient sample, as compared to a control, wherein the lower expression indicates that the patient has a good prognosis. As will be understood by the reasonably skilled artisan, appropriate annotated control samples may be used.

In another aspect, the present invention provides a method of determining cancer patient risk of tumor metastasis. In one embodiment, the method includes the step of detecting a differential level of expression of podocalyxin in the patient sample, as compared to a control, wherein the differential expression is indicative of the patient's risk of tumor metastasis. In one embodiment, the method includes the step of detecting a higher level of expression of podocalyxin in the patent sample, as compared to a control, wherein the higher expression indicates that the patient has a higher risk of tumor metastasis. In one embodiment, the method includes the step of detecting a lower level of expression of podocalyxin in the patient sample, as compared to a control, wherein the lower expression indicates that the patient has a lower risk of tumor metastasis. As will be understood by the reasonably skilled artisan, appropriate annotated control samples may be used.

In another aspect, the present invention provides a prognostic method for monitoring the outcome of treatment after a subject is administered a therapeutic agent for the treatment of cancer. In one embodiment, the method includes the step of detecting a differential level of podocalyxin expression in a test sample, as compared to a control, obtained from the subject who has been treated for cancer, wherein the differential level of expression is indicative of the outcome of treatment of the subject. In one other embodiment, the method includes the step of detecting a lower level of podocalyxin expression in a test sample, as compared to a control, obtained from the subject who has been treated for cancer, wherein the lower level of expression is indicative of a positive outcome of treatment of the subject. In one other embodiment, the method includes the step of detecting a higher level of podocalyxin expression in a test sample, as compared to a control, obtained from the subject who has been treated for cancer, wherein the higher level of expression is indicative of a negative outcome of treatment of the subject. As will be understood by the reasonably skilled artisan, appropriate annotated control samples may be used.

In another aspect the invention provides a method of assessing whether a sample from a patient with cancer indicates responsiveness of the patient to treatment with an anti-cancer agent. In one embodiment, the method includes the step of detecting a differential level of expression of podocalyxin in the sample, as compared to a control, wherein the differential expression is indicative of the responsiveness of the patient to the treatment. In one embodiment, the method includes the step of detecting a lower level of expression of podocalyxin in the sample, as compared to a control, wherein the lower expression indicates that the patient is responsive to the treatment. In one embodiment, the method includes the step of detecting a higher level of expression of podocalyxin in the sample, as compared to a control, wherein the higher expression indicates that the patient is not responsive to the treatment. In another embodiment, the differential level of expression is indicative of metastatic propensity. In one embodiment, a higher expression indicates a higher propensity. In another embodiment, a lower expression indicates a lower propensity. As will be understood by the reasonably skilled artisan, appropriate annotated control samples may be used.

In one aspect, the invention provides a method of inhibiting the vascularization of a tumor comprising a cell expressing podocalyxin, comprising administering to a patient an effective amount of an antibody described herein, thereby effectively inhibiting vascularization of the tumor.

In one aspect, the invention provides a method of inhibiting the delamination of cells expressing podocalyxin, comprising administering to a patient an effective amount of an antibody described herein, thereby effectively inhibiting delamination of the cells. Inhibition of delamination of cells is desired, for example, in the treatment of cancer and the prevention of tumour cell migration.

In one aspect, the invention provides a method of inhibiting tumor metastasis in a patient having cancer, comprising administering to a patient an effective amount of an antibody described herein, thereby effectively inhibiting tumor metastasis.

In one aspect, the invention provides a method of decreasing tumor size, comprising administering to a patient an effective amount of an antibody described herein, thereby effectively decreasing tumor size.

In one aspect, the invention provides a method for treating or preventing a cell proliferative disorder associated with increased expression of podocalyxin, said method comprising administering to a subject in need of such treatment an effective amount of an antibody of the invention, thereby effectively treating or preventing said cell proliferative disorder. In one embodiment, said proliferative disorder is cancer. The increased expression of podocalyxin may be detected in a sample from the patient.

In one aspect, the invention provides a method of binding an antibody of the invention to a cell that expresses podocalyxin, said method comprising contacting said cell with an antibody of the invention.

In other aspects of the present invention, the invention provides vectors comprising DNA encoding any of the herein described antibodies. Host cell comprising any such vector are also provided. By way of example, the host cells may be CHO cells, E. coli cells, or yeast cells. A process for producing any of the herein described antibodies is further provided and comprises culturing host cells under conditions suitable for expression of the desired antibody and recovering the desired antibody from the cell culture.

In a still further aspect, the invention concerns a composition of matter comprising an anti-podocalyxin antibody as described herein, in combination with a carrier. Optionally, the carrier is a pharmaceutically acceptable carrier.

Another aspect of the present invention is directed to the use of an anti-podocalyxin polypeptide antibody as described herein, for the preparation of a medicament useful in the treatment of a condition which is responsive to the anti-podocalyxin polypeptide antibody.

In another aspect, the invention provides immunoconjugates, or antibody-drug conjugates (ADC), comprising an anti-podocalyxin antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In another aspect, the invention further provides methods of using the immunoconjugates. In one aspect, an immunoconjugate comprises any of the above anti-podocalyxin antibodies covalently attached to a cytotoxic agent or a detectable agent.

ADC technology is well known in the art. The use ADC for the local delivery of cytotoxic or cytostatic agents, i.e. drugs to kill or inhibit tumor cells in the treatment of cancer (Lambert, J. (2005) Curr. Opinion in Pharmacology 5:543-549; Wu et al (2005) Nature Biotechnology 23(9):1137-1146; Payne, G. (2003) Cancer Cell 3:207-212; Syrigos and Epenetos (1999) Anticancer Research 19:605-614; Niculescu-Duvaz and Springer (1997) Adv. Drug Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al (ed.$), pp. 475-506). Drug moieties used in antibody drug conjugates include bacterial protein toxins such as diphtheria toxin, plant protein toxins such as ricin, small molecules such as auristatins, geldanamycin (Mandler et al (2000) J. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al (1996) Proc. Natl. Acad. Sci. USA 93:8618-8623), calicheamicin (Lode et al (1998) Cancer Res. 58:2928; Hinman et al (1993) Cancer Res. 53:3336-3342), daunomycin, doxorubicin, methotrexate, and vindesine (Rowland et al (1986) supra). The drug moieties may affect cytotoxic and cytostatic mechanisms including tubulin binding, DNA binding, or topoisomerase inhibition. Some cytotoxic drugs tend to be inactive or less active when conjugated to large antibodies or protein receptor ligands.

Any conventional means of attaching, i.e. linking through covalent bonds, a drug moiety to an antibody may be used. For example, the reactive groups of cysteines or lysines within podocalyxin antibodies may be used. Also, cysteine-engineered antibodies have been designed as FAB antibody fragments (thioFab) and expressed as full-length, IgG monoclonal (thioMab) antibodies (Junutula, J. R. et al. (2008) J Immunol Methods 332:41-52; US 2007/0092940, now U.S. Pat. No. 7,521,541, granted on Apr. 21, 2009). ThioFab and ThioMab antibodies have been conjugated through linkers at the newly introduced cysteine thiols with thiol-reactive linker reagents and drug-linker reagents to prepare antibody drug conjugates. Site specific conjugation methods are well known in the art. See for example Behrens and Liu, MAbs, Sep. 27, 2013, 6(1), "Methods of site specific drug conjugation to antibodies."

Antibody may be conjugated to drug in ADC either directly or via a linker, and the average number of drug moieties per antibody can range, e.g., from about 1 to about 20 drug moieties per antibody, and in certain embodiments, from 1 to about 8 drug moieties per antibody.

Any convention linker may be used. A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), and those resulting from conjugation with linker reagents: N-Succinimidyl 4-(2-pyridylthio) pentanoate ("SPP"), N-succinimidyl 4-(N-maleimidomethyl) cyclohexane-1 carboxylate ("SMCC", also referred to herein as "MCC"), and N-Succinimidyl (4-iodo-acetyl) aminobenzoate ("SIAB"). Various linker components are known in the art, some of which are described below.

A linker may be a "cleavable linker," facilitating release of a drug in the cell. For example, an acid-labile linker (e.g., hydrazone), protease-sensitive (e.g., peptidase-sensitive) linker, photolabile linker, dimethyl linker or disulfide-containing linker (Chari et al., Cancer Research 52:127-131 (1992); U.S. Pat. No. 5,208,020) may be used. Exemplary linkers are described in U.S. Pat. No. 7,498,298.

In some embodiments, a linker component may comprise a "stretcher unit" that links an antibody to another linker component or to a drug moiety.

In some embodiments, a linker component may comprise an amino acid unit. In one such embodiment, the amino acid unit allows for cleavage of the linker by a protease, thereby facilitating release of the drug from the immunoconjugate upon exposure to intracellular proteases, such as lysosomal enzymes. See, e.g., Doronina et al. (2003) Nat. Biotechnol. 21:778-784. Exemplary amino acid units include, but are not limited to, a dipeptide, a tripeptide, a tetrapeptide, and a pentapeptide. Exemplary dipeptides include: valine-citrulline (vc or val-cit), alanine-phenylalanine (af or ala-phe); phenylalanine-lysine (fk or phe-lys); or N-methyl-valine-citrulline (Me-val-cit). Exemplary tripeptides include: glycine-valine-citrulline (gly-val-cit) and glycine-glycine-glycine (gly-gly-gly). An amino acid unit may comprise amino acid residues that occur naturally, as well as minor amino acids and non-naturally occurring amino acid analogs, such as citrulline. Amino acid units can be designed and optimized in their selectivity for enzymatic cleavage by a particular enzyme, for example, a tumor-associated protease, cathepsin B, C and D, or a plasmin protease.

In some embodiments, a linker component may comprise a "spacer" unit that links the antibody to a drug moiety, either directly or by way of a stretcher unit and/or an amino acid unit. A spacer unit may be "self-immolative" or a "non-self-immolative." A "non-self-immolative" spacer unit is one in which part or all of the spacer unit remains bound to the drug moiety upon enzymatic (e.g., proteolytic) cleavage of the ADC. Examples of non-self-immolative spacer units include, but are not limited to, a glycine spacer unit and a glycine-glycine spacer unit. Other combinations of peptidic spacers susceptible to sequence-specific enzymatic cleavage are also contemplated. For example, enzymatic cleavage of an ADC containing a glycine-glycine spacer unit by a tumor-cell associated protease would result in release of a glycine-glycine-drug moiety from the remainder of the ADC. In one such embodiment, the glycine-glycine-drug moiety is then subjected to a separate hydrolysis step in the tumor cell, thus cleaving the glycine-glycine spacer unit from the drug moiety.

A "self-immolative" spacer unit allows for release of the drug moiety without a separate hydrolysis step. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. See, e.g., Hamann et al. (2005) Expert Opin. Ther. Patents (2005) 15:1087-1103. In one embodiment, the spacer unit is p-aminobenzyloxycarbonyl (PAB). In certain embodiments, the phenylene portion of a p-amino benzyl unit is substituted with Qm, wherein Q is —$C_1$-$C_8$ alkyl, —O—($C_1$-$C_8$ alkyl), -halogen, -nitro or -cyano; and m is an integer ranging from 0-4. Examples of self-immolative spacer units further include, but are not limited to, aromatic compounds that are electronically similar to p-aminobenzyl alcohol (see, e.g., US 2005/0256030 A1, now U.S. Pat. No. 7,375,078, granted May 20, 2008), such as 2-aminoimidazol-5-methanol derivatives (Hay et al. (1999) Bioorg. Med. Chem. Lett. 9:2237) and ortho- or para-aminobenzylacetals. Spacers can be used that undergo cyclization upon amide bond hydrolysis, such as substituted and unsubstituted 4-aminobutyric acid amides (Rodrigues et al., Chemistry Biology, 1995, 2, 223); appropriately substituted bicyclo[2.2.1] and bicyclo [2.2.2] ring systems (Storm, et al., J. Amer. Chem. Soc., 1972, 94, 5815); and 2-aminophenylpropionic acid amides (Amsberry, et al., J. Org. Chem., 1990, 55, 5867). Elimination of amine-containing drugs that are substituted at the α-position of glycine (Kingsbury, et al., J. Med. Chem., 1984, 27, 1447) are also examples of self-immolative spacers useful in ADCs.

In one embodiment, a spacer unit is a branched unit of the prior art, which can be used to incorporate and release multiple drugs.

In another embodiment, linker L may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker.

A. Anti-Podocalyxin Antibodies

In one embodiment, the present invention provides anti-podocalyxin antibodies which may find use herein as therapeutic agents. Exemplary antibodies include polyclonal, monoclonal, chimeric, humanized, and human antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, SOCl2, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

A monoclonal antibody (mAb) to an antigen-of-interest can be prepared by using any technique known in the art. These include, but are not limited to, the hybridoma technique originally described by Kohler and Milstein (1975, Nature 256, 495-497), the human B cell hybridoma technique (Kozbor et al., 1983, Immunology Today 4:72), and the EBV-hybridoma technique (Cole et al., 1985, Monoclonal Antibodies and Cancer Therapy, Alan R. Liss, Inc., pp. 77-96). The Selected Lymphocyte Antibody Method (SLAM) (Babcook, J. S., et al., A novel strategy for generating monoclonal antibodies from single, isolated lymphocytes producing antibodies of defined specificities. Proc Natl Acad Sci USA, 1996. 93 (15): p. 7843-8.) and (McLean G R, Olsen O A, Watt I N, Rathanaswami P, Leslie K B, Babcook J S, Schrader J W. Recognition of human cytomegalovirus by human primary immunoglobulins identifies an innate foundation to an adaptive immune response. J Immunol. 2005 Apr. 15; 174(8):4768-78. Such antibodies may be of any immunoglobulin class including IgG, IgM, IgE, IgA, and IgD and any subclass thereof. The hybridoma producing the mAbs of use in this invention may be cultivated in vitro or in vivo.

Monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal, e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pliickthun, Immunol. Revs. 130:151-188 (1992).

In a further embodiment, monoclonal antibodies or antibody fragments can be isolated from antibody phage libraries generated using the techniques described in McCafferty et al., Nature, 348:552-554 (1990). Clackson et al., Nature, 352:624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res. 22:1265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CO sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Chimeric, Humanized, and Human Antibodies

In some embodiments, the anti-podocalyxin antibody is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

The anti-podocalyxin antibodies of the invention may further comprise humanized antibodies or human antibodies. Humanized forms of non-human (e.g., murine or rabbit) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. Reduction or elimination of a HAMA response is a significant aspect of clinical development of suitable therapeutic agents. See, e.g., Khaxzaeli et al., J. Natl. Cancer Inst. (1988), 80:937; Jaffers et al., Transplantation (1986), 41:572; Shawler et al., J. Immunol. (1985), 135:1530; Sears et al., J. Biol. Response Mod. (1984), 3:138; Miller et al., Blood (1983), 62:988; Hakimi et al., J. Immunol. (1991), 147:1352; Reichmann et al., Nature (1988), 332:323; Junghans et al., Cancer Res. (1990), 50:1495. As described herein, the invention provides antibodies that are humanized such that HAMA response is reduced or eliminated. Variants of these antibodies can further be obtained using routine methods known in the art, some of which are further described below. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol. 151:2623 (1993)).

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), preferably the acceptor human frameworks are from, or derived from, a human consensus framework sequence as such frameworks have been demonstrated to have minimal, or no, immunogenicity in human patients.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor.

In one embodiment, human consensus frameworks herein are from, or derived from, VH subgroup III and/or VL kappa subgroup I consensus framework sequences.

While the acceptor may be identical in sequence to the human framework sequence selected, whether that be from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

Hypervariable region residues of the non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-34 (L1), 50-56 (L2) and 89-97 (L3), 26-35B (H1), 50-65, 47-65 or 49-65 (H2) and 93-102, 94-102, or 95-102 (H3).

While "incorporation" of hypervariable region residues is discussed herein, it will be appreciated that this can be achieved in various ways, for example, nucleic acid encoding the desired amino acid sequence can be generated by mutating nucleic acid encoding the mouse variable domain sequence so that the framework residues thereof are changed to acceptor human framework residues, or by mutating nucleic acid encoding the human variable domain sequence so that the hypervariable domain residues are changed to non-human residues, or by synthesizing nucleic acid encoding the desired sequence, etc.

As described herein, hypervariable region-grafted variants may be generated by Kunkel mutagenesis of nucleic acid encoding the human acceptor sequences, using a separate oligonucleotide for each hypervariable region. Kunkel et al., Methods Enzymol. 154:367-382 (1987). Appropriate changes can be introduced within the framework and/or hypervariable region, using routine techniques, to correct and re-establish proper hypervariable region-antigen interactions.

Phage(mid) display (also referred to herein as phage display in some contexts) can be used as a convenient and fast method for generating and screening many different potential variant antibodies in a library generated by sequence randomization. However, other methods for making and screening altered antibodies are available to the skilled person.

Phage(mid) display technology has provided a powerful tool for generating and selecting novel proteins which bind to a ligand, such as an antigen. Using the techniques of phage(mid) display allows the generation of large libraries of protein variants which can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phagemid display systems where the nucleic acid sequence encoding the protein or polypeptide is fused to a nucleic acid sequence encoding a portion of the gene III protein have been developed. (Bass, S., Proteins, 8:309 (1990); Lowman and Wells, Methods: A Companion to Methods in Enzymology, 3:205 (1991)). In a monovalent phagemid display system, the gene fusion is expressed at low levels and wild type gene III proteins are also expressed so that infectivity of the particles is retained. Methods of generating peptide libraries and screening those libraries have been disclosed in many patents (e.g. U.S. Pat. Nos. 5,723,286, 5,432,018, 5,580,717, 5,427,908 and 5,498,530).

Libraries of antibodies or antigen binding polypeptides have been prepared in a number of ways including by altering a single gene by inserting random DNA sequences or by cloning a family of related genes. Methods for displaying antibodies or antigen binding fragments using phage(mid) display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with the desired characteristics.

Methods of substituting an amino acid of choice into a template nucleic acid are well established in the art, some of which are described herein. For example, hypervariable region residues can be substituted using the Kunkel method. See, e.g., Kunkel et al., Methods Enzymol. 154:367-382 (1987).

The sequence of oligonucleotides includes one or more of the designed codon sets for the hypervariable region residues to be altered. A codon set is a set of different nucleotide triplet sequences used to encode desired variant amino acids. Codon sets can be represented using symbols to designate particular nucleotides or equimolar mixtures of nucleotides as shown in below according to the IUB code.

IUB Codes
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T) H
N (A or C or G or T)

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al. Nucleic Acids Res. 10:6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., Proc. Nat'l. Acad. Sci. USA, 75:5765 (1978).

The DNA template is generated by those vectors that are either derived from bacteriophage M13 vectors (the commercially available M13 mp 18 and M13 mp 19 vectors are suitable), or those vectors that contain a single-stranded phage origin of replication as described by Viera et al., Meth. Enzymol., 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as E. coli JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. Meth. Enzymol., 153:3 (1987). Thus, the DNA that is to be mutated must be inserted into one of these vectors in order to generate single-stranded template. Production of the single-stranded template is described in sections 4.21-4.41 of Sambrook et al., supra.

According to another method, antigen binding may be restored during humanization of antibodies through the selection of repaired hypervariable regions (See application Ser. No. 11/061,841, filed Feb. 18, 2005). The method includes incorporating non-human hypervariable regions onto an acceptor framework and further introducing one or more amino acid substitutions in one or more hypervariable regions without modifying the acceptor framework sequence. Alternatively, the introduction of one or more amino acid substitutions may be accompanied by modifications in the acceptor framework sequence.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

The sequence of the PCR primers includes one or more of the designed codon sets for the solvent accessible and highly diverse positions in a hypervariable region. As described above, a codon set is a set of different nucleotide triplet sequences used to encode desired variant amino acids.

Antibody selectants that meet the desired criteria, as selected through appropriate screening/selection steps can be isolated and cloned using standard recombinant techniques.

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-podocalyxin antibody are contemplated. For example, the humanized antibody may be an antibody fragment, such as a Fab. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno. 7:33 (1993); U.S. Pat. Nos. 5,545,806, 5,569,825, 5,591,669 (all of GenPharm); 5,545,807; and WO 97/17852.

Alternatively, phage display technology (McCafferty et al., Nature 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

In another embodiment, the antibodies of this disclosure are human monoclonal antibodies. Such human monoclonal antibodies directed against podocalyxin can be generated using transgenic or transchromosomic mice carrying parts of the human immune system rather than the mouse system. These transgenic and transchromosomic mice include mice referred to herein as the HuMAb Mouse™ and KM Mouse™, respectively, and are collectively referred to herein as "human Ig mice."

The HuMAb Mouse™ (Medarex, Inc.) contains human immunoglobulin gene miniloci that encode unrearranged human heavy ($\mu$ and $\gamma$) and $\kappa$ light chain immunoglobulin sequences, together with targeted mutations that inactivate the endogenous $\mu$ and $\kappa$ chain loci (see e.g., Lonberg, et al. (1994) Nature 368(6474): 856-859). Accordingly, the mice exhibit reduced expression of mouse IgM or $\kappa$, and in response to immunization, the introduced human heavy and light chain transgenes undergo class switching and somatic mutation to generate high affinity human IgG$\kappa$ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). Preparation and use of the HuMAb Mouse™, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al., (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of this disclosure can be raised using a mouse that carries human immunoglobulin sequences on transgenes and transchomosomes, such as a mouse that carries a human heavy chain transgene and a human light chain transchromosome. This mouse is referred to herein as a "KM Mouse™" and is described in detail in PCT Publication WO 02/43478 to Ishida et al.

Still further, alternative transgenic animal systems expressing human immunoglobulin genes are available in the art and can be used to raise anti-podocalyxin antibodies of this disclosure. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-podocalyxin antibodies of this disclosure. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise anti-podocalyxin antibodies of this disclosure.

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example.

5. Bispecific Antibodies

Bispecific antibodies are antibodies that have binding specificities for at least two different epitopes. Exemplary bispecific antibodies may bind to two different epitopes of a podocalyxin protein as described herein. Other such antibodies may combine a podocalyxin binding site with a binding site for another protein. Alternatively, an anti-podocalyxin arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the podocalyxin-expressing cell. Bispecific antibodies may also be used to localize cytotoxic agents to cells which express podocalyxin. These antibodies possess a podocalyxin-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')2 bispecific antibodies).

WO 96/16673 describes a bispecific anti-ErbB2/anti-FcγRIII antibody and U.S. Pat. No. 5,837,234 discloses a bispecific anti-ErbB2/anti-FcγRT antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J. 10:3655-3659 (1991).

6. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

B. Certain Methods of Making Antibodies

1. Screening for Anti-Podocalyxin Antibodies with the Desired Properties

Techniques for generating antibodies that bind to podocalyxin polypeptides have been described above. One may further select antibodies with certain biological characteristics, as desired.

The growth inhibitory effects of an anti-podocalyxin antibody of the invention may be assessed by methods known in the art, e.g., using cells which express a podocalyxin polypeptide either endogenously or following transfection with the podocalyxin gene. For example, appropriate tumor cell lines and podocalyxin-transfected cells may be treated with an anti-podocalyxin monoclonal antibody of the invention at various concentrations for a few days (e.g., 2-7) days and stained with crystal violet or MTT or analyzed by some other colorimetric assay. Another method of measuring proliferation would be by comparing 3H-thymidine uptake by the cells treated in the presence or absence an anti-podocalyxin antibody of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. The tumor cell may be one that overexpresses a podocalyxin polypeptide. The anti-podocalyxin antibody will inhibit cell proliferation of a podocalyxin-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 μg/ml. Growth inhibition can be measured at an antibody concentration of about 0.5 to 30 μg/ml or about 0.5 nM to 200 nM in cell culture, where the growth inhibition is determined 1-10 days after exposure of the tumor cells to the antibody. The antibody is growth inhibitory in vivo if administration of the anti-podocalyxin antibody at about 1 μg/kg to about 100 mg/kg body weight results in reduction in tumor size or reduction of tumor cell proliferation within about 5 days to 3 months from the first administration of the antibody, preferably within about 5 to 30 days.

To select for an anti-podocalyxin antibody which induces cell death, loss of membrane integrity as indicated by, e.g., propidium iodide (PI), trypan blue or 7AAD uptake may be assessed relative to control. A PI uptake assay can be performed in the absence of complement and immune effector cells. Podocalyxin polypeptide-expressing tumor cells are incubated with medium alone or medium containing the appropriate anti-podocalyxin antibody (e.g, at about 10 μg/ml). The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 μg/ml). Samples may be analyzed using a FACSCAN® flow cytometer and FACSCONVERT® CellQuest software (Becton Dickinson). Those anti-podocalyxin antibodies that induce statistically significant levels of cell death as determined by PI uptake may be selected as cell death-inducing anti-podocalyxin antibodies.

To screen for antibodies which bind to an epitope on a podocalyxin polypeptide bound by an antibody of interest, a routine cross-blocking assay such as that described in Antibodies, A Laboratory Manual, Cold Spring Harbor Laboratory, Ed Harlow and David Lane (1988), can be performed. This assay can be used to determine if a test antibody binds the same site or epitope as a known anti-Podocalyxin antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a podocalyxin polypeptide can be used in competition assays with the test antibodies or with a test antibody and an antibody with a characterized or known epitope.

In addition, candidate antibodies may also be screened for function using one or more of the following: in vivo screening for inhibition of metastasis, inhibition of chemotaxis by an in vitro method (e.g., Huntsman et al. U.S. 2010/0061978, incorporated herein by reference in its entirety), inhibition of vascularization, inhibition of tumour growth, and decrease in tumor size.

2. Certain Library Screening Methods

Anti-podocalyxin antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. (2001) in Methods in Molecular Biology 178:1-37 (O'Brien et al., ed., Human Press, Totowa, N.J.), and in certain embodiments, in Lee et al. (2004) J. Mol. Biol. 340:1073-1093.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-podocalyxin antibodies of the invention can be obtained by designing a suitable antigen screening procedure to select for the phage clone of interest followed by construction of a full length anti-podocalyxin antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., J. Mol. Biol., 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., Nucl. Acids Res., 19: 4133-4137 (1991).

In general, nucleic acids encoding antibody gene fragments are obtained from immune cells harvested from humans or animals. If a library biased in favor of anti-podocalyxin clones is desired, the subject is immunized with podocalyxin to generate an antibody response, and spleen cells and/or circulating B cells other peripheral blood lymphocytes (PBLs) are recovered for library construction. In a preferred embodiment, a human antibody gene fragment library biased in favor of anti-podocalyxin clones is obtained by generating an anti-podocalyxin antibody response in transgenic mice carrying a functional human immunoglobulin gene array (and lacking a functional endogenous antibody production system) such that podocalyxin immunization gives rise to B cells producing human antibodies against Podocalyxin. The generation of human antibody-producing transgenic mice is described below.

Additional enrichment for anti-podocalyxin reactive cell populations can be obtained by using a suitable screening procedure to isolate B cells expressing podocalyxin-specific membrane bound antibody, e.g., by cell separation using podocalyxin affinity chromatography or adsorption of cells to fluorochrome-labeled podocalyxin followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which podocalyxin is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression.

The V genes can be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). However, for amplifying from cDNA, back primers can also be based in the leader exon as described in Jones et al., Biotechnol., 9: 88-89 (1991), and forward primers within the constant region as described in Sastry et al., Proc. Natl. Acad. Sci. (USA), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., J. Mol. Biol., 222: 581-597 (1991) or as described in the method of Orum et al., Nucleic Acids Res., 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes can be derived in vitro from V gene segments. Most of the human VH-gene segments have been cloned and sequenced (reported in Tomlinson et al., J. Mol. Biol., 227: 776-798 (1992)), and mapped (reported in Matsuda et al., Nature Genet., 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, J. Mol. Biol., 227: 381-388 (1992). VH repertoires can also be made with all the sequence diversity focused in a long H3 loop of a single length as described in Barbas et al., Proc. Natl. Acad. Sci. USA, 89: 4457-4461 (1992). Human Vκ and Vλ segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., Gene, 128: 119-126 (1993), or in vivo by combinatorial infection, e.g., the loxP system described in Waterhouse et al., Nucl. Acids Res., 21: 2265-2266 (1993). The in vivo recombination approach exploits the two-chain nature of Fab fragments to overcome the limit on library size imposed by E. coli transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity (Kd-1 of about 10-8 M).

Alternatively, the repertoires may be cloned sequentially into the same vector, e.g. as described in Barbas et al., Proc. Natl. Acad. Sci. USA, 88: 7978-7982 (1991), or assembled together by PCR and then cloned, e.g. as described in Clackson et al., Nature, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., Nucl. Acids Res., 20: 3831-3837 (1992).

The antibodies produced by naive libraries (either natural or synthetic) can be of moderate affinity ($Kd^{-1}$ of about $10^6$ to $10^7$ $M^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities of about $10^{-9}$M or less.

Screening of the libraries can be accomplished by various techniques known in the art. For example, Podocalyxin can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized podocalyxin under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., Proc. Natl. Acad. Sci USA, 88: 7978-7982 (1991), or by alkali, e.g. as described in Marks et al., J. Mol. Biol., 222:

581-597 (1991), or by Podocalyxin antigen competition, e.g. in a procedure similar to the antigen competition method of Clackson et al., Nature, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

It is possible to select between phage antibodies of different affinities, even with affinities that differ slightly, for Podocalyxin. However, random mutation of a selected antibody (e.g. as performed in some affinity maturation techniques) is likely to give rise to many mutants, most binding to antigen, and a few with higher affinity. With limiting podocalyxin, rare high affinity phage could be competed out. To retain all higher affinity mutants, phages can be incubated with excess biotinylated podocalyxin, but with the biotinylated podocalyxin at a concentration of lower molarity than the target molar affinity constant for podocalyxin. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-podocalyxin clones may be selected based on activity. In certain embodiments, the invention provides anti-podocalyxin antibodies that bind to living cells that naturally express podocalyxin. In one embodiment, the invention provides anti-podocalyxin antibodies that block the binding between a podocalyxin ligand and podocalyxin, but do not block the binding between a podocalyxin ligand and a second protein. Fv clones corresponding to such anti-podocalyxin antibodies can be selected by (1) isolating anti-podocalyxin clones from a phage library as described above, and optionally amplifying the isolated population of phage clones by growing up the population in a suitable bacterial host; (2) selecting podocalyxin and a second protein against which blocking and non-blocking activity, respectively, is desired; (3) adsorbing the anti-podocalyxin phage clones to immobilized podocalyxin; (4) using an excess of the second protein to elute any undesired clones that recognize podocalyxin-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., Curr. Opinion in Immunol., 5: 256 (1993) and Pluckthun, Immunol. Revs, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-podocalyxin antibody derived from a hybridoma can also be modified, for example, by substituting the coding sequence for human heavy- and light-chain constant domains in place of homologous murine sequences derived from the hybridoma clone (e.g. as in the method of Morrison et al., Proc. Natl. Acad. Sci. USA, 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

D. Anti-Podocalyxin Antibody Variants and Modifications

1. Variants

In addition to the anti-podocalyxin antibodies described herein, it is contemplated that anti-podocalyxin antibody variants can be prepared. Anti-podocalyxin antibody variants can be prepared by introducing appropriate nucleotide changes into the encoding DNA, and/or by synthesis of the desired antibody or polypeptide. Those skilled in the art will appreciate that amino acid changes may alter post-translational processes of the anti-podocalyxin antibody, such as changing the number or position of glycosylation sites or altering the membrane anchoring characteristics.

Variations in the anti-podocalyxin antibodies described herein, can be made, for example, using any of the techniques and guidelines for conservative and non-conservative mutations set forth, for instance, in U.S. Pat. No. 5,364,934. Variations may be a substitution, deletion or insertion of one or more codons encoding the antibody or polypeptide that results in a change in the amino acid sequence as compared with the native sequence antibody or polypeptide. Optionally the variation is by substitution of at least one amino acid with any other amino acid in one or more of the domains of the anti-podocalyxin antibody. Guidance in determining which amino acid residue may be inserted, substituted or deleted without adversely affecting the desired activity may be found by comparing the sequence of the anti-podocalyxin antibody with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Anti-podocalyxin antibody fragments are provided herein. Such fragments may be truncated at the N-terminus or C-terminus, or may lack internal residues, for example, when compared with a full length native antibody or protein. Certain fragments lack amino acid residues that are not essential for a desired biological activity of the anti-podocalyxin antibody.

Anti-podocalyxin antibody fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-podocalyxin antibody fragments share at least one biological and/or immunological activity with the native anti-podocalyxin antibody disclosed herein.

In particular embodiments, conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |

TABLE 1-continued

| Original Residue | Exemplary Substitutions | Preferred Substitutions |
| --- | --- | --- |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the anti-podocalyxin antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the anti-podocalyxin antibody variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244:1081-1085 (1989)]. Alanine is also typically preferred because it is the most common amino acid. Further, it is frequently found in both buried and exposed positions [Creighton, The Proteins, (W.H. Freeman & Co., N.Y.); Chothia, J. Mol. Biol., 150:1 (1976)]. If alanine substitution does not yield adequate amounts of variant, an isoteric amino acid can be used.

Any cysteine residue not involved in maintaining the proper conformation of the anti-podocalyxin antibody also may be substituted, generally with serine, to improve the oxidative stability of the molecule and prevent aberrant crosslinking. Conversely, cysteine bond(s) may be added to the anti-podocalyxin antibody to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and Podocalyxin polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the anti-podocalyxin antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-podocalyxin antibody.

2. Modifications

Covalent modifications of anti-podocalyxin antibodies are included within the scope of this invention. One type of covalent modification includes reacting targeted amino acid residues of an anti-podocalyxin antibody with an organic derivatizing agent that is capable of reacting with selected side chains or the N- or C-terminal residues of the anti-podocalyxin antibody. Derivatization with bifunctional agents is useful, for instance, for crosslinking anti-podocalyxin antibody to a water-insoluble support matrix or surface for use in the method for purifying anti-podocalyxin antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: Structure and Molecular Properties, W.H. Freeman & Co., San Francisco, pp. 79-86 (1983)], acetylation of the N-terminal amine, and amidation of any C-terminal carboxyl group.

Another type of covalent modification of the anti-podocalyxin antibody included within the scope of this invention comprises altering the native glycosylation pattern of the antibody or polypeptide. "Altering the native glycosylation pattern" is intended for purposes herein to mean deleting one or more carbohydrate moieties found in native sequence anti-podocalyxin antibody (either by removing the underlying glycosylation site or by deleting the glycosylation by chemical and/or enzymatic means), and/or adding one or more glycosylation sites that are not present in the native sequence anti-podocalyxin antibody. In addition, the phrase includes qualitative changes in the glycosylation of the native proteins, involving a change in the nature and proportions of the various carbohydrate moieties present.

Glycosylation of antibodies and other polypeptides is typically either N-linked or 0-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the anti-podocalyxin antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-podocalyxin antibody (for O-linked glycosylation sites). The anti-podocalyxin antibody amino acid sequence may optionally be altered through changes at the DNA level, particularly by mutating the DNA encoding the anti-podocalyxin antibody at preselected bases such that codons are generated that will translate into the desired amino acids.

Another means of increasing the number of carbohydrate moieties on the anti-podocalyxin antibody is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on the anti-podocalyxin antibody may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

As will be appreciated by the reasonably skilled artisan, substitutions and modifications may be made as is known in the art of ADC.

E. Preparation of Anti-Podocalyxin Antibodies

The description below relates primarily to production of anti-podocalyxin antibodies by culturing cells transformed or transfected with a vector containing anti-podocalyxin antibody-encoding nucleic acid. It is, of course, contemplated that alternative methods, which are well known in the art, may be employed to prepare anti-podocalyxin antibodies. For instance, the appropriate amino acid sequence, or portions thereof, may be produced by direct peptide synthesis using solid-phase techniques [see, e.g., Stewart et al., Solid-Phase Peptide Synthesis, W.H. Freeman Co., San Francisco, Calif. (1969); Merrifield, J. Am. Chem. Soc., 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the anti-podocalyxin antibody may be chemically synthesized separately and combined using chemical or enzymatic methods to produce the desired anti-podocalyxin antibody.

1. Isolation of DNA Encoding Anti-Podocalyxin Antibody

DNA encoding anti-podocalyxin antibody may be obtained from a cDNA library prepared from tissue believed to possess the anti-podocalyxin antibody mRNA and to express it at a detectable level. Accordingly, human anti-podocalyxin antibody DNA can be conveniently obtained from a cDNA library prepared from human tissue. The anti-podocalyxin antibody-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding anti-Podocalyxin antibody is to use PCR methodology [Sambrook et al., supra; Dieffenbach et al., PCR Primer: A Laboratory Manual (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like 32P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-podocalyxin antibody production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation, which means introduction of DNA into the host so that the DNA is replicable, either as an extrachromosomal or by chromosomal integrant, are known to the ordinarily skilled artisan, for example, $CaCl_2$, $CaPO_4$, liposome-mediated, polyethylene-gycol/DMSO and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transfections have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527-537 (1990) and Mansour et al., Nature, 336:348-352 (1988).

Suitable host cells for cloning or expressing the DNA in the vectors herein include prokaryote, yeast, or higher eukaryote cells.

a. Prokaryotic Host Cells

Suitable prokaryotes include but are not limited to archaebacteria and eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa, Rhizobia, Vitreoscilla, Paracoccus* and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 (Bachmann, Cellular and Molecular Biology, vol. 2 (Washington, D.C.: American Society for Microbiology, 1987), pp. 1190-1219; ATCC Deposit No. 27,325) may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kanr; *E. coli* W3110 strain 37D6, which has the complete genotype tonA ptr3 phoA E15 (argF-lac)169 degP ompT rbs7 ilvG kanr; *E. coli* W3110 strain 40B4, which is strain 37D6 with a non-kanamycin resistant degP deletion mutation; *E. coli* W3110 strain 33D3 having genotype W3110 ΔfhuA (ΔtonA) ptr3 lac Iq lacL8 ΔompTΔ(nmpc-fepE) degP41 kanR (U.S. Pat. No. 5,639,635) and an *E. coli* strain having mutant periplasmic protease disclosed in U.S. Pat. No. 4,946,783 issued 7 Aug. 1990. Other strains and derivatives thereof, such as *E. coli* 294 (ATCC 31,446), *E. coli* B, *E. coli*λ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. 5,840,523 (Simmons et al.) which describes translation initiation regio (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

b. Eukaryotic Host Cells

In addition to prokaryotes, eukaryotic microbes such as filamentous fungi or yeast are suitable cloning or expression hosts for anti-podocalyxin antibody-encoding vectors. *Saccharomyces cerevisiae* is a commonly used lower eukaryotic host microorganism. Others include *Schizosaccharomyces pombe* (Beach and Nurse, Nature, 290: 140 [1981]; EP 139,383 published 2 May 1985); *Kluyveromyces* hosts (U.S. Pat. No. 4,943,529; Fleer et al., Bio/Technology, 9:968-975 (1991)) such as, e.g., *K. lactis* (MW98-8C, CBS683, CBS4574; Louvencourt et al., J. Bacteriol., 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., Bio/Technology, 8:135 (1990)), *K. thermotolerans*, and *K. marxianus; Yarrowia* (EP 402,226); *Pichia pastoris* (EP 183,070; Sreekrishna et al., J. Basic Microbiol., 28:265-278 [1988]); *Candida; Trichoderma reesia* (EP 244,234); *Neurospora crassa* (Case et al., Proc. Natl. Acad. Sci. USA, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., Biochem. Biophys. Res. Commun., 112:284-289 [1983]; Tilburn et al., Gene, 26:205-221 [1983]; Yelton et al., Proc. Natl. Acad. Sci. USA, 81: 1470-1474 [1984]) and *A. niger* (Kelly and Hynes, EMBO J., 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, The Biochemistry of Methylotrophs, 269 (1982).

Suitable host cells for the expression of glycosylated anti-podocalyxin antibody are derived from multicellular organisms. Examples of invertebrate cells include insect cells such as *Drosophila* S2 and *Spodoptera* Sf9, as well as plant cells, such as cell cultures of cotton, corn, potato, soybean, *petunia*, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-podocalyxin antibody production and cultured in conventional nutrient media modified as appropriate for inducing promoters, selecting transformants, or amplifying the genes encoding the desired sequences.

3. Selection and Use of a Replicable Vector

For recombinant production of an antibody of the invention, the nucleic acid (e.g., cDNA or genomic DNA) encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The podocalyxin may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-podocalyxin antibody-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the C. albicans glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

a. Prokaryotic Host Cells

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides.

In general, plasmid vectors containing replicon and control sequences which are derived from species compatible with the host cell are used in connection with these hosts. Both expression and cloning vectors contain a nucleic acid sequence that enables the vector to replicate in one or more selected host cells, as well as marking sequences which are capable of providing phenotypic selection in transformed cells. Such sequences are well known for a variety of bacteria, yeast, and viruses. The origin of replication from the plasmid pBR322, which contains genes encoding ampicillin (Amp) and tetracycline (Tet) resistance and thus provides easy means for identifying transformed cells, is suitable for most Gram-negative bacteria, the 2μ plasmid origin is suitable for yeast, and various viral origins (SV40, polyoma, adenovirus, VSV or BPV) are useful for cloning vectors in mammalian cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters recognized by a variety of potential host cells are well known. Promoters suitable for use with prokaryotic hosts include the PhoA promoter, the β-galactamase and lactose promoter systems [Chang et al., Nature, 275:615 (1978); Goeddel et al., Nature, 281:544 (1979)], alkaline phosphatase, a tryptophan (trp) promoter system [Goeddel, Nucleic Acids Res., 8:4057 (1980); EP 36,776] and hybrid promoters such as the tac [deBoer et al., Proc. Natl. Acad. Sci. USA, 80:21-25 (1983)] or the trc promoter. Promoters for use in bacterial systems also will contain a Shine-Dalgarno (S.D.) sequence operably linked to the DNA encoding anti-podocalyxin antibody. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB− strains) provide cytoplasm conditions that are favorable for disulfide bond formation, thereby permitting proper folding and assembly of expressed protein subunits. Proba and Pluckthun Gene, 159:203 (1995).

The present invention provides an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

Preferably, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

b. Eukaryotic Host Cells

The vector components generally include, but are not limited to, one or more of the following: a signal sequence, an origin of replication, one or more marker genes, an enhancer element, a promoter, and a transcription termination sequence.

(1) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(2) Origin of Replication

Generally, an origin of replication component is not needed for mammalian expression vectors. For example, the SV40 origin may typically be used only because it contains the early promoter.

(3) Selection Gene Component

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

An example of suitable selectable markers for mammalian cells are those that enable the identification of cells competent to take up the anti-Podocalyxin antibody-encoding nucleic acid, such as DHFR or thymidine kinase, metallothionein-I and -II, preferably primate metallothionein genes, adenosine deaminase, ornithine decarboxylase, etc. An appropriate host cell when wild-type DHFR is employed is the CHO cell line deficient in DHFR activity (e.g., ATCC CRL-9096), prepared and propagated as described by Urlaub et al., Proc. Natl. Acad. Sci. USA, 77:4216 (1980). For example, cells transformed with the DHFR selection gene are first identified by culturing all of the transformants in a culture medium that contains methotrexate (Mtx), a competitive antagonist of DHFR. Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 [Stinchcomb et al., Nature, 282:39 (1979); Kingsman et al., Gene, 7:141 (1979); Tschemper et al., Gene, 10:157 (1980)]. The trp1 gene provides a selection marker for a mutant strain of yeast lacking the ability to grow in tryptophan, for example, ATCC No. 44076 or PEP4-1 [Jones, Genetics, 85:12 (1977)].

(4) Promoter Component

Expression and cloning vectors usually contain a promoter operably linked to the anti-Podocalyxin antibody-encoding nucleic acid sequence to direct mRNA synthesis. Promoters recognized by a variety of potential host cells are well known.

Virtually alleukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase [Hitzeman et al., J. Biol. Chem., 255:2073 (1980)] or other glycolytic enzymes [Hess et al., J. Adv. Enzyme Reg., 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Anti-podocalyxin antibody transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human γ-interferon cDNA in mouse cells under the control of a thymidine kinase promoter from herpes simplex virus. Alternatively, the Rous Sarcoma Virus long terminal repeat can be used as the promoter.

(5) Enhancer Element Component

Transcription of a DNA encoding the anti-podocalyxin antibody by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the anti-podocalyxin antibody coding sequence, but is preferably located at a site 5' from the promoter.

(6) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-Podocalyxin antibody. One useful transcription termination component is the bovine growth hormone polyadenylation region. See WO94/11026 and the expression vector disclosed therein.

Still other methods, vectors, and host cells suitable for adaptation to the synthesis of anti-podocalyxin antibody in recombinant vertebrate cell culture are described in Gething et al., Nature, 293:620-625 (1981); Mantei et al., Nature, 281:40-46 (1979); EP 117,060; and EP 117,058.

4. Culturing the Host Cells

The host cells used to produce the anti-Podocalyxin antibody of this invention may be cultured in a variety of media.

a. Prokaryotic Host Cells

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Ane et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some E. coli protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, E. coli strains deficient for proteolytic enzymes and transformed with plasmids overexpressing one or more chaperone proteins are used as host cells in the expression system of the invention.

b. Eukaryotic Host Cells

Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927, 762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence Podocalyxin polypeptide or against a synthetic peptide based on the DNA sequences provided herein or against exogenous sequence fused to Podocalyxin DNA and encoding a specific antibody epitope.

6. Purification of Anti-Podocalyxin Antibody

Forms of anti-podocalyxin antibody may be recovered from culture medium or from host cell lysates. If membrane-bound, it can be released from the membrane using a suitable detergent solution (e.g. Triton-X 100) or by enzymatic cleavage. Cells employed in expression of anti-Podocalyxin antibody can be disrupted by various physical or chemical means, such as freeze-thaw cycling, sonication, mechanical disruption, or cell lysing agents.

It may be desired to purify anti-podocalyxin antibody from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-podocalyxin antibody. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular anti-podocalyxin antibody produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies which are secreted to the periplasmic space of $E.$ $coli$. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

F. Pharmaceutical Formulations

The antibodies of the invention may be administered by any route appropriate to the condition to be treated. The antibody will typically be administered parenterally, i.e. infusion, subcutaneous, intramuscular, intravenous, intradermal, intrathecal and epidural.

For treating these cancers, in one embodiment, the antibody is administered via intravenous infusion. The dosage administered via infusion is in the range of about 1 µg/m2 to about 10,000 µg/m$^2$ per dose, generally one dose per week for a total of one, two, three or four doses. Alternatively, the dosage range is of about 1 µg/m$^2$ to about 1000 µg/m$^2$, about 1 µg/m$^2$ to about 800 µg/m$^2$, about 1 µg/m$^2$ to about 600 µg/m$^2$, about 1 µg/m$^2$ to about 400 µg/m$^2$, about 10 µg/m$^2$ to about 500 µg/m$^2$, about 10 µg/m$^2$ to about 300 µg/m$^2$, about 10 µg/m$^2$ to about 200 µg/m$^2$, and about 1 µg/m$^2$ to about 200 µg/m$^2$. The dose may be administered once per day, once per week, multiple times per week, but less than once per day, multiple times per month but less than once per day, multiple times per month but less than once per week, once per month or intermittently to relieve or alleviate symptoms of the disease. Administration may continue at any of the disclosed intervals until remission of the tumor or symptoms of the cancer being treated. Administration may continue after remission or relief of symptoms is achieved where such remission or relief is prolonged by such continued administration.

The invention also provides a method of treating breast cancer comprising administering to a patient suffering from breast cancer, a therapeutically effective amount of a humanized podocalyxin antibody of any one of the preceding embodiments. The antibody will typically be administered in a dosage range of about 1 µg/m$^2$ to about 1000 mg/m$^2$.

In one aspect, the invention further provides pharmaceutical formulations comprising at least one anti-podocalyxin antibody of the invention. In some embodiments, a pharmaceutical formulation comprises (1) an antibody of the invention, and (2) a pharmaceutically acceptable carrier.

Therapeutic formulations comprising an anti-podocalyxin antibody used in accordance with the present invention are prepared for storage by mixing the antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). Pharmaceutical formulations to be used for in vivo administration are generally sterile. This is readily accomplished by filtration through sterile filtration membranes.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

An antibody may be formulated in any suitable form for delivery to a target cell/tissue. For example, antibodies may be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA 82:3688 (1985); Hwang et al., Proc. Natl Acad. Sci. USA 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257:286-288 (1982) via a disulfide interchange reaction. A chemotherapeutic agent is optionally contained within the liposome. See Gabizon et al., J. National Cancer Inst. 81(19):1484 (1989).

The formulations to be used for in vivo administration must be sterile. This is readily accomplished by filtration through sterile filtration membranes.

G. Treatment with Anti-Podocalyxin Antibodies

To determine podocalyxin expression in the cancer, various detection assays are available. In one embodiment, podocalyxin polypeptide overexpression may be analyzed by immunohistochemistry (IHC). Parrafin embedded tissue sections from a tumor biopsy may be subjected to the IHC assay and accorded a podocalyxin protein staining intensity criteria.

Alternatively, or additionally, FISH assays such as the INFORMED (sold by Ventana, Ariz.) or PATHVISION® (Vysis, Ill.) may be carried out on formalin-fixed, paraffin-embedded tumor tissue to determine the extent (if any) of podocalyxin overexpression in the tumor.

Podocalyxin overexpression or amplification may be evaluated using an in vivo detection assay, e.g., by administering a molecule (such as an antibody) which binds the molecule to be detected and is tagged with a detectable label (e.g., a radioactive isotope or a fluorescent label) and externally scanning the patient for localization of the label.

As described above, the anti-podocalyxin antibodies of the invention have various non-therapeutic applications. The anti-podocalyxin antibodies of the present invention can be useful for staging of podocalyxin polypeptide-expressing cancers (e.g., in radioimaging). The antibodies are also useful for purification or immunoprecipitation of podocalyxin polypeptide from cells, for detection and quantitation of podocalyxin polypeptide in vitro, e.g., in an ELISA or a Western blot, to kill and eliminate podocalyxin-expressing cells from a population of mixed cells as a step in the purification of other cells.

Currently, depending on the stage of the cancer, cancer treatment involves one or a combination of the following therapies: surgery to remove the cancerous tissue, radiation therapy, and chemotherapy. Anti-podocalyxin antibody therapy may be especially desirable in elderly patients who do not tolerate the toxicity and side effects of chemotherapy well and in metastatic disease where radiation therapy has limited usefulness. The tumor targeting anti-podocalyxin antibodies of the invention are useful to alleviate podocalyxin-expressing cancers upon initial diagnosis of the disease or during relapse.

The anti-podocalyxin antibodies are administered to a human patient, in accord with known methods, such as intravenous administration, e.g., as a bolus or by continuous infusion over a period of time, by intramuscular, intraperitoneal, intracerebrospinal, subcutaneous, intra-articular, intrasynovial, intrathecal, oral, topical, or inhalation routes. Intravenous or subcutaneous administration of the antibody is preferred.

The antibody composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 µg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-podocalyxin antibody. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

The anti-podocalyxin antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, and functional fragments thereof. In fusion antibodies an antibody sequence is fused to a heterologous polypeptide sequence. The antibodies can be modified in the Fc region to provide desired effector functions. As discussed in more detail in the sections herein, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody (i) competes for binding to the same epitope, and/or (ii) binds substantially to the same epitope, as the antibodies of the invention. Antibodies having the biological characteristics of the present anti-podocalyxin antibodies of the invention are also contemplated, specifically including the in vivo tumor targeting and any cell proliferation inhibition or cytotoxic characteristics.

Methods of producing the above antibodies are described in detail herein.

The present anti-podocalyxin antibodies are useful for treating a podocalyxin-expressing cancer or alleviating one or more symptoms of the cancer in a mammal. The cancers encompass metastatic cancers of any of the cancers described herein. The antibody is able to bind to at least a portion of the cancer cells that express podocalyxin polypeptide in the mammal. In a preferred embodiment, the antibody is effective to destroy or kill podocalyxin-expressing tumor cells or inhibit the growth of such tumor cells, in vitro or in vivo, upon binding to podocalyxin polypeptide on the cell. In other preferred embodiments, the antibodies are effective to (i) inhibit the growth or proliferation of a cell to which they bind; (ii) induce the death of a cell to which they bind; (iii) inhibit the delamination of a cell to which they bind; (iv) inhibit the metastasis of a cell to which they bind; or (v) inhibit the vascularization of a tumor comprising a cell to which they bind.

The invention provides a composition comprising an anti-podocalyxin antibody of the invention, and a carrier. The invention also provides formulations comprising an anti-podocalyxin antibody of the invention, and a carrier. In one embodiment, the formulation is a therapeutic formulation comprising a pharmaceutically acceptable carrier.

Another aspect of the invention is isolated nucleic acids encoding the anti-Podocalyxin antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a podocalyxin polypeptide-expressing cancer or alleviating one or more symptoms of the cancer in a mammal, comprising administering a therapeutically effective amount of an anti-podocalyxin antibody to the mammal. The antibody therapeutic compositions can be administered short term (acute) or chronic, or intermittent as directed by physician. Also provided are methods of inhibiting the growth of, and killing a podocalyxin polypeptide-expressing cell.

The invention also provides kits and articles of manufacture comprising at least one anti-podocalyxin antibody. Kits containing anti-podocalyxin antibodies find use, e.g., for podocalyxin cell killing assays, for purification or immunoprecipitation of podocalyxin polypeptide from cells. For example, for isolation and purification of podocalyxin, the kit can contain an anti-podocalyxin antibody coupled to beads (e.g., sepharose beads). Kits can be provided which contain the antibodies for detection and quantitation of podocalyxin in vitro, e.g., in an ELISA or a Western blot. Such antibody useful for detection may be provided with a label such as a fluorescent or radiolabel.

H. Articles of Manufacture and Kits

Another embodiment of the invention is an article of manufacture containing materials useful for the treatment, prevention and/or diagnosis of podocalyxin-expressing cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating, preventing and/or diagnosing the cancer condition and may have a sterile access port (for example the container may be an intravenous solution bag or a vial having a stopper pierceable by a hypodermic injection needle). At least one active agent in the composition is an anti-podocalyxin antibody of the invention. The label or package insert indicates that the composition is used for treating cancer. The label or package insert will further comprise instructions for administering the antibody composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for podocalyxin-expressing cell killing assays, for purification or immunoprecipitation of podocalyxin polypeptide from cells. For isolation and purification of podocalyxin polypeptide, the kit can contain an anti-podocalyxin antibody coupled to beads (e.g., sepharose beads). Kits can be provided which contain the antibodies for detection and quantitation of podocalyxin polypeptide in vitro, e.g., in an ELISA or a Western blot. As with the article of manufacture, the kit comprises a container and a label or package insert on or associated with the container. The container holds a composition comprising at least one anti-podocalyxin antibody of the invention. Additional containers may be included that contain, e.g., diluents and buffers, control antibodies. The label or package insert may provide a description of the composition as well as instructions for the intended in vitro or detection use.

I. Method of Screening

Yet another embodiment of the present invention is directed to a method of determining the presence of a podocalyxin polypeptide in a sample suspected of containing the podocalyxin polypeptide, wherein the method comprises exposing the sample to an antibody that binds to the podocalyxin polypeptide and determining binding of the antibody to the podocalyxin polypeptide in the sample, wherein the presence of such binding is indicative of the presence of the podocalyxin polypeptide in the sample. Optionally, the sample may contain cells (which may be cancer cells) suspected of expressing the podocalyxin polypeptide. The antibody employed in the method may optionally be detectably labeled, attached to a solid support, or the like.

Another embodiment of the present invention is directed to a method of diagnosing the presence of a tumor in a mammal, wherein the method comprises (a) contacting a test sample comprising tissue cells obtained from the mammal with an antibody that binds to a podocalyxin polypeptide and (b) detecting the formation of a complex between the antibody and the podocalyxin polypeptide in the test sample, wherein the formation of a complex is indicative of the presence of a tumor in the mammal. Optionally, the antibody is detectably labeled, attached to a solid support, or the like, and/or the test sample of tissue cells is obtained from an individual suspected of having a cancerous tumor. Antibody detection can be achieved via different techniques as described herein, e.g., IHC and PET imaging.

IV. Further Methods of Using Anti-Podocalyxin Antibodies

A. Therapeutic Methods

An antibody of the invention may be used in, for example, in vitro, ex vivo, and in vivo therapeutic methods. In one aspect, the invention provides methods for inhibiting cell growth or proliferation, either in vivo or in vitro, the method comprising exposing a cell to an anti-podocalyxin antibody under conditions permissive for binding of the antibody to podocalyxin. "Inhibiting cell growth or proliferation" means decreasing a cell's growth or proliferation by at least 10%, 20%, 30%, 40%, 50%, 60%, 70%, 80%, 90%, 95%, or 100%, and includes inducing cell death. In certain embodiments, the cell is a tumor cell. In certain embodiments, the cell is a B cell. In certain embodiments, the cell is a xenograft, e.g., as exemplified herein. The antibodies may also (i) inhibit the growth or proliferation of a cell to which they bind; (ii) induce the death of a cell to which they bind; (iii) inhibit the delamination of a cell to which they bind; (iv) inhibit the metastasis of a cell to which they bind; or (v) inhibit the vascularization of a tumor comprising a cell to which they bind.

In one aspect, an antibody of the invention is used to treat or prevent a cell proliferative disorder. In certain embodiments, the cell proliferative disorder is associated with increased expression and/or activity of podocalyxin. For example, in certain embodiments, the cell proliferative disorder is associated with increased expression of podocalyxin on the surface of a cell. In certain embodiments, the cell proliferative disorder is a tumor or a cancer.

In one aspect, the invention provides methods for treating a cell proliferative disorder comprising administering to an individual an effective amount of an anti-podocalyxin antibody.

In one embodiment, an anti-podocalyxin antibody can be used in a method for binding podocalyxin in an individual suffering from a disorder associated with increased podocalyxin expression and/or activity, the method comprising administering to the individual the antibody such that podocalyxin in the individual is bound. In one embodiment, the podocalyxin is human podocalyxin, and the individual is a human individual. An anti-podocalyxin antibody can be administered to a human for therapeutic purposes. Moreover, an anti-podocalyxin antibody can be administered to a non-human mammal expressing podocalyxin with which the antibody cross-reacts (e.g., a primate, pig, rat, or mouse) for veterinary purposes or as an animal model of human disease. Regarding the latter, such animal models may be useful for evaluating the therapeutic efficacy of antibodies of the invention (e.g., testing of dosages and time courses of administration).

An antibody of the invention (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

B. Activity Assays

Anti-podocalyxin antibodies of the invention may be characterized for their physical/chemical properties and/or biological activities by various assays known in the art.

1. Activity Assays

In one aspect, assays are provided for identifying anti-podocalyxin antibodies thereof having biological activity. Biological activity may include, e.g., the ability to inhibit cell growth or proliferation (e.g., "cell killing" activity), or the ability to induce cell death, including programmed cell death (apoptosis). Antibodies having such biological activity in vivo and/or in vitro are also provided.

In certain embodiments, an anti-podocalyxin antibody is tested for its ability to inhibit cell growth or proliferation in vitro. Assays for inhibition of cell growth or proliferation are well known in the art. Certain assays for cell proliferation, exemplified by the "cell killing" assays described herein, measure cell viability. One such assay is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) J. Immunol. Meth. 160:81-88, U.S. Pat. No. 6,602,677. The assay may be conducted in 96- or 384-well format, making it amenable to automated high-throughput screening (HTS). See Cree et al (1995) AntiCancer Drugs 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

Another assay for cell proliferation is the "MTT" assay, a colorimetric assay that measures the oxidation of 3-(4,5-dimethylthiazol-2-yl)-2,5-diphenyltetrazolium bromide to formazan by mitochondrial reductase. Like the CellTiter-Glo™ assay, this assay indicates the number of metabolically active cells present in a cell culture. See, e.g., Mosmann (1983) J. Immunol. Meth. 65:55-63, and Zhang et al. (2005) Cancer Res. 65:3877-3882.

In one aspect, an anti-podocalyxin antibody is tested for its ability to induce cell death in vitro. Assays for induction of cell death are well known in the art. In some embodiments, such assays measure, e.g., loss of membrane integrity as indicated by uptake of propidium iodide (PI), trypan blue (see Moore et al. (1995) Cytotechnology, 17:1-11), or 7AAD. In an exemplary PI uptake assay, cells are cultured in Dulbecco's Modified Eagle Medium (D-MEM):Ham's F-12 (50:50) supplemented with 10% heat-inactivated FBS (Hyclone) and 2 mM L-glutamine. Thus, the assay is performed in the absence of complement and immune effector cells. Cells are seeded at a density of $3\times10^6$ per dish in 100×20 mm dishes and allowed to attach overnight. The medium is removed and replaced with fresh medium alone or medium containing various concentrations of the antibody. The cells are incubated for a 3-day time period. Following treatment, monolayers are washed with PBS and detached by trypsinization. Cells are then centrifuged at 1200 rpm for 5 minutes at 4 degrees C., the pellet resuspended in 3 ml cold $Ca^{2+}$ binding buffer (10 mM Hepes, pH 7.4, 140 mM NaCl, 2.5 mM $CaCl_2$) and aliquoted into 35 mm strainer-capped 12×75 mm tubes (1 ml per tube, 3 tubes per treatment group) for removal of cell clumps. Tubes then receive PI (10 µg/ml). Samples are analyzed using a FACSCAN flow cytometer and FACSCONVERT CellQuest software (Becton Dickinson). Antibodies which induce statistically significant levels of cell death as determined by PI uptake are thus identified.

In one aspect, an anti-podocalyxin antibody is tested for its ability to induce apoptosis (programmed cell death) in vitro. An exemplary assay for antibodies that induce apoptosis is an annexin binding assay. In an exemplary annexin binding assay, cells are cultured and seeded in dishes as discussed in the preceding paragraph. The medium is removed and replaced with fresh medium alone or medium containing 0.001 to 10 µg/ml of the antibody. Following a three-day incubation period, monolayers are washed with PBS and detached by trypsinization. Cells are then centrifuged, resuspended in Ca2+ binding buffer, and aliquoted into tubes as discussed in the preceding paragraph. Tubes then receive labeled annexin (e.g. annexin V-FITC) (1 µg/ml). Samples are analyzed using a FACSCAN™ flow cytometer and FACSCONVERT™ CellQuest software (BD Biosciences). Antibodies that induce statistically significant levels of annexin binding relative to control are thus identified. Another exemplary assay for antibodies that induce apoptosis is a histone DNA ELISA colorimetric assay for detecting internucleosomal degradation of genomic DNA. Such an assay can be performed using, e.g., the Cell Death Detection ELISA kit (Roche, Palo Alto, Calif.).

Cells for use in any of the above in vitro assays include cells or cell lines that naturally express podocalyxin or that have been engineered to express podocalyxin. Such cells include tumor cells that overexpress podocalyxin relative to normal cells of the same tissue origin. Such cells also include cell lines (including tumor cell lines) that express podocalyxin and cell lines that do not normally express podocalyxin but have been transfected with nucleic acid encoding podocalyxin.

In one aspect, an anti-podocalyxin antibody thereof is tested for its ability to inhibit cell growth or proliferation in vivo. In certain embodiments, an anti-podocalyxin antibody thereof is tested for its ability to inhibit tumor growth in vivo. In vivo model systems, such as xenograft models, can be used for such testing. In an exemplary xenograft system, human tumor cells are introduced into a suitably immunocompromised non-human animal, e.g., a SCID mouse. An antibody of the invention is administered to the animal. The ability of the antibody to inhibit or decrease tumor growth is measured. In certain embodiments of the above xenograft system, the human tumor cells are tumor cells from a human patient. In certain embodiments, the human tumor cells are introduced into a suitably immunocompromised non-human animal by subcutaneous injection or by transplantation into a suitable site, such as a mammary fat pad.

2. Binding Assays and Other Assays

In one aspect, an anti-podocalyxin antibody is tested for its antigen binding activity. For example, in certain embodiments, an anti-podocalyxin antibody is tested for its ability to bind to podocalyxin expressed on the surface of a cell. A FACS assay may be used for such testing.

In one aspect, competition assays may be used to identify a monoclonal antibody that competes with a monoclonal antibody comprising the variable domains of SEQ ID NO: 3 and SEQ ID NO: 5 (FIG. 2) or a chimeric antibody comprising the variable domain of the monoclonal antibody comprising the sequences of SEQ ID NO: 3 and SEQ ID NO: 5 (FIG. 2) and constant domains from IgG1 for binding to podocalyxin. In certain embodiments, such a competing antibody binds to the same epitope (e.g., a linear or a conformational epitope) that is bound by a monoclonal antibody comprising the variable domains of SEQ ID NO: 3 and SEQ ID NO: 5 (FIG. 2) or a chimeric antibody comprising the variable domain of the monoclonal antibody comprising the sequences of SEQ ID NO: 3 and SEQ ID NO: 5 (FIG. 2) and constant domains from IgG1. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). Two antibodies are said to bind to the same epitope if each blocks binding of the other by 50% or more.

In one aspect, competition assays may be used to identify a monoclonal antibody that competes with a monoclonal antibody comprising the variable domains of SEQ ID NO: 39 and SEQ ID NO: 41 (FIG. 12) or a chimeric antibody comprising the variable domain of the monoclonal antibody comprising the sequences of SEQ ID NO: 39 and SEQ ID NO: 41 (FIG. 12) and constant domains from IgG1 for binding to podocalyxin. In certain embodiments, such a competing antibody binds to the same epitope (e.g., a linear or a conformational epitope) that is bound by a monoclonal antibody comprising the variable domains of SEQ ID NO: 39 and SEQ ID NO: 41 (FIG. 12) or a chimeric antibody comprising the variable domain of the monoclonal antibody comprising the sequences of SEQ ID NO: 39 and SEQ ID NO: 41 (FIG. 12) and constant domains from IgG1. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). Two antibodies are said to bind to the same epitope if each blocks binding of the other by 50% or more.

In one aspect, competition assays may be used to identify a monoclonal antibody that competes with a monoclonal antibody comprising the variable domains of SEQ ID NO: 33 and SEQ ID NO: 35 (FIG. 10) or a chimeric antibody comprising the variable domain of the monoclonal antibody comprising the sequences of SEQ ID NO: 33 and SEQ ID NO: 35 (FIG. 10) and constant domains from IgG1 for binding to podocalyxin. In certain embodiments, such a competing antibody binds to the same epitope (e.g., a linear or a conformational epitope) that is bound by a monoclonal antibody comprising the variable domains of SEQ ID NO: 33 and SEQ ID NO: 35 (FIG. 10) or a chimeric antibody comprising the variable domain of the monoclonal antibody comprising the sequences of SEQ ID NO: 33 and SEQ ID NO: 35 (FIG. 10) and constant domains from IgG1. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). Two antibodies are said to bind to the same epitope if each blocks binding of the other by 50% or more.

In one aspect, competition assays may be used to identify a monoclonal antibody that competes with a monoclonal antibody comprising the variable domains of SEQ ID NO: 33 and SEQ ID NO: 37 (FIG. 10) or a chimeric antibody comprising the variable domain of the monoclonal antibody comprising the sequences of SEQ ID NO: 33 and SEQ ID NO: 37 (FIG. 10) and constant domains from IgG1 for binding to podocalyxin. In certain embodiments, such a competing antibody binds to the same epitope (e.g., a linear or a conformational epitope) that is bound by a monoclonal antibody comprising the variable domains of SEQ ID NO: 33 and SEQ ID NO: 37 (FIG. 10) or a chimeric antibody comprising the variable domain of the monoclonal antibody comprising the sequences of SEQ ID NO: 33 and SEQ ID NO: 37 (FIG. 10) and constant domains from IgG1. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). Two antibodies are said to bind to the same epitope if each blocks binding of the other by 50% or more.

In an exemplary competition assay, immobilized podocalyxin is incubated in a solution comprising a first labeled antibody that binds to podocalyxin (e.g., a monoclonal antibody comprising the variable domains of SEQ ID NO: 3 and SEQ ID NO: 5 (FIG. 2) or a chimeric antibody comprising the variable domain of the monoclonal antibody comprising the sequences of SEQ ID NO: 3 and SEQ ID NO: 5 (FIG. 2) and constant domains from IgG1) and a second unlabeled antibody that is being tested for its ability to compete with the first antibody for binding to podocalyxin. The second antibody may be present in a hybridoma supernatant. As a control, immobilized podocalyxin is incubated in a solution comprising the first labeled antibody but not the second unlabeled antibody. After incubation under conditions permissive for binding of the first antibody to podocalyxin, excess unbound antibody is removed, and the amount of label associated with immobilized podocalyxin is measured. If the amount of label associated with immobilized podocalyxin is substantially reduced in the test sample relative to the control sample, then that indicates that the second antibody is competing with the first antibody for binding to podocalyxin. In certain embodiments, immobilized podocalyxin is present on the surface of a cell or in a membrane preparation obtained from a cell expressing podocalyxin on its surface.

In one aspect, purified anti-podocalyxin antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

The following examples are offered for illustrative purposes only, and are not intended to limit the scope of the present invention in any way.

All patent, patent application, and literature references cited in the present specification are hereby incorporated by reference in their entirety.

EXAMPLES

Example 1—Development of Therapeutic Antibodies Against Podocalyxin

Antibodies that have the ability to target podocalyxin on tumor cells and block its function have been developed. The antibodies have been observed to have favorable binding profiles based on flow cytometry screening of tumor cell lines known to highly express podocalyxin (MDA.MB-231, CAOV3, A172), tumor cell lines known to express low levels of podocalyxin (MCF-7, T47D, OVCAR10), normal endothelial cells (HUVEC), and human embryonic kidney 293 (HEK293) cells known to normally express podocalyxin. Based on the reactivity of the antibodies to podocalyxin by flow cytometry, certain candidate antibodies were selected for analysis in an in vivo tumor model to assess their effect on tumor progression.

Materials and Methods

Antibody Production.

Production of Rabbit Anti-Podocalyxin Antibody 83 (Ab-1)

Ab-1 was raised in New Zealand White Rabbits by sequential semi-monthly subcutaneous immunization with A-172 cells (20 million 1st injection, 10 million for subsequent injections—mixed with Aluminum Hydroxide (5 mg/injection)+CpG (ODN 1826) 20 ug/injection)—Cedarlane® Burlington, ON. 1 week following the 11th injection, the rabbit was euthanized and the spleen was harvested (Cedarlane). B cells were cultured and isolated as per Babcook et al., PNAS, 1996, Jul. 23; 93(15):7843-8. A-172 (purchased from ATCC® CRL-1620™).

Ab-1 was identified by screening the B Cell supernatants for binding to hPodocalyxin/Fc fusion protein by ELISA. In order to clone the antibody from cultured B cells, the frozen cells were thawed and analysed by hPodocalyxin/Fc hemolytic plaque assay. Isolated single B cells were lysed and antibody V-genes were amplified by RT-PCR. PCR products corresponding to matched antibody heavy and light chains were then cloned into human IgG1 constant region and Igκ constant region constructs (pTT5/IgG1, pTT5/Igk). To produce recombinant Ab-1, Ab-1 VH and VL chain plasmids were transfected into 293-6E cells using 293fectin. After 96 hours of secretion, the antibody-containing supernatant was cleared of cells by centrifugation and sterile filtration (0.22 um). Ab-1 was purified using HiTrap Protein G HP (GE healthcare).

FIG. 1 provides the amino acid sequence of human podocalyxin (Accession Nos. NM_001018111.2 and NP_001018121.1). FIG. 2 provides the nucleic acid sequence for the heavy chain variable region (SEQ ID NO:2); the amino acid sequence for the heavy chain variable region (SEQ ID NO:3); the nucleic acid sequence for the light chain variable region (SEQ ID NO:4); and the amino acid sequence for the light chain variable region (SEQ ID NO:5) of an anti-podocalyxin antibody (referred to herein as anti-PODO, Ab-1). Hypervariable regions are underlined for the heavy chain variable region (SEQ ID NOS: 6-8) and light chain variable region (SEQ ID NOS: 9-11). Table 2 shows the CDRs of anti-podocalyxin antibody 83 (Ab-1).

Production of Mouse Anti-Podocalyxin Antibody 3G2 (Ab-2)

Ab-2 (also referred to herein as 3G2, 3G2.2, or anti-podoclayxin antibody 3G2) was raisedBalb/c mice by sequential twice-weekly intraperitoneal immunization with soluble human Podocalyxin-hFc expressed from MDA-MB-231 transfectants (10 ug 1st injection, 5 ug for subsequent injections—mixed with Emulsigen (30% v/v)+CpG (ODN 1826) 5 ug/injection)—Cedarlane® Burlington, ON. On day 32 following the 1st injection, the mice were euthanized and the spleen was harvested (Cedarlane). Splenic B cells were fused with Sp2/0-Ag14 mouse myeloma cells (ATCC: CRL-1581™) by electro fusion.

Ab-2 was raised in Balb/c mice by sequential twice-weekly intraperitoneal immunization with soluble human Podocalyxin-hFc expressed from MDA-MB-231 transfectants (10 ug 1st injection, 5 ug for subsequent injections—mixed with Emulsigen (30% v/v)+CpG (ODN 1826) 5 ug/injection)—Cedarlane® Burlington, ON. On day 32 following the 1st injection, the mice were euthanized and the spleen was harvested (Cedarlane). Splenic B cells were fused with Sp2/0-Ag14 mouse myeloma cells (ATCC: CRL-1581™) by electro fusion.

Ab-2 was identified by screening the hybridoma Cell supernatants for binding to MDA-MB-231 cells using flow cytometry. In order to clone the antibody from cultured hybridoma cells, the frozen cells were thawed and subcloned by 3 rounds of limiting dilution. hPodocalyxin specific clones from clonal hybridoma cultures were isolated and binding specificity verified by flow cytometry using human Podocalyxin CHO-K1 transfectants. The V-genes were then amplified by RT-PCR, and sequenced by standard Sanger sequencing methods.

FIGS. 12A-D show the heavy and light chain sequences of the mouse 3G2 antibody. Table 3 shows the CDRs for anti-podocalyxin antibody 3G2.

TABLE 2

Anti-Podocalyxin Antibody 83 (Ab-1)

|         | IMGT                           | Chotia                          | Kabat                                |
|---------|--------------------------------|---------------------------------|--------------------------------------|
| VH CDR1 | GIDLSSYA (SEQ ID NO: 13)       | GIDLSSYAMG (SEQ ID NO: 12)      | SYAMG (SEQ ID NO: 6)                 |
| VH CDR2 | IYASGSI (SEQ ID NO: 15)        | FIYASGSI (SEQ ID NO: 14)        | FIYASGSIFYASWAKG (SEQ ID NO: 7)      |
| VH CDR3 | ARAGYYFGGNYDLNL (SEQ ID NO: 16) | AGYYFGGNYDLNL (SEQ ID NO: 8)    | AGYYFGGNYDLNL (SEQ ID NO: 8)         |
| Vk CDR1 | QSISNY (SEQ ID NO: 17)         | QASQSISNYLA (SEQ ID NO: 9)      | QASQSISNYLA (SEQ ID NO: 9)           |
| Vk CDR2 | RAS (SEQ ID NO: 18)            | RASTLAS (SEQ ID NO: 10)         | RASTLAS (SEQ ID NO: 10)              |
| Vk CDR3 | QQGYVSNNLDNI (SEQ ID NO: 11)   | QQGYVSNNLDNI (SEQ ID NO: 11)    | QQGYVSNNLDNI (SEQ ID NO: 11)         |

TABLE 3

Anti-Podocalyxin Antibody 3G2

| | IMGT | Chotia | Kabat |
|---|---|---|---|
| VH CDR1 | GYTFTSYV (SEQ ID NO: 21) | GYTFTSYVMH (SEQ ID NO: 20) | SYVMH (SEQ ID NO: 19) |
| VH CDR2 | IHPYNDGT (SEQ ID NO: 24) | YIHPYNDGT (SEQ ID NO: 23) | YIHPYNDGTNYNEKFKG (SEQ ID NO: 22) |
| VH CDR3 | ARSWDWYFDV (SEQ ID NO: 26) | SWDWYFDV (SEQ ID NO: 25) | SWDWYFDV (SEQ ID NO: 25) |
| Vk CDR1 | SNVRY (SEQ ID NO: 28) | SANSNVRYIH (SEQ ID NO: 27) | SANSNVRYIH (SEQ ID NO: 27) |
| Vk CDR2 | DTS (SEQ ID NO: 30) | DTSKLSS (SEQ ID NO: 29) | DTSKLSS (SEQ ID NO: 29) |
| Vk CDR3 | QQWISNPLT (SEQ ID NO: 31) | QQWISNPLT (SEQ ID NO: 31) | QQWISNPLT (SEQ ID NO: 31) |

Tumour cell line selectivity Panel staining. HUVEC cells were grown at CDRD in Millipore EndoGro-VEGF (Cat #SCME002). T47D (a cell line with very low level of podocalyxin expression as determined by western blot, data not shown), MCF-7 (a cell line with moderate level of podocalyxin expression as determined by western blot, data not shown), and MDA-MB-231 human breast carcinoma cell line (a cell line with very high level of podocalyxin expression as determined by western blot, data not shown) and Ovarian carcinoma-derived CaOV-3, OVCAR-3, OVCAR-8, and OVCAR-10 cells were grown in T75 Tissue culture flasks (BD Falcon #353136). The breast carcinoma cells were routinely maintained in DMEM/F12 medium (Sigma, St. Louis, Mo. cat #D6421) supplemented with 5% fetal bovine serum (FBS, Invitrogen, Carlsbad, Calif.) and insulin (5 µg/ml; Sigma, St. Louis, Mo. cat #19278). The Ovarian carcinoma-derived cells were routinely cultured in a 199/105 medium (Sigma, St. Louis, Mo. cat #s M4530/M6395) supplemented with 5% fetal bovine serum (FBS, invitrogen, Carlsbad, Calif.). A-172 (purchased from ATCC® CRL-1620™) were grown in T175 tissue culture flasks (BD Falcon 353112 at CDRD using DMEM (Gibco #10313-021)+10% Fetal Bovine Serum (FBS, Gibco #26140-079). 293 cells (293-6E, purchased from NCR-BRI) were grown in suspension (shaker flasks, Corning #431145) using FreeStyle™ 293 Expression Medium (Gibco #12338-018)+Pluronic (Gibco #24040-032). Adherent cells first had their medium aspirated, and then were washed using 5 mL sterile PBS (Gibco #100-10-049). The PBS wash was discarded and replaced by 3 mL of cell dissociation buffer (Sigma Cat #C5914). The cells were incubated at 37° C./5% $CO_2$ for 30 minutes. 7 mL DMEM+10% FBS was used to disperse the cells and the resulting 10 mL cell suspensions were transferred to 15 mL conical tubes (BD Falcon #352096). 293 cells were taken directly from their culture flask and were transferred to a 15 mL conical tube. The cell suspensions were counted using the ViCell (Beckman Coulter) and 15-50000 cells/well were seeded into V-bottom 96-well plates (Sarstedt #82.1583.001). Cells were pelleted by centrifugation at 400 g for 3 minutes. The supernatants were discarded. The cell pellets were then resuspended using 15 uL of 5 ug/mL protein G (GE: Protein G HP, 1 mL #17-0404-03) purified Anti-PODO (Rb/Hu Podo83) diluted in PBS+1% FBS (FACS buffer). Cells and antibody were incubated on ice for 1 hour. Wash Procedure: 200 uL ice cold FACS buffer added to each well, centrifuge the plate at 400 g for 3 minutes (4° C.) to pellet cells, discard the diluted primary antibody, resuspend the cell pellets in 200 uL FACS buffer, ensuring pellet is disrupted, centrifuge plate at 400 g for 3 minutes to pellet cells, discard the supernatant. To detect cell-bound primary antibody, the cells were then resuspended in 25 uL/well fluorescently-labelled secondary antibody (5 ug/mL, Goat anti-Human IgG-Fc Alexa Fluor® 647; Jackson ImmunoResearch #109-605-098) plus a viability dye (2 ug/mL, 7-actinomycin-D; Sigma #A9400) which were diluted together in FACS buffer. Incubate plates on ice for 0.5 hours. Repeat the same wash procedure as above. Resuspend each well in 100 uL FACS buffer and analyse by flow cytometry (IntelliCyt High-throughput Flow Cytometer, 3 second sip, 1.5 second up, 15 RPM pump speed). Results were analysed using IntelliCyt Hyperview Software. 7-actinomycin-D positive events (dead cells) were excluded from the analysis. The results are expressed as geometric mean fluorescence units.

| Selectivity Cell Line Panel (Live cell GeoMean FL) | | | | | | | | |
|---|---|---|---|---|---|---|---|---|
| HUVEC | MCF7 | MDA-MB-231 | T47-D | CaOV3 | OVCAR3 | OVCAR10 | A172 | 293 |
| 44611 | 60805 | 91909 | 1498 | 48817 | 16502 | 2824 | 169600 | 28225 |

MDA-MB-231 and MDA-MB-231/hPodo Transfectant staining. (FIG. 3) 150000 MDA-MB-231 (ATCC® HTB-26™) cells were seeded into each well of two 6-well tissue culture dishes (BD Falcon #353046) in 3 mL Leibovitz's L-15 medium. The cells were incubated overnight at 37° C. without $CO_2$. The following morning, the seeding medium was discard and was replaced with 2 mL fresh Leibovitz's L-15 medium. The cells in one dish were transfected with 2.5 ug human Podocalyxin (hPodo/pTT5) DNA using 6 uL Lipofectamine® LTX with 2.5 uL Plus™ Reagent (Life Technologies #15338100) in a total of 200 uL Opti-MEM® I medium (Life Technologies #31985-070) to generate MDA-MB-231/hPodo Transfectants. The transfection mix and cells as well as the dish containing the non-transfected cells were incubated overnight at 37° C. without $CO_2$. The following morning the transfection mix/medium was discarded, and the cells were washed with sterile PBS. The wash was discarded, and 1 mL Cell Dissociation Solution (Sigma) was added to the cells-incubated at 37° C. no $CO_2$ for 20 minutes. Each cell type was dispersed using 2 mL/well DMEM+10% FBS and contents of the 6 wells were pooled in separate 15 mL conical tubes. The cells were then counted using the ViCell and 50000 cells/well were seeded into V-bottom 96-well dishes. The cells were stained with anti-PODO (Rb/Hu Podo83) and control Rb/Hu IgG1 following the same protocol as above with the following modifications: Primary incubation volume=25 uL, 7-Actinomycin D concentration=2.5 ug/mL.

In vivo assessment of antibody efficacy. (Rb/Hu Podo83 was the anti-podocalyxin antibody used in all in vivo experiments) (FIG. 4) MDA.MB-231 cells fluorescently tagged with Red Flourescent Protein (RFP) were pre-treated with 25 μg per $10^6$ cells. Anti-PODO or non-specific control anti-OVA peptide antibodies were pre-incubated with tumor cells for 30 minutes at room temperature. The tumor cell/antibody mixture was diluted 2:1 in Matrigel™ on ice prior to injection. A total of $1\times10^6$ MDA.MB-231RFP cells were subcutaneously injected into the flank region of NSG mice. Tumor dimensions were measured every three days and tumor volumes ($mm^3$) were calculated by ((length×width$^2$)/2). On day 14 post-transplantation, mice were administered 100 μg of antibody by intraperitoneal injection twice weekly. On day 27 post-transplantation, mice were anesthetized with avertin and lungs were perfused with ice cold PBS. Lungs and tumors were excised. Final tumor volumes were calculated and tumors were weighed. Lungs were minced and digested in a solution of collagenase (2 mg/ml; Sigma, St Louis, Mo.) and 2 mg/mL dispase (2 mg/ml; Roche, Mannheim, GER) in HBSS for 1-2 hours at 37° C. to obtain a single cell suspension. The cellular suspension was then filtered through a 70 μm cell strainer, centrifuged at 453 rcf for 5 minutes, and red blood cell lysed in ammonium chloride solution (mCrb). Cells were washed in PBS, filtered and resuspended in FACS buffer (2% FBS, 2 mM EDTA, PBS, 0.05% NaAzide) prior to flow cytometry. The PE channel was used to detect RFP fluorescing MDA.MB-231 cells in the lung. A LSRII flow cytometry machine (BD Biosciences, Mississauga, ON) was used for all flow cytometric experiments.

Statistics. Data was expressed as means±standard error of the mean (SEM). Statistical analysis was performed using Prism 5 (GraphPAd Software). For comparisons between anti-OVA control and anti-PODO treated tumors the Student's t test was used, and for time-dependent studies of tumor development a two-way ANOVA was used. $P<0.05$ was considered to be statistically significant.

Figure 7A:
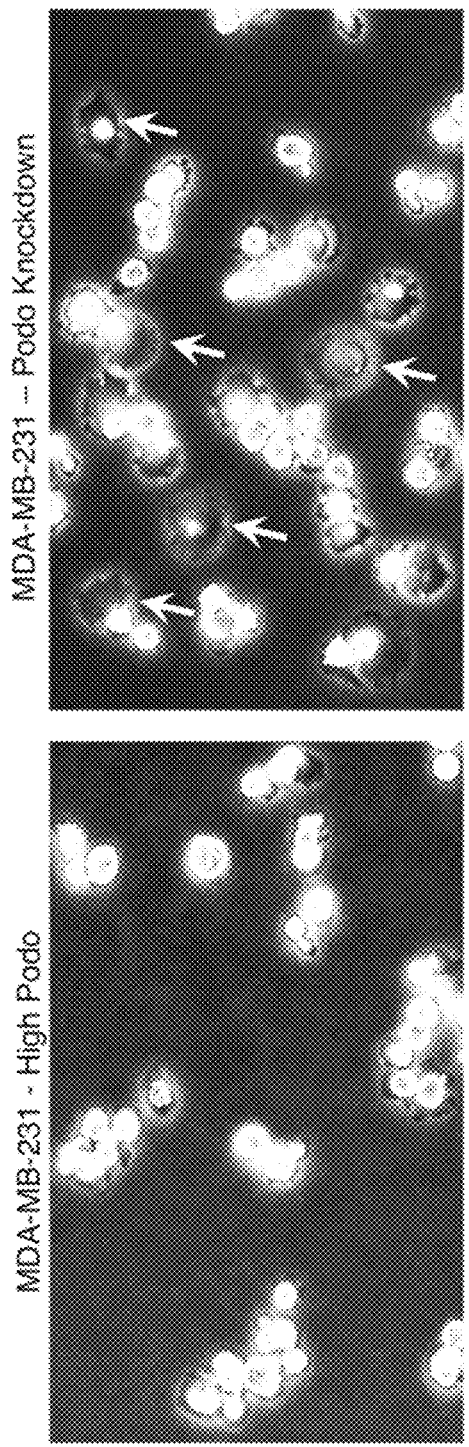
FIG. 7 A, B: Podocalyxin knockdown and Rb/Hu Podo83 (referred to as Ab-1 in this figure) increase MDA-MB-231 breast carcinoma cell spreading in vitro. A: Previously, we demonstrated that forced podocalyxin overexpression decreased carcinoma cell adhesion and spreading (Somasiri et al., 2004; Cipollone et al., 2012). Therefore, we reasoned that knocking down endogenous podocalyxin would do the opposite in MDA-MB-231 breast carcinoma cells. This is demonstrated in A, where the great majority of parental MDA-MB-231 cells that express high levels of endogenous podocalyxin, remained rounded and phase bright after they were plated in low serum conditions for one hour. In contrast, under the same conditions many of the MDA-MB-231 cells wherein endogenous podocalyxin was stably knocked down spread robustly as indicated by the fact that they became much larger in diameter and phase dark as they began to thin during spreading (arrows). B: The great majority of parental MDA-MB-231 cells treated with a control, irrelevant antibody (Ova-10; 50 μg/ml) remained rounded and phase bright after they were plated in low serum for 30 min. In contrast, many of the parental MDA-MB-231 cells treated with Rb/Hu Podo83 (50 μg/ml) spread robustly as indicated by the fact that they became larger in diameter and phase dark (arrows).
Figure 7B:
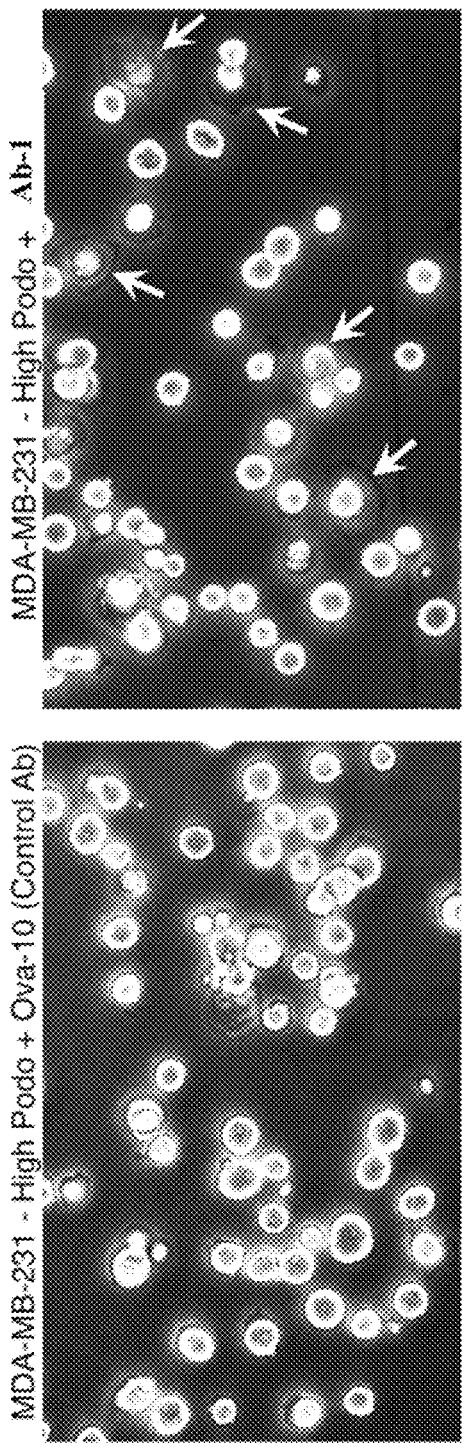
Figure 8B:
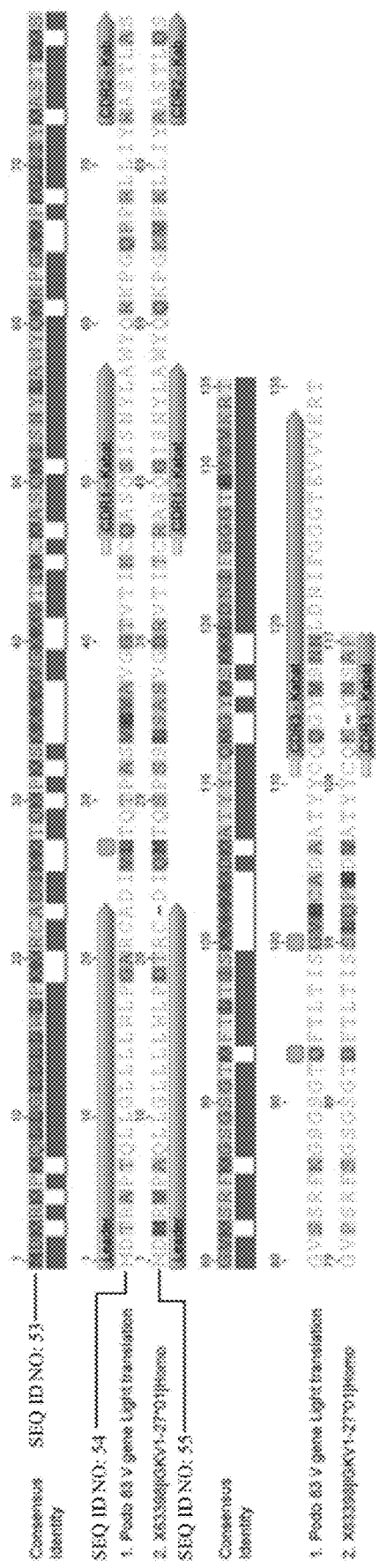
Figure 8D:
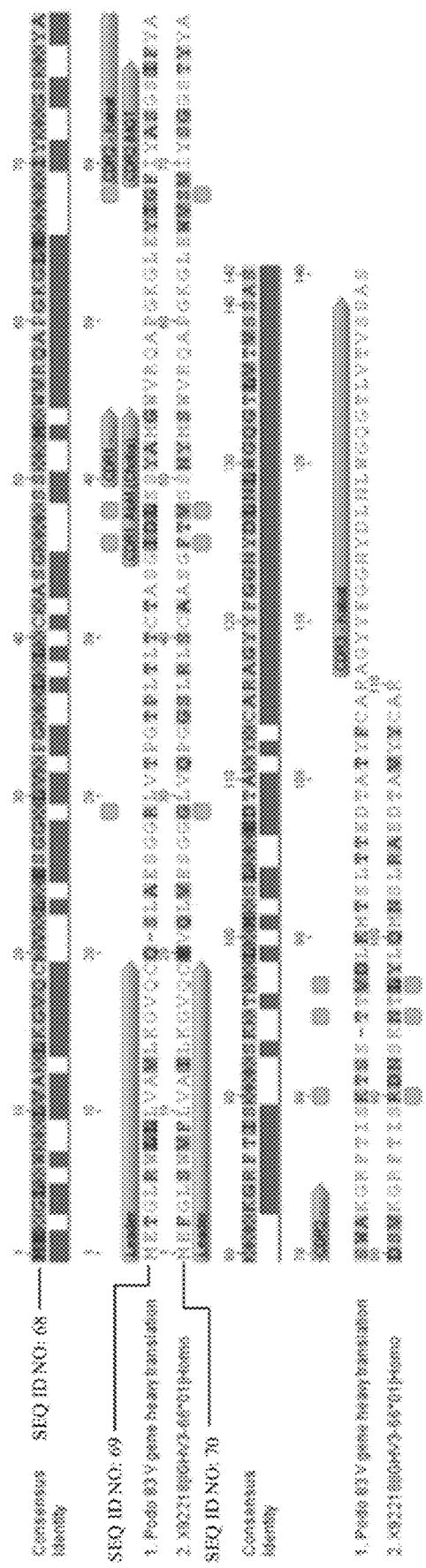

In Vitro Rb/Hu Podo83 Activity Methods (FIG. 7) MDA-MB-231 cells were dissociated with enzyme-free dissociation buffer (Life Technologies), resuspended in DMEM/F12 medium (Sigma) supplemented with 1% fetal bovine serum (Invitrogen), and plated in 12 well tissue culture wells (Gibco) at 25,000 cells per cm2. The plated cells were then maintained at 37° C. for the indicated times and photographed, live, by phase microscopy (Leica DMI 4000B).

Results

The specificity of the anti-podocalyxin Rb/Hu Podo83, as determined by its binding properties against various podocalyxin-expressing cell lines, is demonstrated in FIG. 3A-B. It is noted that the anti-PODO antibody is highly selective for podocalyxin and does not cross react with endoglycan or CD34.

Figure 4:
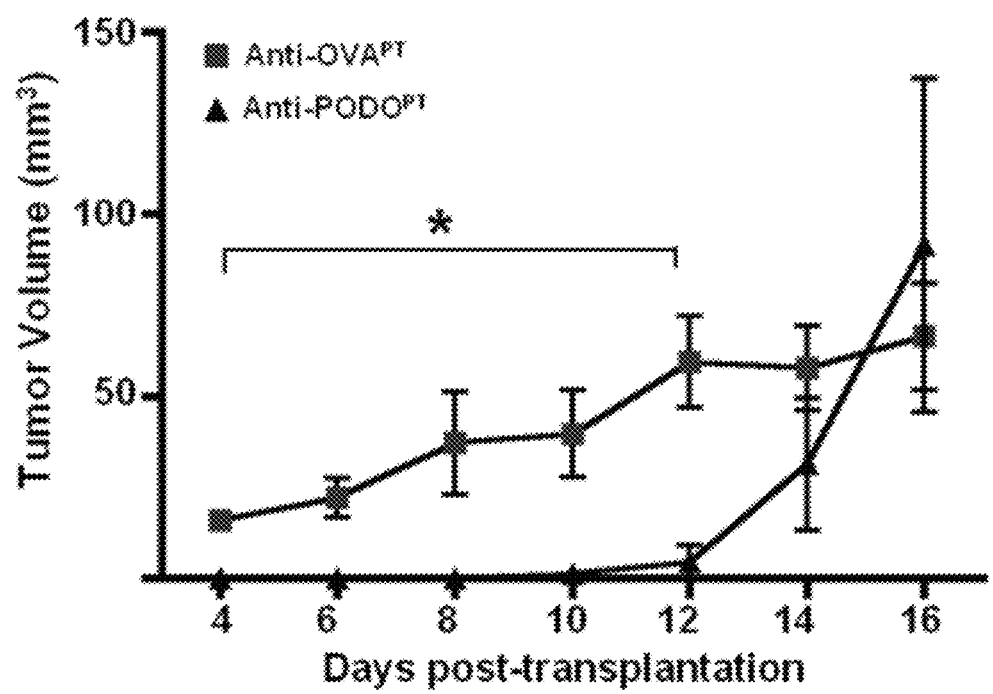
FIG. 4 illustrates the ability of an anti-podocalyxin antibody (anti-PODO; Rb/Hu Podo83) to delay primary tumor development. MDA.MB-231$^{RFP}$ cells were pre-treated with 25 µg/$10^6$ cells of the anti-PODO antibody or anti-OVA control antibody for 30 minutes at room temperature in vitro. A total of $1\times10^6$ MDA.MB-231$^{RFP}$ cells in a 2:1 mixture of Matrigel™ and HBSS were subcutaneously injected into the flanks of NSG mice. Tumors were measured every second day and tumor volume (mm$^3$) was calculated by the formula (length×width$^2$/2). The graph depicts volumes of tumors pre-treated with anti-OVA control (squares) or anti-PODO (triangles) antibody over time.

Anti-PODO was assessed for its ability to inhibit tumor formation in vivo by pre-treating MDA.MB-231 cells with experimental or control antibody in vitro prior to injection into NOD.Cg-PrkdcscidIl2rgtm1Wj1/SzJ (NSG) mice. Pre-treatment of the tumor cells with antibody was selected over the systemic treatment of established tumors in vivo, in order to maximize the ability to detect an effect with the limiting quantities of antibody available for screening. It was expected that pre-treatment with antibody would allow detection of any effects on initial tumor seeding. Anti-PODO was observed to significantly delay primary tumor development (FIG. 4). Pre-treatment of MDA.MB-231 cells with Anti-PODO (anti-PODO$^{PT}$) significantly delayed tumor development in vivo for the first twelve days post-implantation compared to anti-OVA control (anti-OVA$^{PT}$) (p=0.024 by two-way ANOVA; n=3). After twelve days in vivo, anti-PODO$^{PT}$ tumors began to rapidly increase in volume and by day sixteen were equal in volume to anti-OVA$^{PT}$ tumors. It is hypothesized that this was due to a gradual loss of injected antibody over time in the absence of subsequent treatment with antibody. Thus, this preliminary data suggests that anti-PODO pretreatment reduces tumor growth for as long as antibody is present.

Figure 5A:
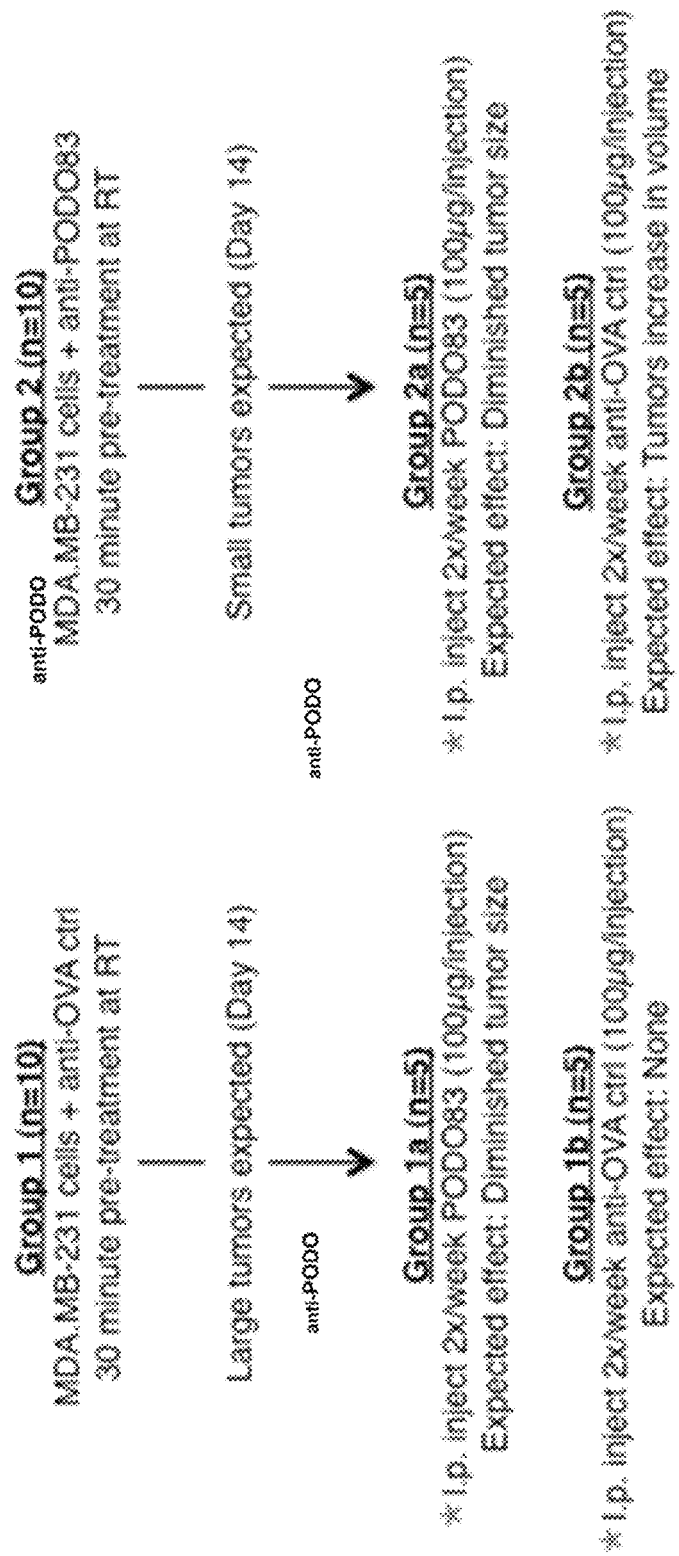
FIG. 5 A-E illustrates the effects of anti-podocalyxin antibody (Rb/Hu Podo83) treatment on tumor volume. MDA.MB-231$^{RFP}$ cells were pre-treated with 25 µg of anti-PODO (anti-PODO$^{PT}$) or anti-OVA control (anti-OVA$^{PT}$) per $10^6$ cells for 30 minutes at room temperature in vitro. A total of $1\times10^6$ anti-PODO$^{PT}$ or anti-OVA$^{PT}$ MDA.MB-231 cells in a 2:1 mixture of Matrigel™ and HBSS were subcutaneously injected into the flanks of NSG mice. Tumor dimensions were measured every third day and tumor volume (mm$^3$) was calculated by the formula (length×width$^2$/2). Starting on day 14 post-transplantation, 100 µg of anti-OVA (anti-OVA$^{sys}$) or anti-PODO (anti-PODO$^{sys}$) antibody (Rb/Hu Podo83) was injected intraperitoneally (i.p.) into NSG mice twice weekly (stars along x-axis) and tumor volumes were calculated until sacrifice. (A) Experimental flow chart showing antibody treatment schedules. (B) Tumor volumes (mm$^3$) measured over time until sacrifice for mice with anti-OVA$^{PT}$ tumors followed by anti-OVA$^{sys}$ treatment, anti-PODO$^{PT}$ tumors followed by anti-OVA$^{sys}$ treatment, anti-OVA$^{PT}$ tumors followed by anti-PODO$^{sys}$ treatment and anti-PODO$^{PT}$ tumors followed by anti-PODO$^{sys}$ treatment. (C) Volumes of anti-OVA$^{PT}$ and anti-PODO$^{PT}$ tumors measured from day five to fourteen post-transplantation. (D) Volumes of anti-OVA$^{PT}$ tumors treated systemically with anti-OVA control or anti-PODO antibody from primary administration to sacrifice. (E) Volumes of anti-PODO$^{PT}$ tumors treated systemically with anti-OVA control or anti-PODO antibody from primary administration of antibody to sacrifice.
Figures 5B, 5C:
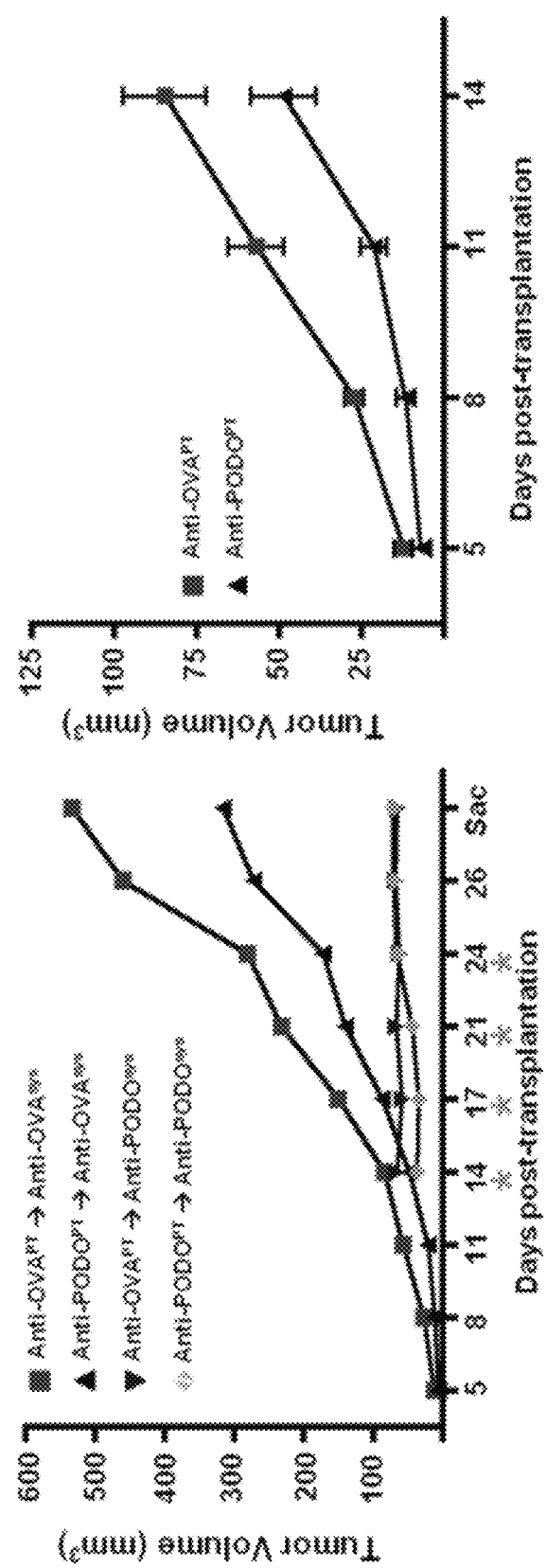
Figure 5D:
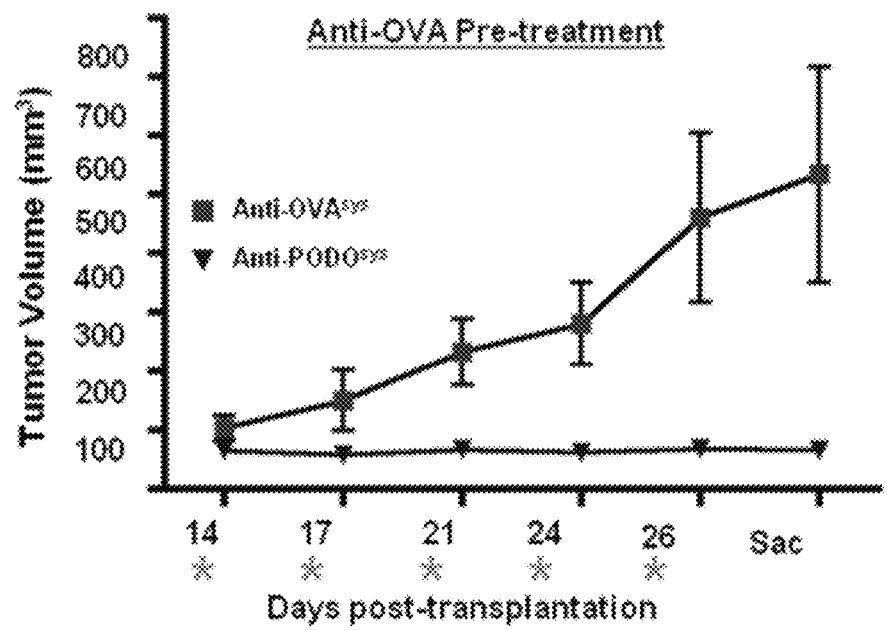
Figure 5E:
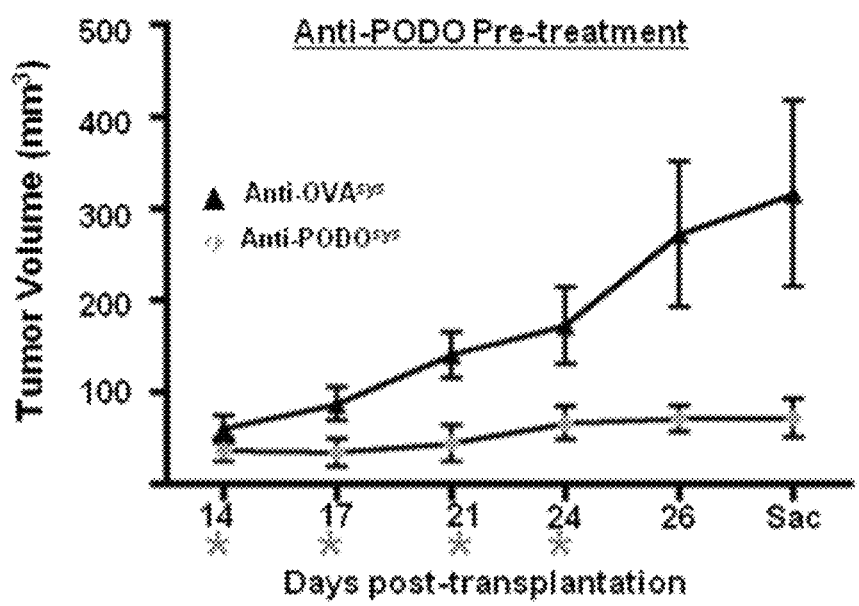

The production of anti-PODO antibody was scaled up in order to repeat the initial findings in a larger cohort of mice and to more thoroughly investigate the effects of this antibody when administered systemically to established tumors (See experimental flow chart—FIG. 5A). The overall effects of antibody treatment on tumor volume from initial transplantation to sacrifice are shown collectively (FIG. 5B). As before, anti-PODO$^{PT}$ MDA.MB-231RFP cells possessed delayed tumor development within the first eleven days of transplantation into NSG mice (FIG. 5C; p=0.0046 by two-way ANOVA; n=10). Again, it was observed that anti-PODO$^{PT}$ tumors reach similar volumes to anti-OVA$^{PT}$ tumors by day 14, likely reflecting a time when the antibody pre-treatment titers diminish. To assess the effect of antibody treatment on the development of established tumors, mice were also systemically treated with anti-OVA control or anti-PODO twice weekly from day fourteen onwards. Tumors pretreated with anti-OVA antibody were subsequently treated with anti-PODO at 14 days when they were firmly established. This resulted in complete inhibition of tumor growth. In contrast, systemic treatment of anti-OVA$^{PT}$ tumor bearing mice with anti-OVA control antibody had no such inhibitory effect on primary tumor development and tumors continue to rapidly increase in volume (FIG. 5D; p<0.0001 by two-way ANOVA; n=5). Likewise, systemic treatment of anti-PODO$^{PT}$ tumor bearing mice with systemic anti-PODO also resulted in complete inhibition of tumor growth. Conversely, systemic treatment of anti-PODO$^{PT}$ tumor bearing mice with anti-OVA control antibody had no such inhibitory effect on primary tumor development and these tumors continue to rapidly increase in volume over time (FIG. 5E; p<0.0001 by two-way ANOVA; n=5). Thus, pre-treatment of tumor cells with anti-PODO$^{PT}$ (prophylactic regimen) or post-treatment of established tumors (therapeutic regimen) dramatically delayed tumor growth.

Representative images of excised tumors from mice systemically treated with anti-OVA control or anti-PODO reveals a clear difference in the size of the primary tumors with anti-PODO treated tumors exhibiting significantly smaller, less vascularized tumors compared to anti-OVA control. (FIG. 6A and FIG. 6D). In addition, anti-OVA$^{PT}$ tumors from mice systemically treated with anti-PODO weigh 5.3-fold less than the anti-OVA systemic treatment group (Anti-OVA$^{PT}$ tumors weigh 0.42±0.15 g, whereas tumors from mice systemically treated with anti-PODO weigh 0.070±0.015 g (FIG. 6B; p=0.05 by unpaired Student's T test; n=5)). Likewise, while not reaching statistical significance, anti-PODO$^{PT}$ tumors from mice systemically treated with anti-PODO, weigh 3.6-fold less than tumors from the anti-OVA systemic treatment group. Anti-PODO$^{PT}$ tumors that had been systemically treated with anti-OVA antibody weigh 0.31±0.10 g, whereas tumors systemically treated with anti-PODO weigh 0.087±0.026 g (FIG. 6E; p=0.07 by unpaired Student's T test; n=5).

Finally, flow cytometry was used to assess the number of RFP-positive tumor cells that had successfully moved from the site of injection in the flank to the lung and it was found that the number of micrometastases within the lung positively correlates with primary tumor size. Thus, tumors with the largest volumes have the greatest number of detectable tumor cells within the lungs and therapeutic treatment with anti-PODO antibody resulted in fewer detectable tumor cells within the lung. In the lungs of mice with anti-OVA$^{PT}$ tumors and systemic treatment with anti-OVA control antibody, there was an average of 751±404 tumor cells per million lung cells detectable upon sacrifice. In anti-OVA$^{PT}$ tumors treated systemically with anti-PODO, 67.2±18.6 tumor cells per million lung cells were detectable (FIG. 6C; p=0.13 by unpaired Student's T test; n=5). In the lungs of mice pre-treated with anti-PODO$^{PT}$ tumors systemically treated with anti-OVA control antibody, an average of 759±419 tumor cells per million lung cells were detectable upon sacrifice. Finally, within the lungs of pretreated with anti-PODO mice and then systemically treated with anti-PODO, only 30.4±8.17 tumor cells per million lung cells were detectable (FIG. 6F; p=0.12 by unpaired Student's T test; n=5). In summary, therapeutic treatment of established tumors with anti-PODO antibody dramatically reduced the establishment of tumor cells at distal sites (lung) and this correlated directly with the size of the primary tumor size at the site of injection.

(FIG. 7) Podocalyxin knockdown and Rb/Hu Podo83 increase MDA-MB-231 breast carcinoma cell spreading in vitro. A: Previously, we demonstrated that forced podocalyxin overexpression decreased carcinoma cell adhesion and spreading (Somasiri et al., 2004; Cipollone et al., 2012). Therefore, we reasoned that knocking down endogenous podocalyxin would do the opposite in MDA-MB-231 breast carcinoma cells. This is demonstrated in A, where the great majority of parental MDA-MB-231 cells that express high levels of endogenous podocalyxin, remained rounded and phase bright after they were plated in low serum conditions for one hour. In contrast, under the same conditions many of the MDA-MB-231 cells wherein endogenous podocalyxin was stably knocked down spread robustly as indicated by the fact that they became much larger in diameter and phase dark as they began to thin during spreading (arrows). B: The great majority of parental MDA-MB-231 cells treated with a control, irrelevant antibody (Ova-10; 50 µg/ml) remained rounded and phase bright after they were plated in low serum for 30 min. In contrast, many of the parental MDA-MB-231 cells treated with Rb/Hu Podo83 (50 µg/ml) spread robustly as indicated by the fact that they became larger in diameter and phase dark (arrows).

See also Boman et al., Br J Cancer. 2013 Jun. 11; 108(11):2321-8, Membranous expression of podocalyxin-like protein is an independent factor of poor prognosis in urothelial bladder cancer; Larsson et al., BMC Cancer. 2012 Jul. 8; 12:282, Validation of podocalyxin-like protein as a biomarker of poor prognosis in colorectal cancer; Larsson et al., Br J Cancer. 2011 Aug. 23; 105(5):666-72, Overexpression of podocalyxin-like protein is an independent factor of poor prognosis in colorectal cancer; Cipollone et al., Clin Exp Metastasis. 2012 March; 29(3):239-52, The anti-adhesive mucin podocalyxin may help initiate the transperitoneal metastasis of high grade serous ovarian carcinoma.

Example 2—Humanized Anti-Podocalyxin Antibodies

Humanized antibodies have improved pharmacokinetics, reduced immunogenicity, and have been used to clinical advantage. Humanized antibodies of Ab-1 (also referred to herein as anti-podocalyxin antibody 83, or "83") described in Example 1 above that target podocalyxin have been developed and are described herein.

The human immunoglobulin sequences obtained from the international ImMunoGeneTics informaton system® (IMGT®) database were first aligned to the rabbit Ab-1 sequences described in Example 1 using the IgBLAST tool available from the National Center for Biotechnology Information (NCBI). The V-gene delimitation system was set to the Kabat sequences to obtain the Kabat defined CDRs. In addition, the VH CDR1 defined by AbM was identified since a number of differences were observed in that region that may be important for maintaining the structure. The alignments are shown in FIGS. 8A-D. IGKV1-26*01 was chosen for the light chain variable region and the IghV3-66*01 was chosen for the heavy chain variable region because the CDR2 appeared to be the same length as the rabbit CDR2, whereas the other sequences contained an extra amino acid. See FIG. 8C.

Figure 9A:
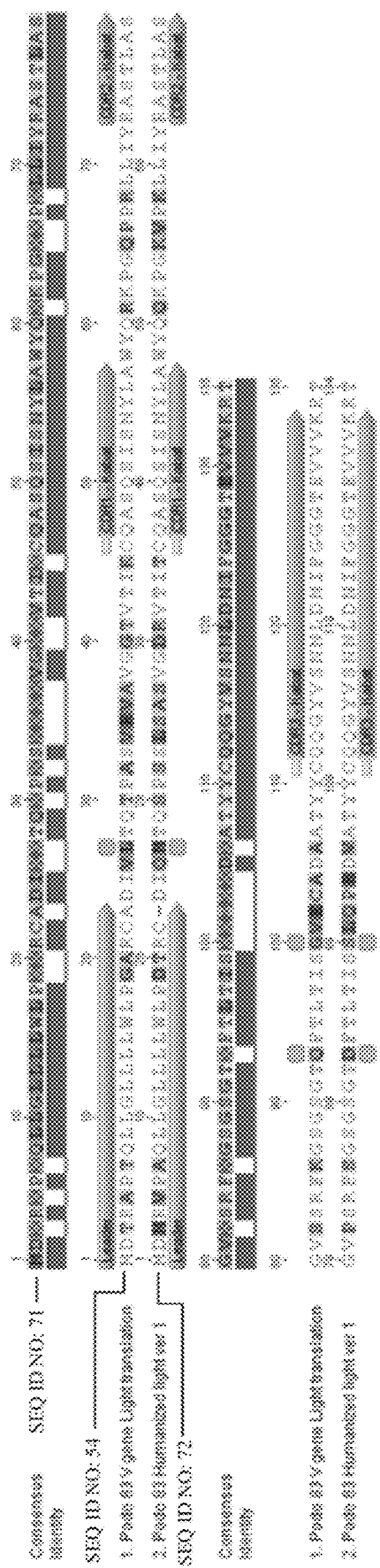
FIG. 9A-B show a comparison of the humanized light chain ("Podo 83 Humanized") (A) and heavy chain ("Podo 83 Humanized") FIG. 9A discloses SEQ ID NOS 71, 54, and 72, respectively, in order of appearance. (B) variable region translated sequences compared to the rabbit sequence ("Podo 83 V gene"), and their respective consensus sequences. The leader sequences and CDRs are identified.
Figure 9B:
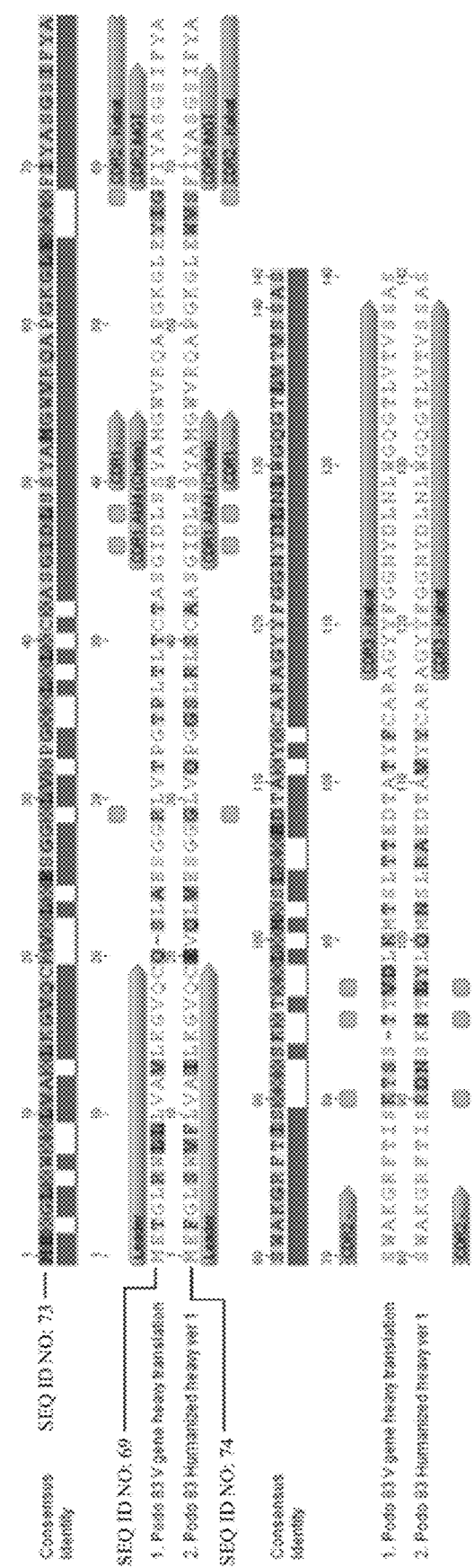

The human CDRs (Kabat numbering) were replaced with the counterpart CDRs from Ab-1. For the heavy chain, the longer CDR3 defined by AbM was used because there were many differences and structurally important amino acids in that region. The humanized light chain and heavy variable chain translated sequences are shown in FIGS. 9A-B compared to the rabbit sequences. Two versions of the humanized heavy chains were produced because there are two extra amino acids in the human heavy chain V gene compared to the rabbit heavy chain V gene. The first humanized heavy chain (1:1) retains the two extra amino acids, which occur at positions 21 and 93/94 as shown in FIG. 9B. The second humanized heavy chain (2:1) has the lysine removed at position 94.

The humanized genes were codon optimized using the codon optimizer from IDT DNA (www.idtdna.com/CodonOpt) using the settings for Homo sapiens. gBlocks® Gene Fragments were ordered from Integrated DNA Technologies (Coralville, Iowa) such that the 5' region of the VH contained a Kozak sequence, EcoRI site and a 21 bp overlap with a pTT5 plasmid containing a hIgG heavy chain constant region sequence (pTT5-hIgHC) digested with EcoRI. The 3' region contained a NheI restriction site followed by a 21 bp overlap with the pTT5-hIgGHC plasmid digested with NheI. The light chain was designed in a similar way with a 5' kozak sequence, and EcoRI site and an 18 bp overlap with a pTT5 plasmid containing a hIgk constant region sequence (pTT5-hIgkC) digested with EcoRI. At the 3' end, the sequence contained a BsiWI site followed by a 20 bp overlap with the pTT5-hIgkC plasmid digested with BsiWI. Sequences of the original rabbit and humanized heavy chain and light chain variable regions used for creating the constructs are shown in FIGS. 10A-J. The Kozak sequences are underlined. The pTT5-hIgGHC plasmid was digested with EcoR1 and NheI and purified from an agarose gel. Similarly, the pTT5-hIgkC plasmid was digested with EcoRI and BsiWI and also purified from an agarose gel. The gBlocks® were resuspended in 20 µl Ultrapure distilled H$_2$O (Gibco, Invitrogen), to a concentration of 10 ng/µl. The following were incubated at 50° C. for 1 hour:

50 ng linearized vector
    20 ng gBlocks®
    6 µl Ultrapure distilled H$_2$O
    10 µl Gibson Assembly Master Mix (2×) (New England Biolabs)

The hIgkC was incubated with the light chain gBlock and the hIgGHC was incubated with the heavy chain gBlock. Dh5α competent bacteria supplied with the Gibson cloning kit were transformed with 2 µl of the mixture and spread onto ampicillin containing agar plates and incubated at 37° C. overnight. Two colonies were picked from each transformation and incubated at 37° C. at 250 rpm in 2 ml LB media containing 100 µg/ml ampicillin overnight. Plasmids were isolated using the Qiagen AIA prep Miniprep kit (Qiagen) according to the manufacturer's instructions. Sequences were verified by sequencing and are shown in FIGS. 11A-J. The sequences of the original rabbit anti-podocalyxin antibody is also shown in FIGS. 11A-D. The underlined, italicized regions correspond to the leader sequence.

Purification of Antibodies

As described above, two humanized VH constructs (1:1 and 2:1) and one humanized Vk construct were made. HEK293 cells were grown to a concentration of 1×10$^6$ cells/ml (96.3% viable) at 37° C., 5% CO2 in 90 ml Freestyle 293 expression media (Gibco), supplemented with 0.1% Pluronic F68 solution. 75 µg of each of the 1:1 and 2:1 VH constructs were mixed with the humanized Vk plasmid DNAs and diluted in 5 ml of Optimem I medium. 130 µl of 293fectin (Invitrogen) was diluted in another tube of 5 ml Optemem I medium. Both tubes were voretexed to mix the contents for 1 second and incubated for 5 min at room temperature. The DNAs were combined with the 293fectin solution and incubated for 20 minutes at room temperature. 10 ml of DNA/293 fectin solution was added dropwise to 90 ml of cells and the flask was swirled to mix the solutions. The cells were incubated for 96 hrs at 37° C., 5% CO2. 96 hours post transfection, supernatants were collected, filter sterilized and stored at 4° C.

Antibodies were purified from supernatants using the AKTAxpress (GE Healthcare) and Mab Select SuRe (GE Healthcare) columns according to the manufacturer's instructions. The eluate was supn through an Amicon Ultra-15 centrifugal filter device with 30 kDa MWCO at 3200×g for 20 min. The concentrated antibodies were resuspended in 15 ml PBS to exchange the buffer and was repeated three times. The final concentrated antibody solution was collected. The concentrated antibody solution was quantified by A280 using the Nanodrop (Thermo Fisher Scientific, Inc). The humanized antibodies obtained were designated Podo 83 1:1 and Podo 83 2:1. Table 4 below shows the yield of each humanized antibody.

TABLE 4

| Sample | Concentration | Total volume | Total Amount |
|---|---|---|---|
| Podo 83 1:1 | 3 mg/ml | 2.75 ml | 8.25 mg |
| Podo 83 2:1 | 3 mg/ml | 2.06 ml | 6.18 mg |

Binding of Humanized Antibodies to Podocalyxin

The humanized antibodies were tested for their binding to endogenously expressing podocalyxin on MDA-MB-231 cells or to both endogenous and transiently expressed podocalyxin on hPodo/MDA-MB-231 transients. The following antibodies were transiently transfected in 293HEK cells, transfected cells were incubated for 96 hours, antibody containing supernatant was then serially titrated in FACS sample buffer. The following supernatants were used as test samples:

1) huPodo 83 1:1 (humanized anti-podocalyxin antibody 83, version 1; comprising SEQ ID NOs:33 and 35)
2) huPodo 83 2:1 (humanized anti-podocalyxin antibody 83, version 2, comprising SEQ ID NOs:33 and 37)
3) Rb/Hu Podo83 (Podo83 rabbit VH and VL, human IgG1 chimera) (comprising SEQ ID NOs:5 and 3)
4) pTT5 (control)
5) Rb V H, Vk 1:1 (Podo 83 rabbit VH comprising SEQ ID NO:3, human CH1-CH3, human Ck, and humanized Vk comprising SEQ ID NO:33)
6) Rabbit Podo 83 (Parental rabbit antibody) (comprising SEQ ID NOs:5 and 3)

MDA transient transfectants were established as essentially described above in Example 1. MDA transient transfectants and MDA-MB-231 cells were seeded in 96-well v bottom plates at 75,000 cells/well. Cells were pelleted by centrifugation at 400 g for 3 min. Supernatant was removed. The cell pellets were resuspended in 20 µl of the antibody or control supernatants. The plate was incubated on ice for 1 hour.

The cells were washed by adding 200 µl FACS buffer to dilute unbound antibody. The plate was centrifuged at 400 g for 3 min to pellet cells. The supernatant was removed and repeated. The cell pellets were resuspended in 25 µl of either goat anti-Hu IgG Fc-Alexa647, goat anti-Mouse IgG Fc-Alexa647, or goat anti-rabbit IgG0Fc-A647 (2 µg/ml) and 7A.A.D (2.5 µg/ml). The plates were incubated on ice for 0.5 hours. The wash procedure was again repeated 2×. The cell pellets were finally resuspended in 75 µl FACS buffer and read on the HTFC™ Screening System (IntelliCyt Corporation) (3 sec sip, 1.5 up time) and analyzed on the Hyper-View® software (IntelliCyt Corporation). Results are shown in Table 5 below. All podocalyxin antibody constructs bound to MDA-MB-231 and hPodo/MDA-MB-231 cells in this assay.

TABLE 5

| | Sup | huPodo 83 1:1 | huPodo 832:1 | Rb/Hu Podo83 | pTT5 | Rb VH, Vk1:1 | Rb Podo 83 (Rb Constant Region) | Rb IgG |
|---|---|---|---|---|---|---|---|---|
| MDA-MB-231 | Neat | 125218 | 122732 | 142636 | 463 | 130009 | 179297 | 574 |
| | 1:5 | 112459 | 104664 | 121432 | 436 | 115091 | 129030 | 467 |
| | 2:15 | 91538 | 67211 | 102250 | 433 | 94785 | 53663 | 438 |
| | 1:125 | 39418 | 22333 | 50614 | 444 | 47673 | 15506 | 431 |
| hPodo/ MDA-MB-231 | Neat | 124260 | 139202 | 78984 | 554 | 137197 | 90788 | 762 |
| | 1:5 | 128183 | 107822 | 99270 | 614 | 124061 | 139018 | 660 |
| | 2:15 | 156609 | 79396 | 154695 | 658 | 76415 | 89664 | 617 |
| | 1:125 | 61564 | 37689 | 58518 | 625 | 74524 | 24084 | 645 |

Relative Affinities of Humanized Antibodies

The affinities of huPodo 83 1:1 and huPodo 83 2:1 antibodies were determined against endogenously expressed podocalyxin on 293 HEK cells. 293-6E cells were seeded in 96-well v bottom plates at 100,000 cells/well. The cells were pelleted at 400 g for 3 min and the supernatant was discarded. The cells were placed on ice and antibody 1:3 titrations were prepared using ice cold medium. The cells were resuspended in the prepared antibody titrations at 25 µl/well and incubated at 4° C. for either 24 or 48 hours. 200 µl 1% FBS/PGS (FACS buffer) was added to each well. The cells were pelleted at 400 g for 3 min and supernatant removed. The wash was repeated 2 more times. The cells were resuspended in goat anti-human IgGFc-A647 (2 µg/ml)+2.5 µg/ml 7AAD and incubated on ice for 30 min. The cells were washed as above and resuspended in 50 µl FACS buffer. The cells were analyzed by flow cytometry using the HTFC™ Screening System (IntelliCyt Corporation) (3 sec sip, 1.5 sec up) and the C6 cytometer (Becton Dickenson).

The $IC_{50}$ values in this assay were:

| | | |
|---|---|---|
| Rb/Hu Podo 83: | 24 hours: 29.5 ng/mL | 48 hours: 30.5 ng/mL |
| huPodo 83 1:1 hum: | 24 hours: 33.06 ng/mL | 48 hours, 35.52 ng/mL |
| huPodo 83 2:1 hum: | 24 hours: 51.93 ng/mL | 48 hours: 51.95 ng/mL |

Example 3—Affinity Determination of Anti-Podocalyxin Antibodies by Kinetic Exclusion Assay The concentration dependence of free anti-podocalyxin antibody as a function of MDA-MB231 cell number was determined using a KinExA 3200 instrument (Sapidyne Instruments). Briefly, MDA-MB-231 cells, which express endogenous podocalyxin, were titrated 1:2 from $10\times10^6$ cells/mL down 12 steps, and incubated with a fixed concentration of anti-podocalyxin antibodies. MDA-MB231 cells and cell bound antibodies were then isolated by centrifugation. Supernatant containing free, unbound antibody was then transferred to a new tube. The supernatant containing free unbound antibody was passed over the column containing PMMA beads coated with a goat anti-IgG-Fc capture antibody. The amount of free antibody captured on the PMMA beads was then measured using a goat anti-IgG-Fc-A647. This process was repeated for every cell concentration. For each sample assayed a new column of PMMA beads with the goat anti-IgG-Fc capture antibody was packed. The concentration of free antibody over the entire 12 step dilution series was then used to determine the antibody Kd's using the standard Kd template in the KineExA Pro Software (Sapidyne Instruments). Results are shown in Table 6.

TABLE 6

| Antibody | Antigen | Kd |
|---|---|---|
| Rb/Hu Podo83 | MDA-MB-231 Cells | 45.59 pM |
| huPodo 83 1:1 | MDA-MB-231 Cells | 259.67 pM |
| Rb/Hu Podo83 | A172 Cells | 102.67 pM |
| 3G2 murine IgG1 | MDA-MB-231 Cells | 3.34 nM |

Example 4—Competition Assay of Anti-Podocalyxin Antibodies

MDA-MB-231 cells endogenously expressing podocalyxin were cultured to logarithmic growth and dissociated from the flask using cell dissociation solution (Sigma C5914). In 96-well v-bottom plates, purified antibodies were incubated with 40,000 MDA-MB-231 cells/well at 25 ug/mL and incubated on ice for 1 hour at 4° C. Purified antibodies (Rb/Hu Podo83 and 3G2) were biotinylated ("B") using the EZ-Link Sulfo-NHS-LC-Biotin (Thermo Fisher Scientific, Inc.) prior to assay and confirmed for binding to MDA-MB-231 cells by flow cytometry using neutravidin-alexa 647 detection. Two commercially available anti-podocalyxin antibodies were biotinylated and used as positive controls; 3D3 (Santa Cruz Biotechnology sc23904), and MAB1658 (R&D Systems). Biotinylated antibodies were then spiked into wells at 5 ug/mL final concentration and the plates were incubated on ice for 1 hour at 4° C. MDA-MB-231 cells were washed with FACS buffer (PBS pH 7.4+1% fetal bovine serum) to remove unbound antibody and pelleted using centrifugation. Neutravidin-Alexa647 was used to detect bound biotinylated antibodies and 7-aminoactinomycin D was added to identify dead cell populations. The samples were washed as above and the samples were acquired on the Intellicyt High Throughput Flow Cytometer (HTFC). Table 7 shows the results of the cross competition FACs assay of the anti-podocalyxin antibodies binding endogenous podocalyxin expressed on MDA-MB231 cells. Table 7 demonstrates that Rb/Hu Podo83 antibody competes with 3G2 antibody.

TABLE 7

| | Rb/Hu Podo83 | B-Herceptin | B-Ova 12 | B-3G2.2 | B-mIgG1 |
|---|---|---|---|---|---|
| 3G2 | 18186 | 4553 | 453 | 2631 | 423 |
| mIgG1 | 124392 | 4808 | 458 | 26553 | 414 |
| MAB 1658 | 127325 | 4716 | 476 | 26909 | 431 |
| 3D3 | 134526 | 4819 | 450 | 26421 | 419 |
| FACS Buffer | 139352 | 4756 | 447 | 26352 | 419 |

Example 5—Tumor Cell Line Selectivity of Anti-Podocalyxin Antibodies

Tumor cell line selectivity was performed essentially as described in Example 1. Table 8 shows the FACS binding profile of Rb/Hu Podo83 antibody (referred to in the table below as "Podo-83") and 3G2 against a panel of tumor cell lines which express podocalyxin, normal endothelial cells (HUVEC), and embryonic kidney cells (HEK293). The results are expressed as geometric mean fluorescence units.

TABLE 8

| | Selectivity Cell Line Panel (Live cell GeoMean FL) | | | | | | | | | |
|---|---|---|---|---|---|---|---|---|---|---|
| Antibody | A172 | HUVEC | 293 HEK | MDA-MB-231 | MCF7 | T47-D | CaOV3 | OVCAR3 | OVCAR10 | SKOV3 |
| Podo-83 | 223501 | 24482 | 28225 | 88890 | 28437 | 1126 | 23357 | 28603 | 1532 | 59773 |
| 3G2.2 | 60417 | 10579 | 22251 | 36744 | 11139 | 2701 | 10372 | 8470 | 2104 | 24860 |
| Control Rb/HuIgG1 | 644 | 489 | 446 | 477 | 657 | 667 | 767 | 629 | 653 | ND |
| RnD anti-hPodo | 94247 | 3594 | 13289 | 17350 | 17193 | 1987 | 17103 | 12974 | 2164 | 35533 |
| MsIgG2a | 797 | 484 | 556 | 478 | 1126 | 787 | 892 | 708 | 618 | 485 |

Example 6—Binding Specificity of Rabbit/Human Podo83 Chimeric Antibodies

Rabbit variable domains of Podo.83 were cloned in human IgG1 or human IgG2 constructs. Recombinant antibody was expressed in 293HEK cells as described previously and purified via protein A chromatography. Binding specificity of recombinant IgG1 and IgG2 versions was confirmed by FACS using MDA-MB231 cells transfected with human Podocalyxin cDNA. MDA-MB-231 cells were seeded into 1×6-well plate at $0.625 \times 10^6$ cells/well in 2 mL of MDA medium (Leibovitz+10% FBS) and incubated overnight at 37° C. and 0% $CO_2$. Cells were then transfected with human Podocalyxin cDNA using Lipofectamie 3000 (Invitrogen) using standard conditions as described by the supplier. Cells were incubated for 24 hours then harvested by centrifugation and washed with FACS buffer. Anti Podo antibodies or isotype controls were then added to the washed cells and allowed to incubate on ice for 30 minuets. These cells were then washed in FACS buffer to remove any unbound antibody and stained with a Gt anti-Hu IgG A657 (0.7 mg/mL, JacksonImmunoResearch). Cells were again incubated for 30 min on ice and then washed with FACS buffer. Bound antibody was measured using by FACS. Results are shown below in Table 9.

TABLE 9

| | hPodo/MDA |
|---|---|
| Rb/huPodo 83 hIgG2 | 98294 |
| Rb/huPodo 83 hIgG1 | 177593 |
| hIgG2 | 533 |
| hIgG1 | 544 |
| FACs only (anti-Hu) | 527 |
| FACs only (anti-Mo) | 550 |

Example 7—Cytotoxic Activity of Anti-Podocalyxin Antibodies

Cytotoxic activity of the rabbit Podo-83, Rb/Hu Podo83, and Podo-3G2.2 antibodies were tested on the human mammary adenocarcinoma cell line MDA-MB-231 (ATCC: HTB-26™) and Human glioblastoma cell line A-172 (ATCC: CRL-1620™) with Saporin-coupled anti-IgG-Fcγ secondary reagents (Advanced Targeting Systems Cat #s, Fab-Zap (human): IT-51-100, Fab-Zap (Rabbit): IT-57-100, Fab-Zap (mouse): IT-48-100). On the day prior to adding test articles, cells were added to opaque-walled 96-well tissue culture-treated microtiter plates using complete growth medium at a density of 2500 cells/100 microlitre (uL) of medium. The cells were incubated for one night at 37° C./5% $CO_2$ (A-172) or 37° C./NO added $CO_2$ (MDA-MB-231) to allow the cells to attach to the microtiter plate surface. Each antibody sample was diluted directly into MDA-MB-231 growth medium at four-times the final concentration and were then titrated 1:3, eight steps. A control with test antibody absent (Fab-Saporin alone) was included on each microtiter plate in triplicate. An additional control of cells+growth medium was included on each mictrotiter plate to compare to the Fab-Saporin alone Control. 50 uL of the medium used to seed the cells was removed from each well and was discarded. The prepared antibody titrations were added (25 uL/well) in triplicate to both the MDA-MB-231 or A-172 cells. Saporin-conjugates were diluted to 4-times the final concentration using MDA-MB-231 growth medium (4-times final=4 ug/mL Fab-Saporin; 1 ug/mL final concentration). The prepared Saporin-Fab dilutions were added (25 uL/well) to the appropriate MDA-MB-231 or A-172 wells. The cells, antibody titrations, and Fab-Saporin were incubated at 37° C./5% $CO_2$ (A-172) or 37° C./NO added $CO_2$ (MDA-MB-231) for five nights. After the incubation, cell viability was measured using CellTiter-Glo® reagent (Promega Corporation) by adding 25 uL of prepared CellTiter-Glo® to each assay well. The assay was incubated for at least ten minutes in the dark prior to measuring emitted luminescence using a microplate luminometer (500 ms integration time). The collected relative luminescence units (RLU) were converted to % cytotoxicity using the Fab-Saporin Alone Control mentioned above (% Cytotoxicity=1−[Well RLU/average Fab-Saporin Alone Control RLU]).

Figure 13:
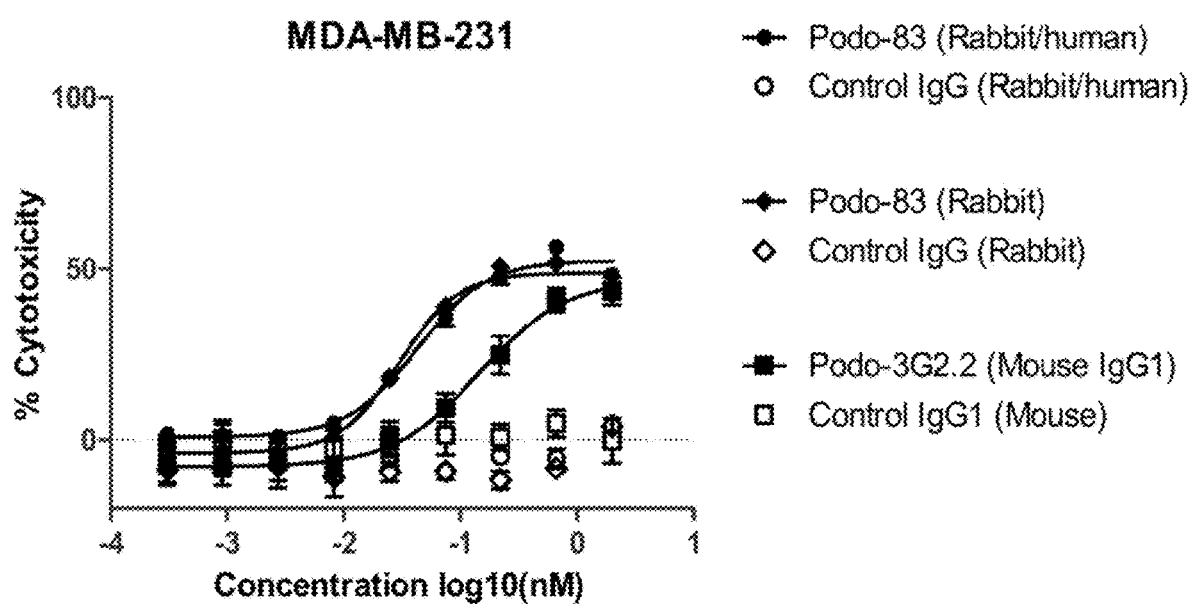
FIG. 13 shows saporin-mediated cytotoxic killing of human mammary adenocarcinoma cell line MDA-MB-231 by the anti-podocalyxin antibodies, Rb/Hu Podo83 and Podo-3G2.2.
Figure 14:
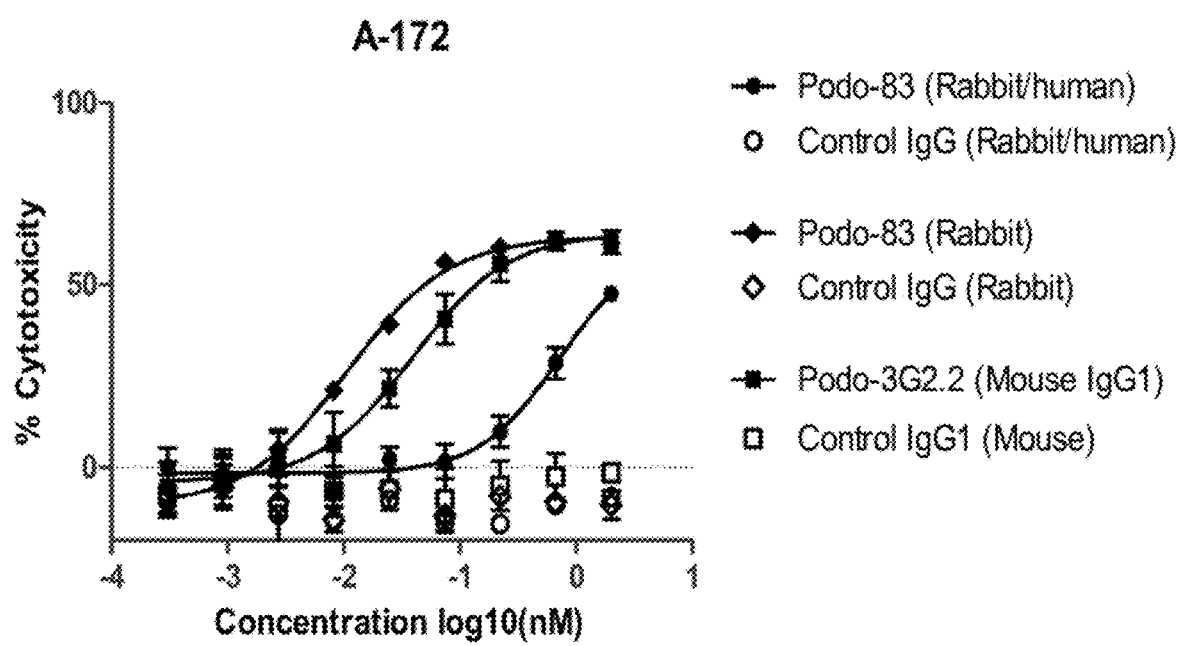
FIG. 14 shows saporin-mediated cytotoxic killing of the human glioblastoma cell line A-172 by the anti-podocalyxin antibodies, Podo-83 (rabbit/human IgG1 chimeric), rabbit Podo-83 (Ab-1), and Podo-3G2.2.

The Fab-Saporin alone controls did not demonstrate significantly reduced viability compared to the Cells+Medium Control (data not shown). FIGS. 13 and 14 show that Podo-83 (both the Rabbit/human chimeric form and the fully rabbit form) and Podo-3G2.2 are capable of acting as antibody-drug conjugates on MDA-MB-231 and A-172 cells. This activity relies on the antibodies effectively internalizing the cell-surface podocalyxin and delivering the Saporin to the intracellular space where it can elicit its ribosome inactivating activity. The same ability would be expected from a covalently coupled anti-podocalyxin toxin conjugate.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An anti-podocalyxin antibody, comprising:
a) a VHCDR1 having amino acid sequence GIDLSSYA set forth in SEQ ID NO: 13;
a VHCDR2 having amino acid sequence IYASGSI set forth in SEQ ID NO: 15;
a VHCDR3 having amino acid sequence ARAGYYFGGNYDLNL set forth in SEQ ID NO: 16;
a VLCDR1 having amino acid sequence QSISNY set forth in SEQ ID NO: 17;
a VLCDR2 having amino acid sequence RAS set forth in SEQ ID NO: 18; and
a VLCDR3 having amino acid sequence QQGYVSNNLDNI set forth in SEQ ID NO: 11, wherein the amino acid sequences of CDRs are defined based on IMGT;
b) a VHCDR1 having amino acid sequence GIDLSSYAMG set forth in SEQ ID NO: 12;
a VHCDR2 having amino acid sequence FIYASGSI set forth in SEQ ID NO: 14;
a VHCDR3 having amino acid sequence AGYYFGG-NYDLNL set forth in SEQ ID NO: 8;
a VLCDR1 having amino acid sequence QASQSIS-NYLA set forth in SEQ ID NO: 9;
a VLCDR2 having amino acid sequence RASTLAS set forth in SEQ ID NO: 10;
and a VLCDR3 having amino acid sequence QQGYVSNNLDNI set forth in SEQ ID NO: 11, wherein the amino acid sequences of CDRs are defined based on Chotia;

c) a VHCDR1 having amino acid sequence SYAMG set forth in SEQ ID NO: 6;
a VHCDR2 having amino acid sequence FIYASGSIFYASWAKG set forth in SEQ ID NO: 7;
a VHCDR3 having amino acid sequence AGYYFGGNYDLNL set forth in SEQ ID NO: 8;
a VLCDR1 having amino acid sequence QASQSISNYLA set forth in SEQ ID NO: 9;
a VLCDR2 having amino acid sequence RASTLAS set forth in SEQ ID NO: 10;
and a VLCDR3 having amino acid sequence QQGYVSNNLDNI set forth in SEQ ID NO: 11,
wherein the amino acid sequences of CDRs are defined based on Kabat;

d) a VHCDR1 having amino acid sequence GYTFTSYV set forth in SEQ ID NO: 21;
a VHCDR2 having amino acid sequence IHPYNDGT set forth in SEQ ID NO: 24;
a VHCDR3 having amino acid sequence ARSWDWYFDV set forth in SEQ ID NO: 26;
a VLCDR1 having amino acid sequence SNVRY set forth in SEQ ID NO: 28;
a VLCDR2 having amino acid sequence DTS set forth in SEQ ID NO: 30; and
a VLCDR3 having amino acid sequence QQWISNPLT set forth in SEQ ID NO: 31,
wherein the amino acid sequences of CDRs are defined based on IMGT;

e) a VHCDR1 having amino acid sequence GYTFTSYVMH set forth in SEQ ID NO: 20;
a VHCDR2 having amino acid sequence YIHPYNDGT set forth in SEQ ID NO: 23;
a VHCDR3 having amino acid sequence SWDWYFDV set forth in SEQ ID NO: 25;
a VLCDR1 having amino acid sequence SANSNVRYIH set forth in SEQ ID NO: 27;
a VLCDR2 having amino acid sequence DTSKLSS set forth in SEQ ID NO: 29;
and a VLCDR3 having amino acid sequence QQWISNPLT set forth in SEQ ID NO: 31,
wherein the amino acid sequences of CDRs are defined based on Chotia; or f) a VHCDR1 having amino acid sequence SYVMH set forth in SEQ ID NO: 19;
a VHCDR2 having amino acid sequence YIHPYNDGTNYNEKFKG set forth in SEQ ID NO: 22;
a VHCDR3 having amino acid sequence SWDWYFDV set forth in SEQ ID NO: 25;
a VLCDR1 having amino acid sequence SANSNVRYIH set forth in SEQ ID NO: 27;
a VLCDR2 having amino acid sequence DTSKLSS set forth in SEQ ID NO: 29;
and a VLCDR3 having amino acid sequence QQWISNPLT set forth in SEQ ID NO: 31,
wherein the amino acid sequences of CDRs are defined based on Kabat.

2. The antibody of claim 1, wherein the antibody is a chimeric, humanized, or human antibody.

3. The antibody of claim 1, wherein at least a portion of the framework sequence is a human consensus framework sequence.

4. The antibody of claim 1, wherein the antibody is a monoclonal antibody.

5. The antibody of claim 4, wherein the antibody is humanized.

6. The antibody of claim 4, which is an antibody fragment.

7. The antibody of claim 6, wherein the antibody fragment is selected from a Fab, Fab'-SH, Fv, scFv or (Fab')2 fragment.

8. The antibody of claim 1, where the antibody comprises an Fc region.

9. The antibody of claim 1, wherein the antibody comprises:
(i) a heavy chain variable domain comprising SEQ ID NO: 3 and a light chain variable domain comprising SEQ ID NO: 5;
(ii) a heavy chain variable domain comprising SEQ ID NO: 39 and a light chain variable domain comprising SEQ ID NO: 41;
(iii) a heavy chain variable domain comprising SEQ ID NO: 35 and a light chain variable domain comprising SEQ ID NO: 33; or
(iv) a heavy chain variable domain comprising SEQ ID NO: 37 and a light chain variable domain comprising SEQ ID NO: 33.

10. A polynucleotide encoding the heavy chain variable region and/or the light chain variable region of claim 9.

11. The polynucleotide of claim 10, wherein the polynucleotide is selected from the group consisting of SEQ ID NOs: 2, 4, 32, 34, 36, 38, and 40.

12. A vector comprising the polynucleotide of claim 11.

13. A host cell comprising the vector of claim 12.

14. A method of inhibiting the growth of a tumor that expresses podocalyxin in vivo, said method comprising administering an antibody as defined in claim 1 to a patient having said tumor, thereby causing one or more of (i) inhibition of growth or proliferation of a cell to which said antibody binds; (ii) induction of death of a cell to which said antibody binds; (iii) inhibition of delamination of a cell to which said antibody binds; (iv) inhibition of the metastasis of a cell to which it binds; and (v) inhibition of the vascularization of said tumor.

15. A pharmaceutical composition comprising an antibody as defined in claim 1 and a pharmaceutically acceptable carrier.

16. A method of treating a subject having cancer, inhibiting tumor metastasis in a subject or inhibiting tumor vasculature in a subject, said method comprising administering to the subject the pharmaceutical composition of claim 15.

17. The method of claim 16, wherein the subject is human.

* * * * *